(12) United States Patent
Watanabe et al.

(10) Patent No.: US 9,512,424 B2
(45) Date of Patent: Dec. 6, 2016

(54) ANTISENSE NUCLEIC ACIDS

(71) Applicants: NIPPON SHINYAKU CO., LTD., Kyoto-shi, Kyoto (JP); NATIONAL CENTER OF NEUROLOGY AND PSYCHIATRY, Kodaira-shi, Tokyo (JP)

(72) Inventors: Naoki Watanabe, Ibaraki (JP); Haruna Seo, Tokyo (JP); Shin'ichi Takeda, Tokyo (JP); Tetsuya Nagata, Tokyo (JP)

(73) Assignees: NIPPON SHINYAKU CO., LTD., Kyoto-shi, Kyoto (JP); NATIONAL CENTER OF NEUROLOGY AND PSYCHIATRY, Tokyo (JP)

( * ) Notice: Subject to any disclaimer, the term of this patent is extended or adjusted under 35 U.S.C. 154(b) by 25 days.

(21) Appl. No.: 14/368,307

(22) PCT Filed: Dec. 27, 2012

(86) PCT No.: PCT/JP2012/084295
§ 371 (c)(1),
(2) Date: Jun. 24, 2014

(87) PCT Pub. No.: WO2013/100190
PCT Pub. Date: Jul. 4, 2013

(65) Prior Publication Data
US 2014/0343266 A1 Nov. 20, 2014

(30) Foreign Application Priority Data

Dec. 28, 2011 (JP) ................. 2011-288040
Feb. 29, 2012 (JP) ................. 2012-043092

(51) Int. Cl.
| | |
|---|---|
| C07H 21/02 | (2006.01) |
| C07H 21/04 | (2006.01) |
| C12N 15/113 | (2010.01) |
| C12N 15/11 | (2006.01) |

(52) U.S. Cl.
CPC ........... *C12N 15/113* (2013.01); *C12N 15/111* (2013.01); *C12N 2310/11* (2013.01); *C12N 2310/314* (2013.01); *C12N 2310/315* (2013.01); *C12N 2310/321* (2013.01); *C12N 2310/322* (2013.01); *C12N 2310/3233* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 7,807,816 B2 | 10/2010 | Wilton et al. | |
| 8,779,128 B2* | 7/2014 | Hanson ................. | C07F 9/5727 544/121 |
| 2008/0194463 A1* | 8/2008 | Weller ................. | A61K 48/00 514/1.1 |
| 2009/0269755 A1* | 10/2009 | Aartsma-Rus ..... | A61K 48/0016 435/6.11 |
| 2010/0168212 A1 | 7/2010 | Popplewell et al. | |
| 2011/0263682 A1 | 10/2011 | De Kimpe et al. | |
| 2012/0046342 A1 | 2/2012 | Van Deutekom et al. | |

FOREIGN PATENT DOCUMENTS

| | | |
|---|---|---|
| JP | 2006-523101 A | 10/2006 |
| WO | WO-2004/048570 A1 | 6/2004 |
| WO | WO-2004/083446 A2 | 9/2004 |
| WO | WO-2006/000057 A1 | 1/2006 |
| WO | WO-2009054725 A2 | 4/2009 |
| WO | WO-2009/139630 A2 | 11/2009 |
| WO | WO-2010/048586 A1 | 4/2010 |
| WO | WO-2010/050801 A1 | 5/2010 |
| WO | WO-2010/050802 A2 | 5/2010 |
| WO | WO-2010/123369 A1 | 10/2010 |
| WO | WO-2011/057350 A1 | 5/2011 |
| WO | WO 2011/150408 A2 | 12/2011 |

OTHER PUBLICATIONS

EP Application No. 12861221.5—Extended European Search Report mailed Oct. 19, 2015.
Annemieke Aartsma-Rus, et al., "Targeted exon skipping as a potential gene correction therapy for Duchenne muscular dystrophy," Neuromuscular Disorders 12 (2002), pp. S71-S77.
Annemieke Aartsma-Rus, et al., "Antisense-induced exon skipping for duplications in Duchenne muscular dystrophy," BMC Medical Genetics, 2007, vol. 8, No. 43, doi: 10.1186/1471-2350-8-43, pp. 1-9.
Annemieke Aartsma-Rus, et al., "Antisense-Induced Multiexon Skipping for Duchenne Muscular Dystrophy Makes More Sense," Am. J. Hum. Genet., 2004, vol. 74, pp. 83-92.
Annemieke Artsma-Rus, et al., "Exploring the Frontiers of Therapeutic Exon Skipping for Duchenne Muscular Dystrophy by Double Targeting within One or Multiple Exons," Molecular Therapy, 2006, vol. 14, No. 3, pp. 401-407.
Christopher Béroud, et al., "Multiexon Skipping Leading to an Artificial DMD Protein Lacking Amino Acids from Exons 45 Through 55 Could Rescue Up to 63% of Patients With Duchenne Muscular Dystrophy," Human Mutation, 2007, vol. 28, No. 2, pp. 196-202.
Hans A. Heemskerk, et al., "In vivo comparison of 2'-O-methyl Phosphorothioate and morpholino antisense oligonucleotides for Duchenne muscular dystrophy exon skipping," The Journal of Gene Medicine, 2009, vol. 11, pp. 257-266.
Yihong Hu, et al., "Guanine Analogues Enhance Antisense Oligonucleotide-induced Exon Skipping in Dystrophin Gene In Vitro and In Vivo," Mol. Ther., 2010, vol. 18, No. 4, pp. 812-818.
M. Kobayashi, et al., "Molecular theraphy of muscular dystrophy with exon skipping," Journal of Clinical and Experimental Medicine, Apr. 2011, vol. 237, No. 6, pp. 251-257.
Qi Long Lu, et al., "The Status of Exon Skipping as a Therapeutic Approach to Duchenne Muscular Dystrophy," Molecular Therapy, 2010, vol. 19, No. 1, pp. 9-15.

(Continued)

*Primary Examiner* — Richard Schnizer
(74) *Attorney, Agent, or Firm* — Drinker Biddle & Reath LLP

(57) ABSTRACT

The present invention provides a pharmaceutical agent which causes skipping of the 55th, 45th, 50th or 44th exon in the human dystrophin gene with a high efficiency. The present invention provides an oligomer which efficiently enables to cause skipping of the 55th, 45th, 50th or 44th exon in the human dystrophin gene.

9 Claims, 31 Drawing Sheets

(56) References Cited

OTHER PUBLICATIONS

Rusdy Ghazali Malueka, et al., "Antisense Oligonucleotide Induced *Dystrophin* Exon 45 Skipping at a Low Half-Maximal Effective Concentration in a Cell-Free Splicing System," Nucleic Acid Theapeutics, 2011, vol. 21, No. 5, pp. 347-353.

Masafumi Matsuo, "Duchenne / Becker muscular dystrophy: from molecular diagnosis to gene therapy," Brain & Development, 1996; 18: pp. 167-172.

Linda. J. Popplewell, et al., "Comparative analysis of antisense oligonucleotide sequences targeting exon 53 of the human DMD gene: Implications for future clinical trials," Neuromuscular Disorders, 2010, vol. 20, No. 2, pp. 102-110.

Miho Takagi, et al., "Design of 2'-O-Me RNA/ENA™ chimera oligonucleotides to induce exon skipping in dystrophin pre-mRNA," Nucleic Acids Symposium Series No. 48, 2004, pp. 297-298.

Masafumi Matsuo, "Duchenne/Becker muscular dystrophy: from molecular diagnosis to gene therapy," Brain & Development, 1996; 18: pp. 167-172.

Anthony P. Monaco, et al., "An Explanation for the Phenotypic Differences between Patients Bearing Partial Deletions of the DMD Locus," Genomics, 1988; 2: pp. 90-95.

Hong M. Moulton, et al., "Morpholinos and their peptide conjugates: Therapeutic promise and challenge for Duchenne muscular dystrophy," Biochim. Biophys. Acta., 2010, vol. 1798, pp. 2296-2303.

Akinori Nakamura, et al., "Exon skipping theraphy for Duchenne muscular dystrophy: outcome of preclinical study and prospective for clinical study," Noto Hattatsu, 2010, vol. 42, pp. 117-123.

Christophe Pichavant, et al., "Current Status of Pharmaceutical and Genetic Therapeutic Approaches to Treat DMD," Mol. Ther., May 2011, vol. 19, No. 5., pp. 830-840.

Linda. J. Popplewell, et al., "Comparative analysis of antisense oligonucleotide sequences targeting exon 53 of the human DMD gene: Implications for future clinical trials," Neuromuscular Disorders, 2010, vol. 20, No. 2, pp. 102-10.

Takashi Saito, et al., "Development of Exaon Skipping Therapy for Duchenne Muscular Dystrophy Using Patient-Derived Cells," Dai 32 Kai The Japanese Society of Clinical Pharmacology and Therapeutics Nenkai Symposium 2: Hito Soshiki o Mochiita Rinsho Yakurigaku Kenkyu no Hatten, Dec. 3, 2011 (Dec. 3, 2011), Jpn. J. Clin. Pharmacol. Ther., 2012, vol. 43, No. 2, pp. 91-92.

Miho Takagi, et al., "Design of 2'-O-Me RNA/ENA™ chimera oligonucleotides to induce exon skipping in dystrophin pre-mRNA," Nucleic Acids Symposium Series No. 48, 2004, pp. 297-298.

Steve D. Wilton, et al., "Antisense Oligonucleotide-induced Exon Skipping Across the Human Dystrophin Gene Transcript," Molecular Therapy 2007: 15: pp. 1288-1296.

Bo Wu, et al., "Targeted Skipping of Human Dystrophin Exons in Transgenic Mouse Model Systemically for Antisense Drug Development," PLoS One, May 2011, vol. 6, No. 5, e 19906, pp. 1-11.

International Search Report mailed on Mar. 12, 2013 for PCT/JP2012/084295 filed Dec. 27, 2012.

\* cited by examiner

SEQUENCE LISTING

```
<160> NUMBER OF SEQ ID NOS: 122

<210> SEQ ID NO 1
<211> LENGTH: 192
<212> TYPE: DNA
<213> ORGANISM: Homo sapiens

<400> SEQUENCE: 1
agggtgagtg agcgagaggc tgctttggaa gaaactcata gattactgca acagttcccc      60
ctggacctgg aaaagtttct tgcctggctt acagaagctg aaacaactgc caatgtccta     120
caggatgcta cccgtaagga aaggctccta gaagactcca agggagtaaa agagctgatg     180
aaacaatggc aa                                                         192
```

<210> SEQ ID NO 2
<211> LENGTH: 179
<212> TYPE: DNA
<213> ORGANISM: Homo sapiens

<400> SEQUENCE: 2

```
caggaactcc aggatggcat tgggcagcgg caaactgttg tcagaacatt gaatgcaact      60
ggggaagaaa taattcagca atcctcaaaa acagatgcca gtattctaca ggaaaaattg     120
ggaagcctga atctgcggtg gcaggaggtc tgcaaacagc tgtcagacag aaaaaagag     179
```

<210> SEQ ID NO 3
<211> LENGTH: 129
<212> TYPE: DNA
<213> ORGANISM: Homo sapiens

<400> SEQUENCE: 3

```
aggaagttag aagatctgag ctctgagtgg aaggcggtaa accgtttact tcaagagctg      60
agggcaaagc agcctgacct agctcctgga ctgaccacta ttggagcctg taagtatact     120
ggatcccat                                                             129
```

<210> SEQ ID NO 4
<211> LENGTH: 148
<212> TYPE: DNA
<213> ORGANISM: Homo sapiens

<400> SEQUENCE: 4

```
gcgatttgac agatctgttg agaaatggcg gcgttttcat tatgatataa agatatttaa      60
tcagtggcta acagaagctg aacagtttct cagaaagaca caaattcctg agaattggga     120
acatgctaaa tacaaatggt atcttaag                                        148
```

<210> SEQ ID NO 5
<211> LENGTH: 192
<212> TYPE: DNA
<213> ORGANISM: Homo sapiens

<400> SEQUENCE: 5

```
ttgccattgt ttcatcagct cttttactcc cttggagtct tctaggagcc tttccttacg      60
ggtagcatcc tgtaggacat tggcagttgt ttcagcttct gtaagccagg caagaaactt     120
ttccaggtcc aggggggaact gttgcagtaa tctatgagtt tcttccaaag cagcctctcg    180
ctcactcacc ct                                                         192
```

<210> SEQ ID NO 6
<211> LENGTH: 179
<212> TYPE: DNA
<213> ORGANISM: Homo sapiens

<400> SEQUENCE: 6

```
ctcttttttc tgtctgacag ctgtttgcag acctcctgcc accgcagatt caggcttccc      60
aattttttcct gtagaatact ggcatctgtt tttgaggatt gctgaattat ttcttcccca    120
gttgcattca atgttctgac aacagtttgc cgctgcccaa tgccatcctg gagttcctg     179
```

<210> SEQ ID NO 7
<211> LENGTH: 129
<212> TYPE: DNA
<213> ORGANISM: Homo sapiens

<400> SEQUENCE: 7

```
atgggatcca gtatacttac aggctccaat agtggtcagt ccaggagcta ggtcaggctg    60
ctttgccctc agctcttgaa gtaaacggtt taccgccttc cactcagagc tcagatcttc   120
taacttcct                                                           129
```

<210> SEQ ID NO 8
<211> LENGTH: 148
<212> TYPE: DNA
<213> ORGANISM: Homo sapiens

<400> SEQUENCE: 8

```
cttaagatac catttgtatt tagcatgttc ccaattctca ggaatttgtg tctttctgag    60
aaactgttca gcttctgtta gccactgatt aaatatcttt atatcataat gaaaacgccg   120
ccatttctca acagatctgt caaatcgc                                      148
```

<210> SEQ ID NO 9
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 9

```
caatgccatc ctggagttcc t                                              21
```

<210> SEQ ID NO 10
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 10

```
ccaatgccat cctggagttc c                                              21
```

<210> SEQ ID NO 11
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 11

```
cccaatgcca tcctggagtt c                                              21
```

<210> SEQ ID NO 12
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 12

```
gcccaatgcc atcctggagt t                                              21
```

<210> SEQ ID NO 13
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 13
tgcccaatgc catcctggag t                                              21

<210> SEQ ID NO 14
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 14
cccaatgcca tcctggagtt cctgt                                          25

<210> SEQ ID NO 15
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 15
cagtttgccg ctgcccaatg ccatcctgga                                     30

<210> SEQ ID NO 16
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 16
ccaatgccat cctggagttc                                                20

<210> SEQ ID NO 17
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 17
cccaatgcca tcctggagtt                                                20

<210> SEQ ID NO 18
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 18
cccaatgcca tcctggagtt c                                              21

<210> SEQ ID NO 19
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 19
gcugcccaau gccauccugg aguuc                                          25

<210> SEQ ID NO 20
<211> LENGTH: 25
<212> TYPE: DNA

<213> ORGANISM: Artificial
<220> FEATURE:
<223> OTHER INFORMATION: Synthetic Nucleic Acid

<400> SEQUENCE: 20
uugccgcugc ccaaugccau ccugg                                    25

<210> SEQ ID NO 21
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 21
acaguuugcc gcugcccaau gccau                                    25

<210> SEQ ID NO 22
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 22
ugacaacagu uugccgcugc ccaau                                    25

<210> SEQ ID NO 23
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 23
uguucugaca acaguuugcc gcugc                                    25

<210> SEQ ID NO 24
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 24
uucaauguuc ugacaacagu uugcc                                    25

<210> SEQ ID NO 25
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 25
uugcauucaa uguucugaca acagu                                    25

<210> SEQ ID NO 26
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 26
cccaguugca uucaauguuc ugaca                                    25

<210> SEQ ID NO 27
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 27
ucuuccccag uugcauucaa uguuc                                    25

<210> SEQ ID NO 28
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 28
uuauuucuuc cccaguugca uucaa                                    25

<210> SEQ ID NO 29
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 29
cugaauuauu ucuuccccag uugca                                    25

<210> SEQ ID NO 30
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 30
gauugcugaa uuauuucuuc cccag                                    25

<210> SEQ ID NO 31
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 31
uugaggauug cugaauuauu ucuuc                                    25

<210> SEQ ID NO 32
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 32 uguuuugag gauugcugaa uuauu                                     25

<210> SEQ ID NO 33
<211> LENGTH: 25
<212> TYPE: DNA
<213> ORGANISM: Artificial
<220> FEATURE:

<223> OTHER INFORMATION: Synthetic Nucleic Acid

<400> SEQUENCE: 33
gcaucuguuu uugaggauug cugaa                                          25

<210> SEQ ID NO 34
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 34
uacuggcauc uguuuugag gauug                                           25

<210> SEQ ID NO 35
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 35
uuugccgcug cccaaugcca uccug                                          25

<210> SEQ ID NO 36
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 36
gctcaggtcg gattgacatt                                                20

<210> SEQ ID NO 37
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 37
gggcaactct tccaccagta                                                20

<210> SEQ ID NO 38
<211> LENGTH: 963
<212> TYPE: DNA
<213> ORGANISM: Homo sapiens

<400> SEQUENCE: 38
atggagctac tgtcgccacc gctccgcgac gtagacctga cggcccccga cggctctctc    60
tgctcctttg ccacaacgga cgacttctat gacgacccgt gtttcgactc cccggacctg   120
cgcttcttcg aagacctgga cccgcgcctg atgcacgtgg gcgcgctcct gaaacccgaa   180
gagcactcgc acttccccgc ggcggtgcac ccggccccgg gcgcacgtga ggacgagcat   240
gtgcgcgcgc ccagcgggca ccaccaggcg ggccgctgcc tactgtgggc ctgcaaggcg   300
tgcaagcgca agaccaccaa cgccgaccgc cgcaaggccg ccaccatgcg cgagcggcgc   360
cgcctgagca agtaaatga ggcctttgag acactcaagc gctgcacgtc gagcaatcca   420
aaccagcggt tgcccaaggt ggagatcctg cgcaacgcca tccgctatat cgagggcctg   480
caggctctgc tgcgcgacca ggacgccgcg cccctggcg ccgcagccgc cttctatgcg   540

```
ccgggcccgc tgccccgggg ccgcggcggc gagcactaca gcggcgactc cgacgcgtcc    600
agcccgcgct ccaactgctc cgacggcatg atggactaca cggcccccc gagcggcgcc     660 cggcggcgga actgctacga aggcgcctac tacaacgagg cgcccagcga acccaggccc    720
gggaagagtg cggcggtgtc gagcctagac tgcctgtcca gcatcgtgga gcgcatctcc    780
accgagagcc ctgcggcgcc cgccctcctg ctggcggacg tgccttctga gtcgcctccg    840
cgcaggcaag aggctgccgc ccccagcgag ggagagagca cgggcgaccc cacccagtca    900
ccggacgccg cccgcagtg ccctgcgggt gcgaaccca acccgatata ccaggtgctc      960
tga                                                                  963
```

<210> SEQ ID NO 39
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 39

```
cctgagaatt gggaacatgc                                                 20
```

<210> SEQ ID NO 40
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 40

```
ttgctgctct tttccaggtt                                                 20
```

<210> SEQ ID NO 41
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 41

```
agcagcctct cgctcactca c                                               21
```

<210> SEQ ID NO 42
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 42

```
ttccaaagca gcctctcgct c                                               21
```

<210> SEQ ID NO 43
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 43

```
ttcttccaaa gcagcctctc g                                               21
```

<210> SEQ ID NO 44

```
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 44
agtttcttcc aaagcagcct c                                              21

<210> SEQ ID NO 45
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 45
tttcttccaa agcagcctct c                                              21

<210> SEQ ID NO 46
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 46
gtttcttcca aagcagcctc t                                              21

<210> SEQ ID NO 47
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 47
gagtttcttc caaagcagcc t                                              21

<210> SEQ ID NO 48
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 48
tgagtttctt ccaaagcagc c                                              21

<210> SEQ ID NO 49
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 49
gcagccucuc gcucacucac c                                              21

<210> SEQ ID NO 50
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 50
```
ccaaagcagc cucucgcuca c                                          21

<210> SEQ ID NO 51
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 51
uucuuccaaa gcagccucuc g                                          21

<210> SEQ ID NO 52
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 52
aucuaugagu uucuuccaaa g                                          21

<210> SEQ ID NO 53
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 53
uguugcagua aucuaugagu u                                          21

<210> SEQ ID NO 54
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 54 caggggaac uguugcagua a                                           21

<210> SEQ ID NO 55
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 55
uuuccagguc caggggaac u                                           21

<210> SEQ ID NO 56
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 56
gcaagaaacu uuuccagguc c                                          21

<210> SEQ ID NO 57
<211> LENGTH: 21
<212> TYPE: DNA

<213> ORGANISM: Artificial
<220> FEATURE:
<223> OTHER INFORMATION: Synthetic Nucleic Acid

<400> SEQUENCE: 57
uguaagccag gcaagaaacu u        21

<210> SEQ ID NO 58
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 58
uuucagcuuc uguaagccag g        21

<210> SEQ ID NO 59
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 59
uuggcaguug uuucagcuuc u        21

<210> SEQ ID NO 60
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 60
cuguaggaca uuggcaguug u        21

<210> SEQ ID NO 61
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 61
ggguagcauc cuguaggaca u        21

<210> SEQ ID NO 62
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 62
cuuuccuuac ggguagcauc c        21

<210> SEQ ID NO 63
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 63
uucuaggagc cuuuccuuac g        21

<210> SEQ ID NO 64
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 64
ccuuggaguc uucuaggagc c                                        21

<210> SEQ ID NO 65
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 65
ucuuuuacuc ccuuggaguc u                                        21

<210> SEQ ID NO 66
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 66
uuucaucagc ucuuuuacuc c                                        21

<210> SEQ ID NO 67
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 67
uugccauugu uucaucagcu                                          20

<210> SEQ ID NO 68
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 68
uccuguagga cauuggcagu                                          20

<210> SEQ ID NO 69
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 69
catggaagga gggtccctat                                          20

<210> SEQ ID NO 70
<211> LENGTH: 20
<212> TYPE: DNA
<213> ORGANISM: Artificial
<220> FEATURE:

<223> OTHER INFORMATION: Synthetic Nucleic Acid

<400> SEQUENCE: 70
ctgccggctt aattcatcat                                           20

<210> SEQ ID NO 71
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 71
ataatgaaaa cgccgccatt t                                         21

<210> SEQ ID NO 72
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 72
tcataatgaa aacgccgcca t                                         21

<210> SEQ ID NO 73
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 73
atcataatga aaacgccgcc a                                         21

<210> SEQ ID NO 74
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 74
tatcataatg aaaacgccgc c                                         21

<210> SEQ ID NO 75
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 75
atatcataat gaaaacgccg c                                         21

<210> SEQ ID NO 76
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 76
tatatcataa tgaaaacgcc g                                         21

```
<210> SEQ ID NO 77
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 77
ttatatcata atgaaaacgc c                                             21

<210> SEQ ID NO 78
<211> LENGTH: 30
<212> TYPE: DNA
<213> ORGANISM: Artificial
<220> FEATURE:
<223> OTHER INFORMATION: Synthetic Nucleic Acid

<400> SEQUENCE: 78
tgaaaacgcc gccatttctc aacagatctg                                    30

<210> SEQ ID NO 79
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 79
atcataatga aaacgccgcc                                               20

<210> SEQ ID NO 80
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 80
tatcataatg aaaacgccgc                                               20

<210> SEQ ID NO 81
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 81
tatcataatg aaaacgccgc c                                             21

<210> SEQ ID NO 82
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 82
cucaacagau cugucaaauc gc                                            22

<210> SEQ ID NO 83
<211> LENGTH: 22
<212> TYPE: DNA
<213> ORGANISM: Artificial
<220> FEATURE:
<223> OTHER INFORMATION: Synthetic Nucleic Acid
```

```
<400> SEQUENCE: 83
gccgccauuu cucaacagau cu                                              22

<210> SEQ ID NO 84
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 84
uaaugaaaac gccgccauuu cu                                              22

<210> SEQ ID NO 85
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 85
uaucauaaug aaaacgccgc ca                                              22

<210> SEQ ID NO 86
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 86
cuuuauauca uaaugaaaac gc                                              22

<210> SEQ ID NO 87
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 87
gauuaaauau cuuuauauca ua                                              22

<210> SEQ ID NO 88
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 88
guuagccacu gauuaaauau cu                                              22

<210> SEQ ID NO 89
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 89
uucagcuucu guuagccacu ga                                              22

<210> SEQ ID NO 90
<211> LENGTH: 22
```

```
<212> TYPE: DNA
<213> ORGANISM: Artificial
<220> FEATURE:
<223> OTHER INFORMATION: Synthetic Nucleic Acid

<400> SEQUENCE: 90
ugagaaacug uucagcuucu gu                                              22

<210> SEQ ID NO 91
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 91
ugugucuuuc ugagaaacug uu                                              22

<210> SEQ ID NO 92
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 92
guucccaauu cucaggaauu ug                                              22

<210> SEQ ID NO 93
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 93
uauuuagcau guucccaauu cu                                              22

<210> SEQ ID NO 94
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 94
auaccauuug uauuuagcau gu                                              22

<210> SEQ ID NO 95
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 95
ucagcuucug uuagccacug                                                 20

<210> SEQ ID NO 96
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 96
```
tccagtatac ttacaggctc c                              21

<210> SEQ ID NO 97
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 97
atccagtata cttacaggct c                              21

<210> SEQ ID NO 98
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 98
gatccagtat acttacaggc t                              21

<210> SEQ ID NO 99
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 99
ggatccagta tacttacagg c                              21

<210> SEQ ID NO 100
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 100
gggatccagt atacttacag g                              21

<210> SEQ ID NO 101
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 101
cttacaggct ccaatagtgg tcagt                          25

<210> SEQ ID NO 102
<211> LENGTH: 25
<212> TYPE: DNA
<213> ORGANISM: Artificial
<220> FEATURE:
<223> OTHER INFORMATION: Synthetic Nucleic Acid

<400> SEQUENCE: 102
gggatccagt atacttacag gctcc                          25

<210> SEQ ID NO 103
<211> LENGTH: 20
<212> TYPE: DNA
<213> ORGANISM: Artificial

```
<220> FEATURE:
<223> OTHER INFORMATION: Synthetic Nucleic Acid

<400> SEQUENCE: 103
aacaaccgga tgtggaagag                                              20

<210> SEQ ID NO 104
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 104
ttggagatgg cagtttcctt                                              20

<210> SEQ ID NO 105
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 105
cauuucucaa cagaucuguc aa                                           22

<210> SEQ ID NO 106
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 106
aaaacgccgc cauuucucaa ca                                           22

<210> SEQ ID NO 107
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 107
aauaucuuua uaucauaaug aa                                           22

<210> SEQ ID NO 108
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 108
cuucuguuag ccacugauua aa                                           22

<210> SEQ ID NO 109
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 109
aacuguucag cuucuguuag cc                                           22
```

```
<210> SEQ ID NO 110
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 110
cuuucugaga aacuguucag cu                                              22

<210> SEQ ID NO 111
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 111
gaauuugugu cuuucugaga aa                                              22

<210> SEQ ID NO 112
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 112
cucaggaauu ugugucuuuc ug                                              22

<210> SEQ ID NO 113
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 113
caauucucag gaauuugugu cu                                              22

<210> SEQ ID NO 114
<211> LENGTH: 22
<212> TYPE: DNA
<213> ORGANISM: Artificial
<220> FEATURE:
<223> OTHER INFORMATION: Synthetic Nucleic Acid

<400> SEQUENCE: 114
agcauguucc caauucucag ga                                              22

<210> SEQ ID NO 115
<211> LENGTH: 18
<212> TYPE: DNA
<213> ORGANISM: Artificial
<220> FEATURE:
<223> OTHER INFORMATION: Synthetic Nucleic Acid

<400> SEQUENCE: 115
gagtcttcta ggagcctt                                                   18

<210> SEQ ID NO 116
<211> LENGTH: 20
<212> TYPE: DNA
<213> ORGANISM: Artificial
<220> FEATURE:
<223> OTHER INFORMATION: Synthetic Nucleic Acid
```

<400> SEQUENCE: 116
gtttcttcca aagcagcctc                                               20

<210> SEQ ID NO 117
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 117
agtttcttcc aaagcagcct                                               20

<210> SEQ ID NO 118
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 118
agtttcttcc aaagcagcct c                                             21

<210> SEQ ID NO 119
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 119
ggatccagta tacttacagg                                               20

<210> SEQ ID NO 120
<211> LENGTH: 20
<212> TYPE: DNA
<213> ORGANISM: Artificial
<220> FEATURE:
<223> OTHER INFORMATION: Synthetic Nucleic Acid

<400> SEQUENCE: 120
gggatccagt atacttacag                                               20

<210> SEQ ID NO 121
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 121
tgggatccag tatacttaca g                                             21

<210> SEQ ID NO 122
<211> LENGTH: 21
<212> TYPE: DNA
<213> ORGANISM: Artificial
<220> FEATURE:
<223> OTHER INFORMATION: Synthetic Nucleic Acid

<400> SEQUENCE: 122
atgggatcca gtatacttac a                                             21

ANTISENSE NUCLEIC ACIDS

CROSS REFERENCE TO RELATED APPLICATIONS

This application is the National Stage of International Application No. PCT/JP2012/084295, filed Dec. 27, 2012, and claims benefit of Japanese Application Nos. 2011-288040, filed on Dec. 28, 2011, and 2012-043092, filed on Feb. 29, 2012.

SEQUENCE LISTING

The instant application contains a sequence listing which has been submitted in ASCII format via EFS-Web and is hereby incorporated by reference in its entirety. Said ASCII copy, created on Dec. 22, 2012, is named G1130_Seq_Listing.txt and is 25,363 bytes in size.

TECHNICAL FIELD

The present invention relates to an antisense oligomer which causes skipping of exon 55, 45, 50 or 44 in the human dystrophin gene, and a pharmaceutical composition comprising the oligomer.

BACKGROUND ART

Duchenne muscular dystrophy (DMD) is the most frequent form of hereditary progressive muscular dystrophy that affects one in about 3,500 newborn boys. Although the motor functions are rarely different from healthy humans in infancy and childhood, muscle weakness is observed in children from around 4 to 5 years old. Then, muscle weakness progresses to the loss of ambulation by about 12 years old and death due to cardiac or respiratory insufficiency in the twenties. DMD is such a severe disorder. At present, there is no effective therapy for DMD available, and it has been strongly desired to develop a novel therapeutic agent.

DMD is known to be caused by a mutation in the dystrophin gene. The dystrophin gene is located on X chromosome and is a huge gene consisting of 2.2 million DNA nucleotide pairs. DNA is transcribed into mRNA precursors, and introns are removed by splicing to synthesize mRNA in which 79 exons are joined together. This mRNA is translated into 3,685 amino acids to produce the dystrophin protein. The dystrophin protein is associated with the maintenance of membrane stability in muscle cells and necessary to make muscle cells less fragile. The dystrophin gene from patients with DMD contains a mutation and hence, the dystrophin protein, which is functional in muscle cells, is rarely expressed. Therefore, the structure of muscle cells cannot be maintained in the body of the patients with DMD, leading to a large influx of calcium ions into muscle cells. Consequently, an inflammation-like response occurs to promote fibrosis so that muscle cells can be regenerated only with difficulty.

Becker muscular dystrophy (BMD) is also caused by a mutation in the dystrophin gene. The symptoms involve muscle weakness accompanied by atrophy of muscle but are typically mild and slow in the progress of muscle weakness, when compared to DMD. In many cases, its onset is in adulthood. Differences in clinical symptoms between DMD and BMD are considered to reside in whether the reading frame for amino acids on the translation of dystrophin mRNA into the dystrophin protein is disrupted by the mutation or not (Non-Patent Document 1). More specifically, in DMD, the presence of mutation shifts the amino acid reading frame so that the expression of functional dystrophin protein is abolished, whereas in BMD the dystrophin protein that functions, though imperfectly, is produced because the amino acid reading frame is preserved, while a part of the exons are deleted by the mutation.

Exon skipping is expected to serve as a method for treating DMD. This method involves modifying splicing to restore the amino acid reading frame of dystrophin mRNA and induce expression of the dystrophin protein having the function partially restored (Non-Patent Document 2). The amino acid sequence part, which is a target for exon skipping, will be lost. For this reason, the dystrophin protein expressed by this treatment becomes shorter than normal one but since the amino acid reading frame is maintained, the function to stabilize muscle cells is partially retained. Consequently, it is expected that exon skipping will lead DMD to the similar symptoms to that of BMD which is milder. The exon skipping approach has passed the animal tests using mice or dogs and now is currently assessed in clinical trials on human DMD patients.

The skipping of an exon can be induced by binding of antisense nucleic acids targeting either 5' or 3' splice site or both sites, or exon-internal sites. An exon will only be included in the mRNA when both splice sites thereof are recognized by the spliceo-some complex. Thus, exon skipping can be induced by targeting the splice sites with antisense nucleic acids. Furthermore, the binding of an SR protein to an exonic splicing enhancer (ESE) is considered necessary for an exon to be recognized by the splicing mechanism. Accordingly, exon skipping can also be induced by targeting ESE.

Since a mutation of the dystrophin gene may vary depending on DMD patients, antisense nucleic acids need to be designed based on the site or type of respective genetic mutation. In the past, antisense nucleic acids that induce exon skipping for all 79 exons were produced by Steve Wilton, et al., University of Western Australia (Non-Patent Document 3), and the antisense nucleic acids which induce exon skipping for 39 exons were produced by Annemieke Aartsma-Rus, et al., Netherlands (Non-Patent Document 4).

It is considered that approximately 20% of all DMD patients may be treated by skipping the 55th, the 45th, the 50th and the 44th exons (hereinafter referred to as "exon 55", "exon 45", "exon 50" and "exon 44", respectively). In recent years, several research organizations reported on the studies where exon 55, 45, 50 or 44 in the dystrophin gene was targeted for exon skipping (Patent Documents 1 to 8). However, a technique for skipping exon 55, 45, 50 or 44 with a high efficiency has not yet been established.

Patent Document 1: International Publication WO 2006/000057
Patent Document 2: International Publication WO 2004/048570
Patent Document 3: US Unexamined Patent Application Publication US 2010/0168212
Patent Document 4: International Publication WO2010/048586
Patent Document 5: International Publication WO 2004/083446
Patent Document 6: International Publication WO 2010/050801
Patent Document 7: International Publication WO 2009/139630
Non-Patent Document 1: Monaco A. P. et al., Genomics 1988; 2: p. 90-95

Non-Patent Document 2: Matsuo M., Brain Dev 1996; 18: p. 167-172

Non-Patent Document 3: Wilton S. D., et al., Molecular Therapy 2007: 15: p. 1288-96

Non-Patent Document 4: Annemieke Aartsma-Rus et al. (2002) Neuromuscular Disorders 12: S71-S77

Non-Patent Document 5: Linda J. Popplewell et al., (2010) Neuromuscular Disorders, vol. 20, no. 2, p. 102-10

DISCLOSURE OF THE INVENTION

Under the foregoing circumstances, antisense oligomers that strongly induce skipping of exon 55, exon 45, exon 50 or exon 44 in the dystrophin gene and muscular dystrophy therapeutics comprising oligomers thereof have been desired.

As a result of detailed studies of the structure of the dystrophin gene, the present inventors have found that exon 55 skipping can be induced with a high efficiency by antisense oligomers which target the sequence consisting of around the 1st to the 21st, the 11th to the 31st, and the 14th to the 34th nucleotides from the 5' end of exon 55 in the mRNA precursor (hereinafter referred to as "pre-mRNA") in the dystrophin gene with antisense oligomers.

The present inventors have also found that exon 45 skipping can be induced with a high efficiency by antisense oligomers which target the sequence consisting of around the 1st to the 25th and the 6th to the 30th nucleotides from the 5' end of exon 45 in the pre-mRNA in the dystrophin gene with antisense oligomers.

Furthermore, the present inventors have found that exon 50 skipping can be induced with a high efficiency by antisense oligomers which target the sequence consisting of around the 107th to the 127th nucleotides from the 5' end of exon 50 in the pre-mRNA in the dystrophin gene with antisense oligomers.

Additionally, the present inventors have also found that exon 44 skipping can be induced with a high efficiency by antisense oligomers which target the sequence consisting of around the 11th to the 32nd and the 26th to the 47th nucleotides from the 5' end of exon 44 in the pre-mRNA in the dystrophin gene with antisense oligomers.

Based on this finding, the present inventors have accomplished the present invention.

That is, the present invention is as follows.

[1] An antisense oligomer which causes skipping of the 55th exon in the human dystrophin gene, consisting of a nucleotide sequence complementary to any one of the nucleotide sequences consisting of the −2nd to the 19th, the −2nd to the 20th, the −2nd to the 21st, the −2nd to the 22nd, the −2nd to the 23rd, the −1st to the 19th, the −1st to the 20th, the −1st to the 21st, the −1st to the 22nd, the −1st to the 23rd, the 1st to the 19th, the 1st to the 20th, the 1st to the 21st, the 1st to the 22nd, the 1st to the 23rd, the 2nd to the 19th, the 2nd to the 20th, the 2nd to the 21st, the 2nd to the 22nd, the 2nd to the 23rd, the 3rd to the 19th, the 3rd to the 20th, the 3rd to the 21st, the 3rd to the 22nd, the 3rd to the 23rd, the 9th to the 29th, the 9th to the 30th, the 9th to the 31st, the 9th to the 32nd, the 9th to the 33rd, the 10th to the 29th, the 10th to the 30th, the 10th to the 31st, the 10th to the 32nd, the 10th to the 33rd, the 11th to the 29th, the 11th to the 30th, the 11th to the 31st, the 11th to the 32nd, the 11th to the 33rd, the 12th to the 29th, the 12th to the 30th, the 12th to the 31st, the 12th to the 32nd, the 12th to the 33rd, the 13th to the 29th, the 13th to the 30th, the 13th to the 31st, the 13th to the 32nd, the 13th to the 33rd, the 12th to the 34th, the 12th to the 35th, the 12th to the 36th, the 13th to the 34th, the 13th to the 35th, the 13th to the 36th, the 14th to the 32nd, the 14th to the 33rd, the 14th to the 34th, 14th to the 35th, the 14th to the 36th, the 15th to the 32nd, the 15th to the 33rd, the 15th to the 34th, the 15th to the 35th, the 15th to the 36th, the 16th to the 32nd, the 16th to the 33rd, the 16th to the 34th, the 16th to the 35th, or the 16th to the 36th nucleotides, from the 5' end of the 55th exon in the human dystrophin gene.

[2] An antisense oligomer which causes skipping of the 45th exon in the human dystrophin gene, consisting of a nucleotide sequence complementary to any one of the nucleotide sequences consisting of the −3rd to the 19th, the −3rd to the 20th, the −3rd to the 21st, the −3rd to the 22nd, the −3rd to the 23rd, the −2nd to the 19th, the −2nd to the 20th, the −2nd to the 21st, the −2nd to the 22nd, the −2nd to the 23rd, the −1st to the 19th, the −1st to the 20th, the −1st to the 21st, the −1st to the 22nd, the −1st to the 23rd, the 1st to the 19th, the 1st to the 20th, the 1st to the 21st, the 1st to the 22nd, the 1st to the 23rd, the 2nd to the 19th, the 2nd to the 20th, the 2nd to the 21st, the 2nd to the 22nd, the 2nd to the 23rd, the −2nd to the 24th, the −2nd to the 25th, the −2nd to the 26th, the −2nd to the 27th, the −1st to the 24th, the −1st to the 25th, the −1st to the 26th, the −1st to the 27th, the 1st to the 24th, the 1st to the 25th, the 1st to the 26th, the 1st to the 27th, the 2nd to the 24th, the 2nd to the 25th, the 2nd to the 26th, the 2nd to the 27th, the 3rd to the 23rd, the 3rd to the 24th, the 3rd to the 25th, the 3rd to the 26th, the 3rd to the 27th, the 4th to the 28th, the 4th to the 29th, the 4th to the 30th, the 4th to the 31st, the 4th to the 32nd, the 5th to the 28th, the 5th to the 29th, the 5th to the 30th, the 5th to the 31st, the 5th to the 32nd, the 6th to the 28th, the 6th to the 29th, the 6th to the 30th, the 6th to the 31st, the 6th to the 32nd, the 7th to the 28th, the 7th to the 29th, the 7th to the 30th, the 7th to the 31st, the 7th to the 32nd, the 8th to the 28th, the 8th to the 29th, the 8th to the 30th, the 8th to the 31st, or the 8th to the 32nd nucleotides, from the 5' end of the 45th exon in the human dystrophin gene.

[3] An antisense oligomer which causes skipping of the 50th exon in the human dystrophin gene, consisting of a nucleotide sequence complementary to any one of the nucleotide sequences consisting of the 105th to the 125th, the 105th to the 126th, the 105th to the 127th, the 105th to the 128th, the 105th to the 129th, the 106th to the 125th, the 106th to the 126th, the 106th to the 127th, the 106th to the 128th, the 106th to the 129th, the 107th to the 125th, the 107th to the 126th, the 107th to the 127th, the 107th to the 128th, the 107th to the 129th, the 108th to the 125th, the 108th to the 126th, the 108th to the 127th, the 108th to the 128th, the 108th to the 129th, the 109th to the 125th, the 109th to the 126th, the 109th to the 127th, the 109th to the 128th, or the 109th to the 129th nucleotides, from the 5' end of the 50th exon in the human dystrophin gene.

[4] An antisense oligomer which causes skipping of the 44th exon in the human dystrophin gene, consisting of a nucleotide sequence complementary to any one of the nucleotide sequences consisting of the 9th to the 30th, 9th to the 31st, the 9th to the 32nd, the 9th to the 33rd, 9th to the 34th, the 10th to the 30th, the 10th to the 31st, the 10th to the 32nd, the 10th to the 33rd, the 10th to the 34th, the 11th to the 30th, the 11th to the 31st, the 11th to the 32nd, the 11th to the 33rd, the 11th to the 34th, the 12th to the 30th, the 12th to the 31st, the 12th to the 32nd, the 12th to the 33rd, the 12th to the 34th, the 13th to the 30th, the 13th to the 31st, the 13th to the 32nd, the 13th to the 33rd, the 13th to the 34th, the 24th to the 45th, the 24th to the 46th, the 24th to the 47th, the 24th to the 48th, the 24th to the 49th, the 25th to the 45th, the 25th to the 46th, the 25th to the 47th, the 25th to the 48th, the 25th to the 49th, the 26th to the 45th, the 26th to the 46th, the 26th to the 47th, the 26th to the 48th, the 26th to the 49th, the 27th to the 45th, the 27th to the 46th, the 27th to the 47th, the 27th to the 48th, the 27th to the 49th, the 28th to the 45th, the 28th to the 46th, the 28th to the 47th, the 28th to the 48th, the 28th to the 49th, the 29th to the 45th, the 29th to the 46th, the 29th to the 47th, the 29th to the 48th, or the 29th to the 49th nucleotides, from the 5' end of the 44th exon in the human dystrophin gene.

[5] The antisense oligomer according to [1], which consists of a complementary sequence to the nucleotide sequences consisting of the 1st to the 21st, the 11th to the 31st, or the 14th to the 34th nucleotides, from the 5' end of the 55th exon in the human dystrophin gene.

[6] The antisense oligomer according to [1], consisting of the nucleotide sequence shown by any one selected from the group consisting of the 170th to the 190th, the 160th to the 180th, and the 157th to the 177th nucleotides of SEQ ID NO: 5.

[7] The antisense oligomer according to [2], which consists of a complementary sequence to the nucleotide sequences consisting of the −2nd to the 19th, the 1st to the 21st, the 1st to the 25th, or the 6th to the 30th nucleotides, from the 5' end of the 45th exon in the human dystrophin gene.

[8] The antisense oligomer according to [2], consisting of the nucleotide sequence shown by any one selected from the group consisting of the 158th to the 178th, the 156th to the 176th, the 152nd to the 176th, and the 147th to the 171st nucleotides of SEQ ID NO: 6.

[9] The antisense oligomer according to [3], which consists of a complementary sequence to the nucleotide sequences consisting of the 106th to the 126th or the 107th to the 127th nucleotides, from the 5' end of the 50th exon in the human dystrophin gene.

[10] The antisense oligomer according to [3], consisting of the nucleotide sequence shown by any one selected from the group consisting of the 4th to the 24th and the 3rd to the 23rd nucleotides of SEQ ID NO: 7.

[11] The antisense oligomer according to [4], which consists of a complementary sequence to the nucleotide sequences consisting of the 11th to the 32nd, the 25th to the 45th, the 26th to the 46th, the 26th to the 47th or the 27th to the 47th nucleotides, from the 5' end of the 44th exon in the human dystrophin gene.

[12] The antisense oligomer according to [4], consisting of the nucleotide sequence shown by any one selected from the group consisting of the 117th to the 138th, the 104th to the 124th, the 103rd to the 123rd, the 102nd to the 123rd and the 102nd to the 122nd nucleotides of SEQ ID NO: 8.

[13] The antisense oligomer according to any one of [1] to [12], which is an oligonucleotide.

[14] The antisense oligomer according to [13], wherein the sugar moiety and/or the phosphate-binding region of at least one nucleotide constituting the oligonucleotide is modified.

[15] The antisense oligomer according to [14], wherein the sugar moiety of at least one nucleotide constituting the oligonucleotide is a ribose in which the 2'-OH group is replaced by any one selected from the group consisting of OR, R, R'OR, SH, SR, $NH_2$, NHR, $NR_2$, $N_3$, CN, F, Cl, Br and I (wherein R is an alkyl or an aryl and R' is an alkylene).

[16] The antisense oligomer according to [14] or [15], wherein the phosphate-binding region of at least one nucleotide constituting the oligonucleotide is any one selected from the group consisting of a phosphorothioate bond, a phosphorodithioate bond, an alkylphosphonate bond, a phosphoramidate bond and a boranophosphate bond.

[17] The antisense oligomer according to any one of [1] to [12], which is a morpholino oligomer.

[18] The antisense oligomer according to [17], which is a phosphorodiamidate morpholino oligomer.

[19] The antisense oligomer according to [17] or [18], wherein the 5' end is any one of the groups of chemical formulae (1) to (3) below:

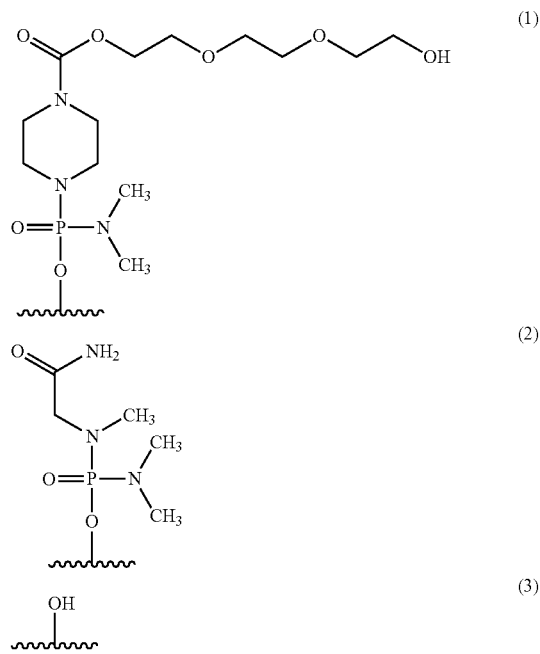

[20] A pharmaceutical composition for the treatment of muscular dystrophy, comprising as an active ingredient the antisense oligomer according to any one of [1] to [19], or a pharmaceutically acceptable salt or hydrate thereof.

The antisense oligomer of the present invention can induce skipping of exon 55, exon 45, exon 50 or exon 44 in the human dystrophin gene with high efficiencies. Also, the symptoms of Duchenne muscular dystrophy can be effectively alleviated by administering the pharmaceutical composition of the present invention. In addition, since the antisense oligomer of the present invention targets only exon sequences in patients, the target sequences are conserved among individuals compared to the cases with those targeting sequences in introns. Therefore, the antisense oligomer of the present invention is capable of achieving excellent skipping efficiencies regardless of individual varieties (personal differences). Furthermore, the antisense oligomer of the present invention has short length of 20 bp or around and has less probability of containing mutations raised from individual varieties (interpersonality) e.g. SNP (Single Nucleotide Polymorphism) in the target sequences compared to conventional antisense oligomers for DMD treatment having lengths of 25 bp or so. This feature also helps the antisense oligomer of the present invention in achieving excellent skipping efficiencies regardless of individual variety (personal differences). Moreover, the antisense oligomer of the present invention have less side effects raised by the induction of cytokines and so on, since antisense oligomers having shorter chains have less tendency to induce immunity in general.

Also, since the antisense oligomer of the present invention is rather short, the cost of manufacturing is relatively small.

BEST MODE FOR CARRYING OUT THE INVENTION

Figure 1:
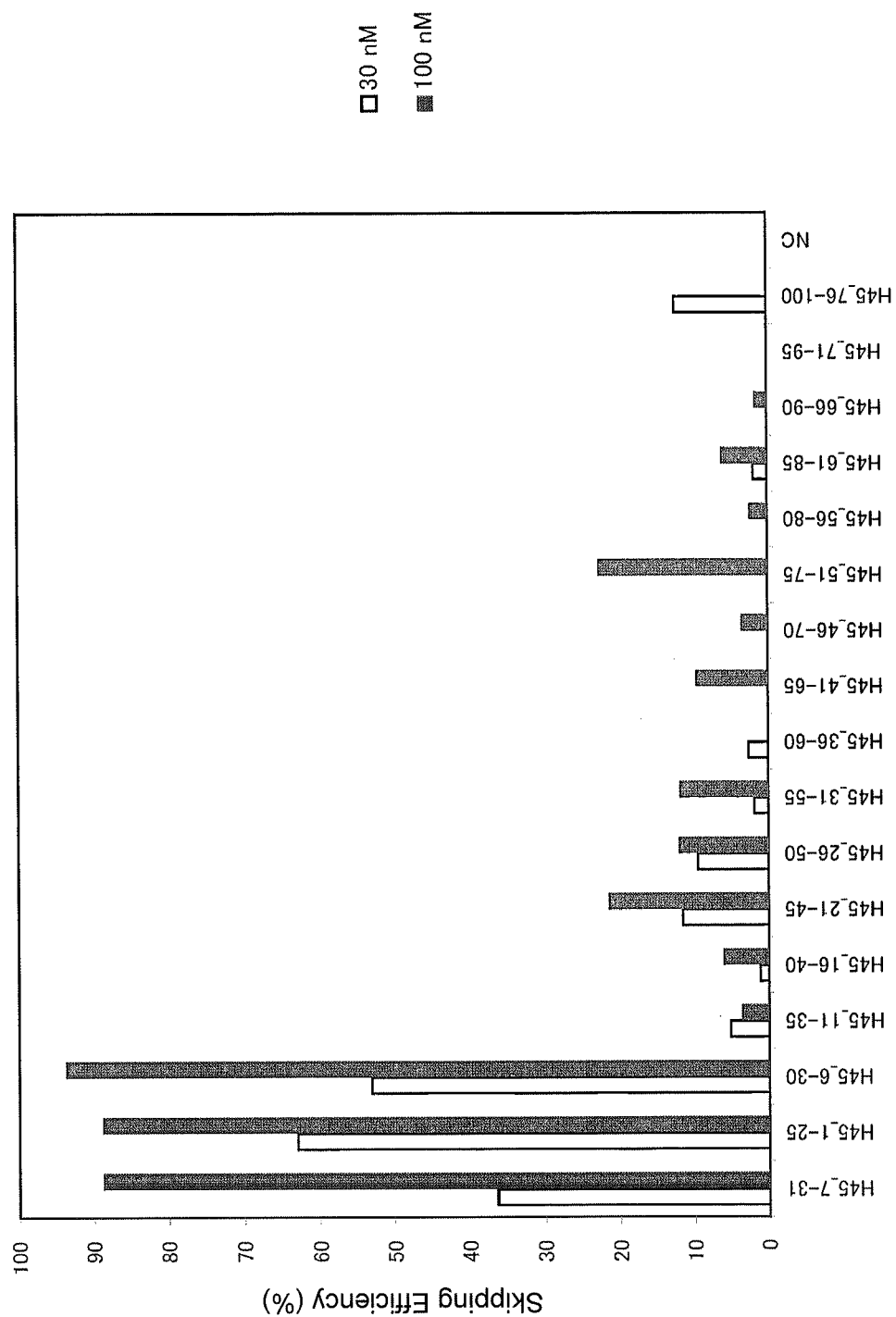
FIG. 1 shows the efficiency of exon 45 skipping by 2'-OMe-S-RNA oligomer in the human dystrophin gene in human rhabdomyosarcoma cell line (RD cells).

Hereinafter, the present invention is described in detail. The embodiments described below are intended to be presented by way of example merely to describe the invention but not limited only to the following embodiments. The present invention may be implemented in various ways without departing from the gist of the invention.

All of the publications, published patent applications, patents and other patent documents cited in the specification are herein incorporated by reference in their entirety. The specification hereby incorporates by reference the contents of the specification and drawings in the Japanese Patent Application (No. 2011-288040) filed Dec. 28, 2011 and the Japanese Patent Application (No. 2012-043092) filed Feb. 29, 2012, from which the priority was claimed.

Hereinafter, the present invention is described in detail. The embodiments described below are intended to be presented by way of example merely to describe the invention but not limited only to the following embodiments. The present invention may be implemented in various ways without departing from the gist of the invention.

Without description in particular, the amino acid sequence represents the amino terminus as left and carboxyl terminus as right, and the base sequence represents the 5' end as left and the 3' end as right.

1. Antisense Oligomer

The present invention provides the antisense oligomer (hereinafter referred to as the "exon 55 skipping oligomer of the present invention") which causes skipping of exon 55 in the human dystrophin gene, consisting of a nucleotide sequence complementary to any one of the nucleotide sequences (hereinafter also referred to as the "exon 55 target sequence") consisting of the −2nd to the 19th, the −2 nd to the 20th, the −2nd to the 21st, the −2nd to the 22nd, the −2nd to the 23rd, the −1st to the 19th, the −1st to the 20th, the −1st to the 21st, the −1st to the 22nd, the −1st to the 23rd, the 1st to the 19th, the 1st to the 20th, the 1st to the 21st, the 1st to the 22nd, the 1st to the 23rd, the 2nd to the 19th, the 2nd to the 20th, the 2nd to the 21st, the 2nd to the 22nd, the 2nd to the 23rd, the 3rd to the 19th, the 3rd to the 20th, the 3rd to the 21st, the 3rd to the 22nd, the 3rd to the 23rd, the 9th to the 29th, the 9th to the 30th, the 9th to the 31st, the 9th to the 32nd, the 9th to the 33rd, the 10th to the 29th, the 10th to the 30th, the 10th to the 31st, the 10th to the 32nd, the 10th to the 33rd, the 11th to the 29th, the 11th to the 30th, the 11th to the 31st, the 11th to the 32nd, the 11th to the 33rd, the 12th to the 29th, the 12th to the 30th, the 12th to the 31st, the 12th to the 32nd, the 12th to the 33rd, the 13th to the 29th, the 13th to the 30th, the 13th to the 31st, the 13th to the 32nd, the 13th to the 33rd, the 12th to the 34th, the 12th to the 35th, the 12th to the 36th, the 13th to the 34th, the 13th to the 35th, the 13th to the 36th, the 14th to the 32nd, the 14th to the 33rd, the 14th to the 34th, the 14th to the 35th, the 14th to the 36th, the 15th to the 32nd, the 15th to the 33rd, the 15th to the 34th, the 15th to the 35th, the 15th to the 36th, the 16th to the 32nd, the 16th to the 33rd, the 16th to the 34th, the 16th to the 35th, or the 16th to the 36th nucleotides, from the 5' end of exon 55 in the human dystrophin gene.

The present invention also provides the antisense oligomer (hereinafter referred to as the "exon 45 skipping oligomer of the present invention") which causes skipping of exon 45 in the human dystrophin gene, consisting of a nucleotide sequence complementary to any one of the nucleotide sequences (hereinafter also referred to as the "exon 45 target sequence") consisting of the −3rd to the 19th, the −3rd to the 20th, the −3rd to the 21st, the −3rd to the 22nd, the −3rd to the 23rd, the −2nd to the 19th, the −2nd to the 20th, the −2nd to the 21st, the −2nd to the 22nd, the −2nd to the 23rd, the −1st to the 19th, the −1st to the 20th, the −1st to the 21st, the −1st to the 22nd, the −1st to the 23rd, the 1st to the 19th, the 1st to the 20th, the 1st to the 21st, the 1st to the 22th, the 1st to the 23rd, the 2nd to the 19th, the 2nd to the 20th, the 2nd to the 21st, the 2nd to the 22nd, the 2nd to the 23rd, the −2nd to the 24th, the −2 nd to the 25th, the −2nd to the 26th, the −2nd to the 27th, the −1st to the 24th, the −1st to the 25th, the −1st to the 26th, the −1st to the 27th, the 1st to the 24th, the 1st to the 25th, the 1st to the 26th, the 1st to the 27th, the 2nd to the 24th, the 2nd to the 25th, the 2nd to the 26th, the 2nd to the 27th, the 3rd to the 23rd, the 3rd to the 24th, the 3rd to the 25th, the 3rd to the 26th, the 3rd to the 27th, the 4th to the 28th, the 4th to the 29th, the 4th to the 30th, the 4th to the 31th, the 4th to the 32nd, the 5th to the 28th, the 5th to the 29th, the 5th to the 30th, the 5th to the 31st, the 5th to the 32nd, the 6th to the 28th, the 6th to the 29th, the 6th to the 30th, the 6th to the 31st, the 6th to the 32nd, the 7th to the 28th, the 7th to the 29th, the 7th to the 30th, the 7th to the 31st, the 7th to the 32nd, the 8th to the 28th, the 8th to the 29th, the 8th to the 30th, the 8th to the 31st, or the 8th to the 32nd nucleotides, from the 5' end of exon 45 in the human dystrophin gene.

Additionally, the present invention provides the antisense oligomer (hereinafter referred to as the "exon 50 skipping oligomer of the present invention") which causes skipping of exon 50 in the human dystrophin gene, consisting of a nucleotide sequence complementary to any one of the nucleotide sequences (hereinafter also referred to as the "exon 50 target sequence") consisting of the 105th to the 125th, the 105th to the 126th, the 105th to the 127th, the 105th to the 128th, the 105th to the 129th, the 106th to the 125th, the 106th to the 126th, the 106th o the 127th, the 106th to the 128th, the 106th to the 129th, the 107th to the 125th, the 107th to the 126th, the 107th to the 127th, the 107th to the 128th, the 107th to the 129th, the 108th to the 125th, the 108th to the 126th, the 108th to the 127th, the 108th to the 128th, the 108th to the 129th, the 109th to the 125th, the 109th to the 126th, the 109th to the 127th, the 109th to the 128th, or the 109th to the 129th nucleotides, from the 5' end of exon 50 in the human dystrophin gene.

Furthermore, the present invention provides the antisense oligomer (hereinafter referred to as the "exon 44 skipping oligomer of the present invention") which causes skipping of exon 44 in the human dystrophin gene, consisting of a nucleotide sequence complementary to any one of the nucleotide sequences (hereinafter also referred to as the "exon 44 target sequence") consisting of the 9th to the 30th, the 9th to the 31st, the 9th to the 32nd, the 9th to the 33rd, the 9th to the 34th, the 10th to the 30th, the 10th to the 31st, the 10th to the 32nd, the 10th to the 33rd, the 10th to the 34th, the 11th to the 30th, the 11th to the 31st, the 11th to the 32nd, the 11th to the 33rd, the 11th to the 34th, the 12th to the 30th, the 12th to the 31st, the 12th to the 32nd, the 12th to the 33rd, the 12th to the 34th, the 13th to the 30th, the 13th to the 31st, the 13th to the 32nd, the 13th to the 33rd, the 13th to the 34th, the 24th to the 45th, the 24th to the 46th, the 24th to the 47th, the 24th to the 48th, the 24th to the 49th, the 25th to the 45th, the 25th to the 46th, the 25th to the 47th, the 25th to the 48th, the 25th to the 49th, the 26th to the 45th, the 26th to the 46th, the 26th to the 47th, the 26th to the 48th, the 26th to the 49th, the 27th to the 45th, the 27th to the 46th, the 27th to the 47th, the 27th to the 48th, the 27th to the 49th, the 28th to the 45th, the 28th to the 46th, the 28th to the 47th, the 27th to the 48th, the 27th to the 49th, the 28th to the 45th, the 28th to the 46th, the 28th to the 47th, the 28th to the 48th, the 28th to the 49th, the 29th to the 45th, the 29th to the 46th, the 29th to the 47th, the 29th to the 48th, or the 29th to the 49th nucleotides, from the 5' end of exon 44 in the human dystrophin gene.

Hereinafter, the skipping oligomers of exon 55, 45, 50 and 44 may be collectively referred to as the "oligomers of the present invention".

[Exon 55, 45, 50 and 44 in Human Dystrophin Gene]

In the present invention, the term "gene" is intended to mean a genomic gene and also include cDNA, mRNA precursor and mRNA. Preferably, the gene is mRNA precursor, i.e. pre-mRNA.

In the human genome, the human dystrophin gene locates at locus Xp21.2. The human dystrophin gene has a size of 3.0 Mbp and is the largest gene among known human genes. However, the coding regions of the human dystrophin gene are only 14 kb, distributed as 79 exons throughout the human dystrophin gene (Roberts, R G, et al., Genomics, 16: 536-538 (1993)). The pre-mRNA, which is the transcript of the human dystrophin gene, undergoes splicing to generate mature mRNA of 14 kb. The nucleotide sequence of human wild-type dystrophin gene is known (GeneBank Accession No. NM_004006).

The nucleotide sequence consisting of the −2nd to the 190th nucleotides, from the 5' end of exon 55 in the human wild-type dystrophin gene is represented by SEQ ID NO: 1. The nucleotide sequence consisting of the −3rd to the 176th nucleotides, from the 5' end of exon 45 in the human wild-type dystrophin gene is represented by SEQ ID NO: 2. The nucleotide sequence consisting of the 1st to the 109th nucleotides, from the 5' end of exon 50 and the 1st to the 20th nucleotides, from the 5' end of intron 50 in the human wild-type dystrophin gene is represented by SEQ ID NO: 3.

The nucleotide sequence consisting of the 1st to the 148th nucleotides, from the 5' end of exon 44 in the human wild-type dystrophin gene is represented by SEQ ID NO: 4.

The oligomer of the present invention is designed to cause skipping of exon 55, 45, 50 or 44 in the human dystrophin gene, thereby modifying the protein encoded by DMD type of dystrophin gene into the BMD type of dystrophin protein. Accordingly, exon 55, 45, 50 and 44 in the dystrophin gene that are the targets of exon skipping by the oligomer of the present invention include both wild and mutant types.

Specifically, exon 55, 45, 50 and 44 mutants of the human dystrophin gene are the polynucleotides defined in (a) or (b) below.

(a) A polynucleotide that hybridizes under stringent conditions to a polynucleotide consisting of a nucleotide sequence complementary to the nucleotide sequence of SEQ ID NO: 1 (or a nucleotide sequence consisting of the 3rd to the 192nd nucleotides of SEQ ID NO:1), SEQ ID NO: 2 (or a nucleotide sequence consisting of the 4th to the 179th nucleotides of SEQ ID NO:2), SEQ ID NO: 3 (or a nucleotide sequence consisting of the 1st to the 109th nucleotides of SEQ ID NO:3), or SEQ ID NO: 4;

(b) A polynucleotide consisting of a nucleotide sequence having at least 90% homology with the nucleotide sequence of SEQ ID NO:1 (or a nucleotide sequence consisting of the 3rd to the 192nd nucleotides of SEQ ID NO:1), SEQ ID NO: 2 (or a nucleotide sequence consisting of the 4th to the 179th nucleotides of SEQ ID NO:2), SEQ ID NO: 3 (or a nucleotide sequence consisting of the 1st to the 109th nucleotides of SEQ ID NO:3), or SEQ ID NO: 4.

As used herein, the term "polynucleotide" is intended to mean DNA or RNA.

As used herein, the term "polynucleotide that hybridizes under stringent conditions" refers to, for example, a polynucleotide obtained by colony hybridization, plaque hybridization, Southern hybridization or the like, using as a probe all or part of a polynucleotide consisting of a nucleotide sequence complementary to the nucleotide sequence of SEQ ID NO: 1 (or a nucleotide sequence consisting of the 3rd to the 192nd nucleotides of SEQ ID NO:1), SEQ ID NO: 2 (or a nucleotide sequence consisting of the 4th to the 179th nucleotides of SEQ ID NO:2), SEQ ID NO: 3 (or a nucleotide sequence consisting of the 1st to the 109th nucleotides of SEQ ID NO:3), or SEQ ID NO: 4. The hybridization method which may be used includes methods described in, for example, "Sambrook & Russell, Molecular Cloning: A Laboratory Manual Vol. 3, Cold Spring Harbor, Laboratory Press 2001," "Ausubel, Current Protocols in Molecular Biology, John Wiley & Sons 1987-1997," etc.

As used herein, the term "complementary nucleotide sequence" is not limited only to nucleotide sequences that form Watson-Crick pairs with target nucleotide sequences, but is intended to also include nucleotide sequences which form Wobble base pairs. As used herein, the term Watson-Crick pair refers to a pair of nucleobases in which hydrogen bonds are formed between adenine-thymine, adenine-uracil or guanine-cytosine, and the term Wobble base pair refers to a pair of nucleobases in which hydrogen bonds are formed between guanine-uracil, inosine-uracil, inosine-adenine or inosine-cytosine. As used herein, the term "complementary nucleotide sequence" does not only refers to a nucleotide sequence 100% complementary to the target nucleotide sequence but also refers to a complementary nucleotide sequence that may contain, for example, 1 to 3, 1 to 2, or one nucleotide non-complementary to the target nucleotide sequence.

As used herein, the term "stringent conditions" may be any of low stringent conditions, moderate stringent conditions or high stringent conditions. The term "low stringent condition" is, for example, 5×SSC, 5×Denhardt's solution, 0.5% SDS, 50% formamide at 32° C. The term "moderate stringent condition" is, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent condition" is, for example, 5×SSC, 5×Denhardt's solution, 0.5% SDS, 50% formamide at 50° C. or 0.2×SSC, 0.1% SDS at 65° C. Under these conditions, polynucleotides with higher homology are expected to be obtained efficiently at higher temperatures, although multiple factors are involved in hybridization stringency including temperature, probe concentration, probe length, ionic strength, time, salt concentration and others, and those skilled in the art may approximately select these factors to achieve similar stringency.

When commercially available kits are used for hybridization, for example, an Alkphos Direct Labelling and Detection System (GE Healthcare) may be used. In this case, according to the attached protocol, after cultivation with a labeled probe overnight, the membrane is washed with a primary wash buffer containing 0.1% (w/v) SDS at 55° C., thereby detecting hybridized polynucleotides. Alternatively, when the probe is labeled with digoxigenin (DIG) using a commercially available reagent (e.g., a PCR Labelling Mix (Roche Diagnostics), etc.) in producing a probe based on all or part of the complementary sequence to the nucleotide sequence of SEQ ID NO: 1 (or a nucleotide sequence consisting of the 3rd to the 192nd nucleotides of SEQ ID NO:1), SEQ ID NO: 2 (or a nucleotide sequence consisting of the 4th to the 179th nucleotides of SEQ ID NO:2), SEQ ID NO: 3 (or a nucleotide sequence consisting of the 1st to the 109th nucleotides of SEQ ID NO:3), or SEQ ID NO: 4, hybridization can be detected with a DIG Nucleic Acid Detection Kit (Roche Diagnostics).

In addition to the polynucleotides described above, other polynucleotides that can be hybridized include polynucleotides having 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, 99.9% or higher identity with the polynucleotide of SEQ ID NO: 1 (or a nucleotide sequence consisting of the 3rd to the 192nd nucleotides of SEQ ID NO:1), SEQ ID NO: 2 (or a nucleotide sequence consisting of the 4th to the 179th nucleotides of SEQ ID NO:2), SEQ ID NO: 3 (or a nucleotide sequence consisting of the 1st to the 109th nucleotides of SEQ ID NO:3), or SEQ ID NO: 4, as calculated by homology search software BLAST using the default parameters.

The identity between nucleotide sequences may be determined using algorithm BLAST (Basic Local Alignment Search Tool) by Karlin and Altschul (Proc. Natl. Acad. Sci. USA 872264-2268, 1990; Proc. Natl. Acad. Sci. USA 90: 5873, 1993). Programs called BLASTN and BLASTX based on the BLAST algorithm have been developed (Altschul S F, et al: J. Mol. Biol. 215: 403, 1990). When a nucleotide sequence is sequenced using BLASTN, the parameters are, for example, score=100 and word-length=12. When BLAST and Gapped BLAST programs are used, the default parameters for each program are employed.

The sequence complementary to the nucleotide sequence consisting of the −2nd to the 190th nucleotides from the 5' end of exon 55 is represented by SEQ ID NO: 5. Herein, the nucleotide sequence consisting of the −2nd to the −1st nucleotides, from the 5' end of exon 55 (the nucleotide sequence consisting of the 1st to the 2nd nucleotides of SEQ ID NO: 1) represents nucleotide sequence consisting of 2 nucleotides at the most 3' end downstream of intron 54 which is located between exon 54 and exon 55. More specifically, the nucleotide sequence of exon 55 is one consisting of the 3rd to the 192nd nucleotides of SEQ ID NO: 1 and the sequence complementary to exon 55 is one consisting of the 1st to the 190th nucleotides of SEQ ID NO: 5.

Herein, the complementary sequence to the nucleotide sequences consisting of the −2nd to the 19th, the −2nd to the 20th, the −2nd to the 21st, the −2nd to the 22nd, the −2nd to the 23rd, the −1st to the 19th, the −1st to the 20th, the −1st to the 21st, the −1st to the 22nd, the −1st to the 23rd, the 1st to the 19th, the 1st to the 20th, the 1st to the 21st, the 1st to the 22nd, the 1st to the 23rd, the 2nd to the 19th, the 2nd to the 20th, the 2nd to the 21st, the 2nd to the 22nd, the 2nd to the 23rd, the 3rd to the 19th, the 3rd to the 20th, the 3rd to the 21st, the 3rd to the 22nd, the 3rd to the 23rd, the 9th to the 29th, the 9th to the 30th, the 9th to the 31st, the 9th to the 32nd, the 9th to the 33rd, the 10th to the 29th, the 10th to the 30th, the 10th to the 31st, the 10th to the 32nd, the 10th to the 33rd, the 11th to the 29th, the 11th to the 30th, the 11th to the 31st, the 11th to the 32nd, the 11th to the 33rd, the 12th to the 29th, the 12th to the 30th, the 12th to the 31st, the 12th to the 32nd, the 12th to the 33rd, the 13th to the 29th, the 13th to the 30th, the 13th to the 31st, the 13th to the 32nd, the 13th to the 33rd, the 12th to the 34th, the 12th to the 35th, the 12th to the 36th, the 13th to the 34th, the 13th to the 35th, the 13th to the 36th, the 14th to the 32nd, the 14th to the 33rd, the 14th to the 34th, the 14th to the 35th, the 14th to the 36th, the 15th to the 32nd, the 15th to the 33rd, the 15th to the 34th, the 15th to the 35th, the 15th to the 36th, the 16th to the 32nd, the 16th to the 33rd, the 16th to the 34th, the 16th to the 35th, or the 16th to the 36th nucleotides, from the 5' end of the 55th exon in the human dystrophin gene is respectively identical to the nucleotide sequence consisting of the 172nd to the 192nd, the 171st to the 192nd, the 170th to the 192nd, the 169th to the 192nd, the 168th to the 192nd, the 172nd to the 191st, the 171st to the 191st, the 170th to the 191st, the 169th to the 191st, the 168th to the 191st, the 172nd to the 190th, the 171st to the 190th, the 170th to the 190th, the 169th to the 190th, the 168th to the 190th, the 172nd to the 189th, the 171st to the 189th, the 170th to the 189th, the 169th to the 189th, the 168th to the 189th, the 172nd to the 188th, the 171st to the 188th, the 170th to the 188th, the 169th to the 188th, the 168th to the 188th, the 162nd to the 182nd, the 161st to the 182nd, the 160th to the 182nd, the 159th to the 182nd, the 158th to the 182nd, the 162nd to the 181st, the 161st to the 181st, the 160th to the 181st, the 159th to the 181st, the 158th to the 181st, the 162nd to the 180th, the 161st to the 180th, the 160th to the 180th, the 159th to the 180th, the 158th to the 180th, the 162nd to the 179th, the 161st to the 179th, the 160th to the 179th, the 159th to the 179th, the 158th to the 179th, the 162nd to the 178th, the 161st to the 178th, the 160th to the 178th, the 159th to the 178th, the 158th to the 178th, the 157th to the 179th, the 156th to the 179th, the 155th to 179th, the 157th to the 178th, the 156th to the 178th, the 155th to the 178th, the 159th to the 177th, the 158th to the 177th, the 157th to the 177th, the 156th to the 177th, the 155th to the 177th, the 159th to the 176th, the 158th to the 176th, the 157th to the 176th, the 156th to the 176th, the 155th to the 176th, the 159th to the 175th, the 158th to the 175th, the 157th to the 175th, the 156th to the 175th, or the 155th to the 175th nucleotides of SEQ ID NO: 5.

The complementary sequence to the nucleotide sequence consisting of the −3rd to the 176th nucleotides, from the 5' end of exon 45 is represented by SEQ ID NO: 6. Herein, the nucleotide sequence consisting of the −3rd to the −1st nucleotides, from the 5' end of exon 45 (the nucleotide sequence consisting of the 1st to the 3rd nucleotides of SEQ ID NO: 2) represents the nucleotide sequence consisting of 3 nucleotides at the most 3' end downstream of intron 44 which is located between exon 44 and exon 45. More specifically, the nucleotide sequence of exon 45 is the nucleotide sequence consisting of the 4th to the 179th nucleotides of SEQ ID NO: 2 and the complementary sequence to exon 45 is the nucleotide sequence consisting of the 1st to the 176th nucleotides of SEQ ID NO: 6.

Herein, the complementary sequence to the nucleotide sequences consisting of the −3rd to the 19th, the −3rd to the 20th, the −3rd to the 21st, the −3rd to the 22nd, the −3rd to the 23rd, the −2nd to the 19th, the −2nd to the 20th, the −2nd to the 21st, the −2nd to the 22nd, the −2nd to the 23rd, the −1st to the 19th, the −1st to the 20th, the −1st to the 21st, the −1st to the 22nd, −1st to the 23rd, the 1st to the 19th, the 1st to the 20th, the 1st to the 21st, the 1st to the 22nd, the 1st to the 23rd, the 2nd to the 19th, the 2nd to the 20th, the 2nd to the 21st, the 2nd to the 22nd, the 2nd to the 23rd, the −2nd to the 24th, the −2nd to the 25th, the −2nd to the 26th, the −2nd to the 27th, the −1st to the 24th, the −1st to the 25th, the −1st to the 26th, the −1st to the 27th, the 1st to the 24th, the 1st to the 25th, the 1st to the 26th, the 1st to the 27th, the 2nd to the $24^{th}$, the $2^{nd}$ to the $25^{th}$, the $2^{nd}$ to the $26^{th}$, the $2^{nd}$ to the $27^{th}$, the $3^{rd}$ to the $23^{rd}$, the $3^{rd}$ to the $24^{th}$, the $3^{rd}$ to the $25^{th}$, the $3^{rd}$ to the $26^{th}$, the $3^{rd}$ to the $27^{th}$, the $4^{th}$ to the $28^{th}$, the $4^{th}$ to the $29^{th}$, the $4^{th}$ to the $30^{th}$, the $4^{th}$ to the $31^{st}$, the $4^{th}$ to the $32^{nd}$, the $5^{th}$ to the $28^{th}$, the $5^{th}$ to the $29^{th}$, the $5^{th}$ to the $30^{th}$, the $5^{th}$ to the 31st, the $5^{th}$ to the $32^{nd}$, the 6th to the 28th, the 6th to the 29th, the 6th to the 30th, the 6th to the 31st, the 6th to the 32nd, the 7th to the 28th, the 7th to the 29th, the 7th to the 30th, the 7th to the 31st, the 7th to the 32nd, the 8th to the 28th, the 8th to the 29th, the 8th to the 30th, the 8th to the 31st, or the 8th to the 32nd nucleotides, from the 5' end of the 45th exon in the human dystrophin gene is respectively identical to the nucleotide sequence consisting of the 158th to the 179th, the 157th to the 179th, the 156th to the 179th, the 155th to the 179th, the 154th to the 179th, the 158th to the 178th, the 157th to the 178th, the 156th to the 178th, the 155th to the 178th, the 154th to the 178th, the 158th to the 177th, the 157th to the 177th, the 156th to the 177th, the 155th to the 177th, the 154th to the 177th, the 158th to the 176th, the 157th to the 176th, the 156th to the 176th, the 155th to the 176th, the 154th to the 176th, the 158th to the 175th, the 157th to the 175th, the 156th to the 175th, the 155th to the 175th, the 154th to the 175th, the 153rd to the 178th, the 152nd to the 178th, the 151st to the 178th, the 150th to the 178th, the 153rd to the 177th, the 152nd to the 177th, the 151st to the 177th, the 150th to the 177th, the 153rd to the 176th, the 152nd to the 176th, the 151st to the 176th, the 150th to the 176th, the 153rd to the 175th, the 152nd to the 175th, the 151st to the 175th, the 150th to the 175th, the 154th to the 174th, the 153rd to the 174th, the 152nd to the 174th, the 151st to the 174th, the 150th to the 174th, the 149th to the 173rd, the 148th to the 173rd, the 147th to the 173rd, the 146th to the 173rd, the 147th to the 173rd, the 149th to the 172nd, the 148th to the 172nd, the 147th to the 172nd, the 146th to the 172nd, the 145th to the 172nd, the 149th to the 171st, the 148th to the 171st, the 147th to the 171st, the 146th to the 171st, the 145th to the 171st, the 149th to the 170th, the 148th to the 170th, the 147th to the 170th, the 146th to the 170th, the 145th to the 170th, the 149th to the 169th, the 148th to the 169th, the 147th to the 169th, the 146th to the 169th or the 145th to the 169th nucleotides of SEQ ID NO: 6.

The complementary sequence to the nucleotide sequence consisting of the 1st to the 109th nucleotides, from the 5' end of exon 50, and the 1st to the 20th nucleotides, from the 5' end of intron 50, is represented by SEQ ID NO: 7. Herein, the nucleotide sequence consisting of the 1st to the 20th nucleotides, from the 5' end of intron 50 (the nucleotide sequence consisting of the 110th to the 129th nucleotides of SEQ ID NO: 3) is the nucleotide sequence consisting of 20 nucleotides at the most 5' end upstream of intron 50 which is located between exon 50 and exon 51. More specifically, the nucleotide sequence of exon 50 is the nucleotide sequence consisting of the 1st to the 109th nucleotides of SEQ ID NO: 3 and the complementary sequence to exon 50 is the nucleotide sequence consisting of the 21st to the 129th nucleotides of SEQ ID NO: 7.

Herein, the complementary sequence to the nucleotide sequences consisting of the 105th to the 125th, the 105th to the 126th, the 105th to the 127th, the 105th to the 128th, the 105th to the 129th, the 106th to the 125th, the 106th to the 126th, the 106th to the 127th, the 106th to the 128th, the 106th to the 129th, the 107th to the 125th, the 107th to the 126th, the 107th to the 127th, the 107th to the 128th, the 107th to the 129th, the 108th to the 125th, the 108th to the 126th, the 108th to the 127th, the 108th to the 128th, the 108th to the 129th, the 109th to the 125th, the 109th to the 126th, the 109th to the 127th, the 109th to the 128th or the 109th to the 129th nucleotides, from the 5' end of the 50th exon in the human dystrophin gene is respectively identical to the nucleotide sequence consisting of the 5th to the 25th, the 4th to the 25th, the 3rd to the 25th, the 2nd to the 25th, the 1st to the 25th, the 5th to the 24th, the 4th to the 24th, the 3rd to the 24th, the 2nd to the 24th, the 1st to the 24th, the 5th to the 23rd, the 4th to the 23rd, the 3rd to the 23rd, the 2nd to the 23rd, the 1st to the 23rd, the 5th to the 22nd, the 4th to the 22nd, the 3rd to the 22nd, the 2nd to the 22nd, the 1st to the 22nd, the 5th to the 21st, the 4th to the 21st, the 3rd to the 21st, the 2nd to the 21st or the 1st to the 21st nucleotides of SEQ ID NO: 7.

The complementary sequence to the nucleotide sequence consisting of the 1st to the 148th nucleotides, from the 5' end of exon 44 is represented by SEQ ID NO: 8.

Herein, the complementary sequence to the nucleotide sequences consisting of the 9th to the 30th, the 9th to the 31st, the 9th to the 32nd, the 9th to the 33rd, the 9th to the 34th, the 10th to the 30th, the 10th to the 31st, the 10th to the 32nd, the 10th to the 33rd, the 10th to the 34th, the 11th to the 30th, the 11th to the 31st, the 11th to the 32nd, the 11th to the 33rd, the 11th to the 34th, the 12th to the 30th, the 12th to the 31st, the 12th to the 32nd, the 12th to the 33rd, the 12th to the 34th, the 13th to the 30th, the 13th to the 31st, the 13th to the 32nd, the 13th to the 33rd, the 13th to the 34th, the 24th to the 45th, the 24th to the 46th, the 24th to the 47th, the 24th to the 48th, the 24th to the 49th, the 25th to the 45th, the 25th to the 46th, the 25th to the 47th, the 25th to the 48th, the 25th to the 49th, the 26th to the 45th, the 26th to the 46th, the 26th to the 47th, the 26th to the 48th, the 26th to the 49th, the 27th to the 45th, the 27th to the 46th, the 27th to the 47th, the 27th to the 48th, the 27th to the 49th, the 28th to the 45th, the 28th to the 46th, the 28th to the 47th, the 28th to the 48th, the 28th to the 49th, the 29th to the 45th, the 29th to the 46th, the 29th to the 47th, the 29th to the 48th or the 29th to the 49th nucleotides, from the 5' end of the 44th exon in the human dystrophin gene is respectively identical to the nucleotide sequence consisting of the 119th to the 140th, the 118th to the 140th, the 117th to the 140th, the 116th to the 140th, the 115th to the 140th, 119th to the 139th, the 118th to the 139th, the 117th to the 139th, the 116th to the 139th, the 115th to the 139th, 119th to the 138th, the 118th to the 138th, the 117th to the 138th, the 116th to the 138th, the 115th to the 138th, 119th to the 137th, the 118th to the 137th, the 117th to the 137th, the 116th to the 137th, the 115th to the 137th, 119th to the 136th, the 118th to the 136th, the 117th to the 136th, the 116th to the 136th, the 115th to the 136th, the 104th to the 125th, the 103rd to the 125th, the 102nd to the 125th, the 101th to the 125th, the 100th to the 125th, the 104th to the 124th, the 103rd to the 124th, the 102nd to the 124th, the 101st to the 124th, the 100th to the 124th, the 104th to the 123rd, the 103rd to the 123rd, the 102nd to the 123rd, the 101st to the 123rd, the 100th to the 123rd, the 104th to the 122nd, the 103rd to the 122nd, the 102nd to the 122nd, the 101st to the 122nd, the 100th to the 122nd, the 104th to the 121st, the 103rd to the 121st, the 102nd to the 121st, the 101st to the 121st, the 100th to the 121st, the 104th to the 120th, the 103rd to the 120th, the 102nd to the 120th, the 101st to the 120th or the 100th to the 120th nucleotides of SEQ ID NO: 8.

The relationship between the location in the nucleotide sequence from the 5' end of the 55th, the 45th, the 50th, and the 44th exon and the location in the nucleotide sequence of SEQ ID NO: 5-8 is represented as the tables below.

TABLE 1

| the location of nucleotides from 5' end of exon 55 nucleotide sequences | the location of corresponding nucleotides in the nucleotide sequences of SEQ ID NO. 5 |
| --- | --- |
| -2nd~19th | 172nd~192nd |
| -2nd~20th | 171st~192nd |
| -2nd~21st | 170th~192nd |
| -2nd~22nd | 169th~192nd |
| -2nd~23rd | 168th~192nd |
| -1st~19th | 172nd~191st |
| -1st~20th | 171st~191st |
| -1st~21st | 170th~191st |
| -1st~22nd | 169th~191st |
| -1st~23rd | 168th~191st |
| 1st~19th | 172nd~190th |
| 1st~20th | 172st~190th |
| 1st~21st | 170th~190th |
| 1st~22nd | 169th~190th |
| 1st~23rd | 168th~190th |
| 2nd~19th | 172nd~189th |
| 2nd~20th | 171st~189th |
| 2nd~21st | 170th~189th |
| 2nd~22nd | 169th~189th |
| 2nd~23rd | 168th~189th |
| 3rd~19th | 172nd~188th |
| 3rd~20th | 171st~188th |
| 3rd~21st | 170th~188th |
| 3rd~22nd | 169th~188th |
| 3rd~23rd | 168th~188th |

TABLE 1-continued

| the location of nucleotides from 5' end of exon 55 nucleotide sequences | the location of corresponding nucleotides in the nucleotide sequences of SEQ ID NO. 5 |
|---|---|
| 9th~29th | 162nd~182nd |
| 9th~30th | 161st~182nd |
| 9th~31st | 160th~182nd |
| 9th~32nd | 159th~182nd |
| 9th~33rd | 158th~182nd |
| 10th~29th | 162nd~181st |
| 10th~30th | 161st~181st |
| 10th~31st | 160th~181st |
| 10th~32nd | 159th~181st |
| 10th~33rd | 158th~181st |
| 11th~29th | 162nd~180th |
| 11th~30th | 161st~180th |
| 11th~31st | 160th~180th |
| 11th~32nd | 159th~180th |
| 11th~33rd | 158th~180th |
| 12th~29th | 162nd~179th |
| 12th~30th | 161st~179th |
| 12th~31st | 160th~179th |
| 12th~32nd | 159th~179th |
| 12th~33rd | 158th~179th |
| 13th~29th | 162nd~178th |
| 13th~30th | 161st~178th |
| 13th~31st | 160th~178th |
| 13th~32nd | 159th~178th |
| 13th~33rd | 158th~178th |
| 12th~34th | 157th~179th |
| 12th~35th | 156th~179th |
| 12th~36th | 155th~179th |
| 13th~34th | 157th~178th |
| 13th~35th | 156th~178h |
| 13th~36th | 155th~178th |
| 14th~32nd | 159th~177th |
| 14th~33rd | 158th~177th |
| 14th~34th | 157th~177th |
| 14th~35th | 156th~177th |
| 14th~36th | 155th~177th |
| 15th~32nd | 159th~176th |
| 15th~33rd | 158th~176th |
| 15th~34th | 157th~176th |
| 15th~35th | 156th~176th |
| 15th~36th | 155th~176th |
| 16th~32nd | 159th~175th |
| 16th~33rd | 158th~175th |
| 16th~34th | 157th~175th |
| 16th~35th | 156th~175th |
| 16th~36th | 155th~175th |

TABLE 2

| the location of nucleotides from 5' end of exon 45 nucleotide sequenses | the location of corresponding nucleotides in the nucleotide sequences in SEQ ID NO. 6 |
|---|---|
| -3rd~19th | 158th~179th |
| -3rd~20th | 157th~179th |
| -3rd~21st | 156th~179th |
| -3rd~22nd | 155th~179th |
| -3rd~23rd | 154th~179th |
| -2nd~19th | 158th~178th |
| -2nd~20th | 157th~178th |
| -2nd~21st | 156th~478th |
| -2nd~22nd | 155th~178th |
| -2nd~23rd | 154th~178th |
| -1st~19th | 158th~477th |
| -1st~20th | 157th~177th |
| -1st~21st | 156th~177th |
| -1st~22nd | 155th~177th |
| -1st~23rd | 154th~177th |
| 1st~19th | 158th~176th |
| 1st~20th | 157th~176th |
| 1st~21st | 156th~176th |
| 1st~22nd | 155th~176th |
| 1st~23rd | 154th~176th |

TABLE 2-continued

| the location of nucleotides from 5' end of exon 45 nucleotide sequenses | the location of corresponding nucleotides in the nucleotide sequences in SEQ ID NO. 6 |
|---|---|
| 2nd~19th | 158th~175th |
| 2nd~20th | 157th~175th |
| 2nd~21st | 156th~175th |
| 2nd~22nd | 155th~175th |
| 2nd~23rd | 154th~175th |
| -2nd~24th | 153rd~178th |
| -2nd~25th | 152nd~178th |
| -2nd~26th | 151st~178th |
| -2nd~27th | 150th~178th |
| -1st~24th | 153rd~177th |
| -1st~25th | 152nd~177th |
| -1st~26th | 151st~177th |
| -1st~27th | 150th~177th |
| 1st~24th | 153rd~176th |
| 1st~25th | 152nd~176th |
| 1st~26th | 151st~176th |
| 1st~27th | 150th~176th |
| 2nd~24th | 153rd~175th |
| 2nd~25th | 152nd~175th |
| 2nd~26th | 151st~175h |
| 2nd~27th | 150th~175th |
| 3rd~23rd | 154th~174th |
| 3rd~24th | 153rd~174th |
| 3rd~25th | 152nd~174th |
| 3rd~26th | 151st~174th |
| 3rd~27th | 150th~174th |
| 4th~28th | 149th~173rd |
| 4th~29th | 148th~173rd |
| 4th~30th | 147th~173rd |
| 4th~31st | 146th~173rd |
| 4th~32nd | 147th~173rd |
| 5th~28th | 149th~172nd |
| 5th~29th | 148th~172nd |
| 5th~30th | 147th~172nd |
| 5th~31st | 146th~172nd |
| 5th~32nd | 145th~172nd |
| 6th~28th | 149th~171st |
| 6th~29th | 148th~171st |
| 6th~30th | 147th~171st |
| 6th~31st | 146th~171st |
| 6th~32nd | 145th~171st |
| 7th~28th | 149th~170th |
| 7th~29th | 148th~170th |
| 7th~30th | 147th~170th |
| 7th~31st | 146th~170th |
| 7th~32nd | 145th~170th |
| 8th~28th | 149th~169th |
| 8th~29th | 148th~169th |
| 8th~30th | 147th~169th |
| 8th~31st | 146th~169th |
| 8th~32nd | 145th~169th |

TABLE 3

| the location of nucleotides from 5' end of exon 50 nucleotide sequences | the location of corresponding nucleotides in the nucleotide sequences in SEQ ID NO. 7 |
|---|---|
| 105th~125th | 5th~25th |
| 105th~126th | 4th~25th |
| 105th~127th | 3rd~25th |
| 105th~128th | 2nd~25th |
| 105th~129th | 1st~25th |
| 106th~125th | 5th~24th |
| 106th~126th | 4th~24h |
| 106th~127th | 3rd~24th |
| 106th~128h | 2nd~24th |
| 106th~129th | 1st~24th |
| 107th~125th | 5th~23rd |
| 107th~126h | 4th~23rd |
| 107th~127th | 3rd~23rd |
| 107th~128th | 2nd~23rd |
| 107th~129th | 1st~23rd |

TABLE 3-continued

| the location of nucleotides from 5' end of exon 50 nucleotide sequences | the location of corresponding nucleotides in the nucleotide sequences in SEQ ID NO. 7 |
|---|---|
| 108th~125th | 5th~22nd |
| 108th~126th | 4th~22nd |
| 108th~127h | 3rd~22nd |
| 108th~128th | 2nd~22nd |
| 108th~129th | 1st~22nd |
| 109th~125th | 5th~21st |
| 109th~126th | 4th~21st |
| 109th~127th | 3rd~21st |
| 109th~128th | 2nd~21st |
| 109th~129h | 1st~21st |

TABLE 4

| the location of nucleotides from 5' end of exon 44 nucleotide sequences | the location of corresponding nucleotides in the nucleotide sequences in SEQ ID NO. 8 |
|---|---|
| 9th~30th | 119th~140th |
| 9th~31st | 118th~140th |
| 9th~32nd | 117th~140th |
| 9th~33rd | 116th~140th |
| 9th~34th | 115th~140th |
| 10th~30th | 119th~139th |
| 10th~31st | 118th~139th |
| 10th~32nd | 117th~139th |
| 10th~33rd | 116th~139th |
| 10th~34th | 115th~139th |
| 11th~30th | 119th~138th |
| 11th~31st | 118th~138th |
| 11th~32nd | 117th~138th |
| 11th~33rd | 116th~138th |
| 11th~34th | 115th~138th |
| 12th~30th | 119th~137th |
| 12th~31st | 118th~137th |
| 12th~32nd | 117th~137th |
| 12th~33rd | 116th~137th |
| 12th~34th | 115th~137th |
| 13th~30th | 119th~136th |
| 13th~31st | 118th~136th |
| 13th~32nd | 117th~136th |
| 13th~33rd | 116th~136th |
| 13th~34th | 115th~136th |
| 24th~45th | 104th~125th |
| 24th~46th | 103rd~125th |
| 24th~47th | 102nd~125th |
| 24th~48th | 101st~125th |
| 24th~49th | 100th~125th |
| 25th~45th | 104th~124th |
| 25th~46th | 103rd~124th |
| 25th~47th | 102nd~124th |
| 25th~48th | 101st~124th |
| 25th~49th | 100th~124th |
| 26th~45th | 104th~123rd |
| 26th~46th | 103rd~123rd |
| 26th~47th | 102nd~123rd |
| 26th~48th | 101st~123rd |
| 26th~49th | 100th~123rd |
| 27th~45th | 104th~122nd |
| 27th~46th | 103rd~122nd |
| 27th~47th | 102nd~122nd |
| 27th~48th | 101st~122nd |
| 27th~49th | 100th~122nd |
| 28th~45th | 104th~121st |
| 28th~46th | 103rd~121st |
| 28th~47th | 102nd~121st |
| 28th~48th | 101st~121st |
| 28th~49th | 100th~121st |
| 29th~45th | 104th~120th |
| 29th~46th | 103rd~120th |
| 29th~47th | 102nd~120th |
| 29th~48th | 101st~120th |
| 29th~49th | 100th~120th |

It is preferred that the exon 55 skipping oligomer of the present invention consists of a complementary sequence to any one of the nucleotide sequences consisting of the 1st to the 21st, the 11th to the 31st or the 14th to the 34th nucleotides, from the 5' end of the 55th exon in the human dystrophin gene (e.g., any one of the sequences consisting of the 170th to the 190th, the 160th to the 180th or the 157th to the 177th of SEQ ID NO: 5).

It is preferred that the exon 45 skipping oligomer of the present invention consists of a complementary sequence to any one of the nucleotide sequences consisting of the −2nd to the 19th, the 1st to the 21st, the 1st to the 25th or the 6th to the 30th nucleotides, from the 5' end of the 45th exon in the human dystrophin gene (e.g., any one of the sequences consisting of the 158th to the 178th, 156th to the 176th, the 152nd to the 176th or the 147th to the 171st nucleotides of SEQ ID NO: 6).

It is preferred that the exon 50 skipping oligomer of the present invention consists of a complementary sequence to any one of the nucleotide sequences consisting of the 106th to the 126th or the 107th to the 127th nucleotides, from the 5' end of the 50th exon in the human dystrophin gene (e.g., any one of the sequences consisting of the 4th to the 24th or the 3rd to the 23rd nucleotides of SEQ ID NO: 7).

It is preferred that the exon 44 skipping oligomer of the present invention consists of a complementary sequence to any one of the nucleotide sequences consisting of the 11th to the 32nd, the 25th to the 45th, the 26th to the 46th, the 26th to the 47th or the 27th to the 47th nucleotides, from the 5' end of the 44th exon in the human dystrophin gene (e.g., any one of the sequences consisting of the 117th to the 138th, the 104th to the 124th, the 103rd to the 123rd, the 102nd to the 123rd or the 102nd to the 122nd nucleotides of SEQ ID NO: 8).

The term "cause skipping of the 55th exon in the human dystrophin gene" is intended to mean that by binding of the oligomer of the present invention to the site corresponding to exon 55 of the transcript (e.g., pre-mRNA) of the human dystrophin gene, for example, the nucleotide sequence corresponding to the 5' end of exon 56 is ligated to the 3' side of the nucleotide sequence corresponding to the 3' end of exon 53 in DMD patients with deletion of exon 54 when the transcript is spliced, thus resulting in formation of mature mRNA which is free of codon frame shift.

The term "cause skipping of the 45th exon in the human dystrophin gene" is intended to mean that by binding of the oligomer of the present invention to the site corresponding to exon 45 of the transcript (e.g., pre-mRNA) of the human dystrophin gene, for example, the nucleotide sequence corresponding to the 5' end of exon 46 is ligated to the 3' side of the nucleotide sequence corresponding to the 3' end of exon 43 in DMD patients with deletion of exon 44 when the transcript is spliced, thus resulting in formation of mature mRNA which is free of codon frame shift.

The term "cause skipping of the 50th exon in the human dystrophin gene" is intended to mean that by binding of the oligomer of the present invention to the site corresponding to exon 50 of the transcript (e.g., pre-mRNA) of the human dystrophin gene, for example, the nucleotide sequence corresponding to the 5' end of exon 52 is ligated to the 3' side of the nucleotide sequence corresponding to the 3' end of exon 49 in DMD patients with deletion of exon 51 when the transcript is spliced, thus resulting in formation of mature mRNA which is free of codon frame shift.

The term "cause skipping of the 44th exon in the human dystrophin gene" is intended to mean that by binding of the oligomer of the present invention to the site corresponding to exon 44 of the transcript (e.g., pre-mRNA) of the human dystrophin gene, for example, the nucleotide sequence corresponding to the 5' end of exon46 is ligated to the 3' side of the nucleotide sequence corresponding to the 3' end of exon 43 in DMD patients with deletion of, exon 45 when the transcript is spliced, thus resulting in formation of mature mRNA which is free of codon frame shift.

Accordingly, it is not required for the oligomer of the present invention to have a nucleotide sequence 100% complementary to each target sequence, as far as it causes exon 55, 45, 50 or 44 skipping in the human dystrophin gene. The oligomer of the present invention may include, for example, 1 to 3, 1 or 2, or one nucleotide non-complementary to the target sequence.

Herein, the term "binding" described above is intended to mean that when the oligomer of the present invention is mixed with the transcript of human dystrophin gene, both are hybridized under physiological conditions to form a double strand. The term "under physiological conditions" refers to conditions set to mimic the in vivo environment in terms of pH, salt composition and temperature. The conditions are, for example, 25 to 40° C., preferably 37° C., pH 5 to 8, preferably pH 7.4 and 150 mM of sodium chloride concentration.

Whether the skipping of exon 55, 45, 50 or 44 in the human dystrophin gene is caused or not can be confirmed by introducing the oligomer of the present invention into a dystrophin expressing cell (e.g., human rhabdomyosarcoma cells), amplifying the region surrounding exon 55, 45, 50 or 44 of mRNA of the human dystrophin gene by RT-PCR from the total RNA of the dystrophin expressing cell and performing nested PCR or sequence analysis on the PCR amplified product.

The skipping efficiency can be determined as follows. The mRNA for the human dystrophin gene is collected from test cells; in the mRNA, the polynucleotide level "A" of the band where exon 55, 45, 50 or 44 is skipped and the polynucleotide level "B" of the band where exon 55, 45, 50 or 44 is not skipped are measured. Using these measurement values of "A" and "B," the efficiency is calculated by the following equation:

$$\text{Skipping efficiency}(\%)=A/(A+B)\times 100$$

The oligomer of the present invention includes, for example, an oligonucleotide, morpholino oligomer or peptide nucleic acid (PNA), having a length of 18 to 28 nucleotides. The length is preferably from 15 to 30 nucleotides or 20 to 25 nucleotides and morpholino oligomers are preferred.

The oligonucleotide described above (hereinafter referred to as "the oligonucleotide of the present invention") is the oligomer of the present invention composed of nucleotides as constituent units. Such nucleotides may be any of ribonucleotides, deoxyribonucleotides and modified nucleotides.

The modified nucleotide refers to one having fully or partly modified nucleobases, sugar moieties and/or phosphate-binding regions, which constitute the ribonucleotide or deoxyribonucleotide.

The nucleobase includes, for example, adenine, guanine, hypoxanthine, cytosine, thymine, uracil, and modified bases thereof. Examples of such modified nucleobases include, but not limited to, pseudouracil, 3-methyluracil, dihydrouracil, 5-alkylcytosines (e.g., 5-methylcytosine), 5-alkyluracils (e.g., 5-ethyluracil), 5-halouracils (5-bromouracil), 6-azapyrimidine, 6-alkylpyrimidines (6-methyluracil), 2-thiouracil, 4-thiouracil, 4-acetylcytosine, 5-(carboxyhydroxymethyl) uracil, 5'-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, xanthine, etc.

Modification of the sugar moiety may include, for example, modifications at the 2'-position of ribose and modifications of the other positions of the sugar. The modification at the 2'-position of ribose includes replacement of the 2'-OH of ribose with OR, R, R'OR, SH, SR, $NH_2$, NHR, $NR_2$, $N_3$, CN, F, Cl, Br or I, wherein R represents an alkyl or an aryl and R' represents an alkylene.

The modification for the other positions of the sugar includes, for example, replacement of O at the 4' position of ribose or deoxyribose with S, bridging between 2' and 4' positions of the sugar, e.g., LNA (Locked Nucleic Acid) or ENA (2'-O,4'-C-Ethylene-bridged Nucleic Acids), but is not limited thereto.

A modification of the phosphate-binding region includes, for example, a modification of replacing phosphodiester bond with phosphorothioate bond, phosphorodithioate bond, alkyl phosphonate bond, phosphoroamidate bond or boranophosphate bond (Enya et al: Bioorganic & Medicinal Chemistry, 2008, 18, 9154-9160) (cf., e.g., Japan Domestic Re-Publications of PCT Application Nos. 2006/129594 and 2006/038608).

The alkyl is preferably a straight or branched alkyl having 1 to 6 carbon atoms. Specific examples include methyl, ethyl, n-propyl, isopropyl, n-butyl, isobutyl, sec-butyl, tert-butyl, n-pentyl, isopentyl, neopentyl, tert-pentyl, n-hexyl and isohexyl. The alkyl may optionally be substituted. Examples of such substituents are a halogen, an alkoxy, cyano and nitro. The alkyl may be substituted with 1 to 3 substituents.

The cycloalkyl is preferably a cycloalkyl having 5 to 12 carbon atoms. Specific examples include cyclopentyl, cyclohexyl, cycloheptyl, cyclooctyl, cyclodecyl and cyclododecyl.

The halogen includes fluorine, chlorine, bromine and iodine.

The alkoxy is a straight or branched alkoxy having 1 to 6 carbon atoms such as methoxy, ethoxy, n-propoxy, isopropoxy, n-butoxy, isobutoxy, sec-butoxy, tert-butoxy, n-pentyloxy, isopentyloxy, n-hexyloxy, isohexyloxy, etc. Among others, an alkoxy having 1 to 3 carbon atoms is preferred.

The aryl is preferably an aryl having 6 to 10 carbon atoms. Specific examples include phenyl, α-naphthyl and β-naphthyl. Among others, phenyl is preferred. The aryl may optionally be substituted. Examples of such substituents are an alkyl, a halogen, an alkoxy, cyano and nitro. The aryl may be substituted with one to three of such substituents.

The alkylene is preferably a straight or branched alkylene having 1 to 6 carbon atoms. Specific examples include methylene, ethylene, trimethylene, tetramethylene, pentamethylene, hexamethylene, 2-(ethyl)trimethylene and 1-(methyl)tetramethylene.

The acyl includes a straight or branched alkanoyl or aroyl. Examples of the alkanoyl include formyl, acetyl, 2-methylacetyl, 2,2-dimethylacetyl, propionyl, butyryl, isobutyryl, pentanoyl, 2,2-dimethylpropionyl, hexanoyl, etc. Examples of the aroyl include benzoyl, toluoyl and naphthoyl. The aroyl may optionally be substituted at substitutable positions and may be substituted with an alkyl(s).

Preferably, the oligonucleotide of the present invention is the oligomer of the present invention containing a constituent unit represented by general formula below wherein the —OH group at position 2' of ribose is substituted with methoxy and the phosphate-binding region is a phosphorothioate bond:

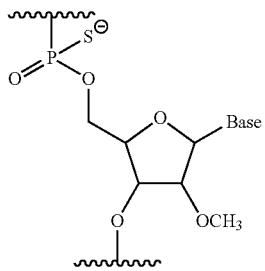

wherein Base represents a nucleobase.

The oligonucleotide of the present invention may be easily synthesized using various automated synthesizer (e.g., AKTA oligopilot plus 10/100 (GE Healthcare)). Alternatively, the synthesis may also be entrusted to a third-party organization (e.g., Promega Inc., or Takara Co.), etc.

The morpholino oligomer of the present invention is the oligomer of the present invention comprising the constituent unit represented by general formula below:

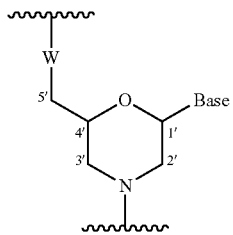

wherein Base has the same significance as defined above, and,
W represents a group shown by any one of the following groups:

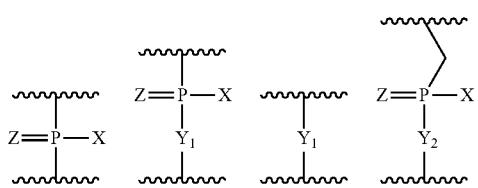

wherein X represents —CH$_2$R$^1$, —O—CH$_2$R$^1$, —S—CH$_2$R$^1$, —NR$^2$R$^3$ or F;
R$^1$ represents H or an alkyl;
R$^2$ and R$^3$, which may be the same or different, each represents H, an alkyl, a cycloalkyl or an aryl;
Y$_1$ represents O, S, CH$_2$ or NR$^1$;
Y$_2$ represents O, S or NR$^1$;
Z represents O or S.

Preferably, the morpholino oligomer is an oligomer comprising a constituent unit represented by general formula below (phosphorodiamidate morpholino oligomer (hereinafter referred to as "PMO")).

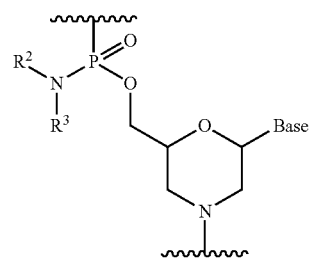

wherein Base, R$^2$ and R$^3$ have the same significance as defined above.

The morpholino oligomer may be produced in accordance with, e.g., WO 1991/009033 or WO 2009/064471. In particular, PMO can be produced by the procedure described in WO 2009/064471 or produced by the process shown below.

[Method for Producing PMO]

An embodiment of PMO is, for example, the compound represented by general formula (I) below (hereinafter PMO (I)).

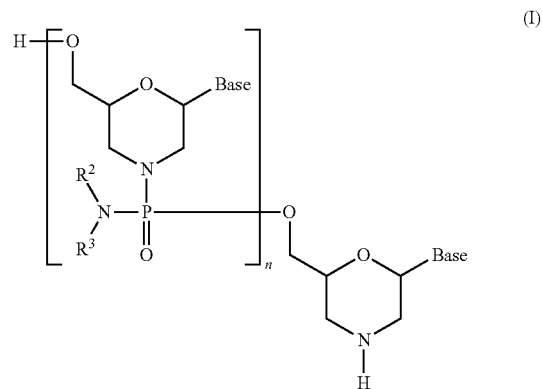

wherein Base, R$^2$ and R$^3$ have the same significance as defined above; and, n is a given integer of 1 to 99, preferably a given integer of 18 to 28.

PMO (I) can be produced in accordance with a known method, for example, can be produced by performing the procedures in the following steps.

The compounds and reagents used in the steps below are not particularly limited so long as they are commonly used to prepare PMO.

Also, the following steps can all be carried out by the liquid phase method or the solid phase method (using manuals or commercially available solid phase automated synthesizers). In producing PMO by the solid phase method, it is desired to use automated synthesizers in view of simple operation procedures and accurate synthesis.

(1) Step A:

The compound represented by general formula (II) below (hereinafter referred to as Compound (II)) is reacted with an acid to prepare the compound represented by general formula (III) below (hereinafter referred to as Compound (III)):

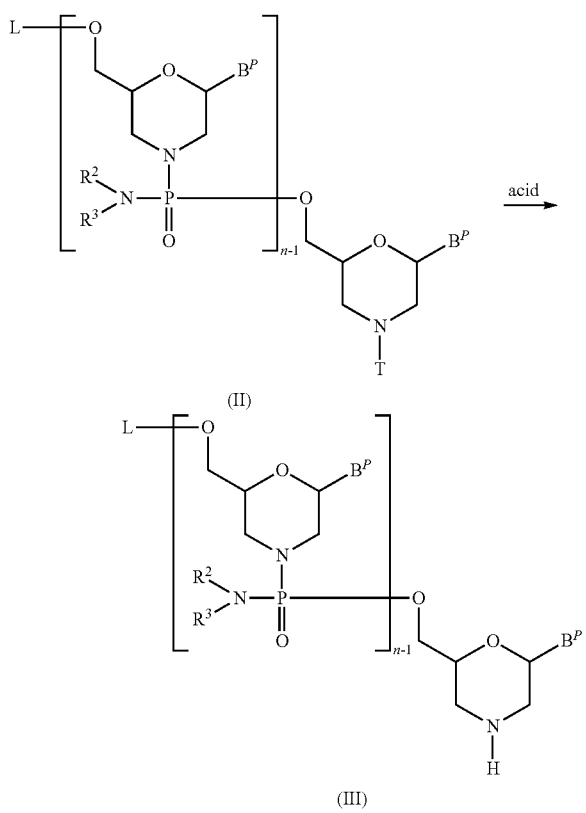

(II)

(III)

wherein n, $R^2$ and $R^3$ have the same significance as defined above;

each $B^P$ independently represents a nucleobase which may optionally be protected;

T represents trityl, monomethoxytrityl or dimethoxytrityl; and,

L represents hydrogen, an acyl or a group represented by general formula (IV) below (hereinafter referred to as group (IV)).

(IV)

The "nucleobase" for $B^P$ includes the same "nucleobase" as in Base, provided that the amino or hydroxy group in the nucleobase shown by $B^P$ may be protected.

Such protective group for amino is not particularly limited so long as it is used as a protective group for nucleic acids. Specific examples include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene. Specific examples of the protective group for the hydroxy group include 2-cyanoethyl, 4-nitrophenethyl, phenylsulfonylethyl, methylsulfonylethyl and trimethylsilylethyl, and phenyl, which may be substituted by 1 to 5 electron-withdrawing group at optional substitutable positions, diphenylcarbamoyl, dimethylcarbamoyl, diethylcarbamoyl, methylphenylcarbamoyl, 1-pyrolidinylcarbamoyl, morpholinocarbamoyl, 4-(tert-butylcarboxy)benzyl, 4-[(dimethylamino)carboxy]benzyl and 4-(phenylcarboxy)benzyl, (cf., e.g., WO 2009/064471).

The "solid carrier" is not particularly limited so long as it is a carrier usable for the solid phase reaction of nucleic acids. It is desired for the solid carrier to have the following properties: e.g., (i) it is sparingly soluble in reagents that can be used for the synthesis of morpholino nucleic acid derivatives (e.g., dichloromethane, acetonitrile, tetrazole, N-methylimidazole, pyridine, acetic anhydride, lutidine, trifluoroacetic acid); (ii) it is chemically stable to the reagents usable for the synthesis of morpholino nucleic acid derivatives; (iii) it can be chemically modified; (iv) it can be charged with desired morpholino nucleic acid derivatives; (v) it has a strength sufficient to withstand high pressure through treatments; and (vi) it has a uniform particle diameter range and distribution. Specifically, swellable polystyrene (e.g., aminomethyl polystyrene resin 1% dibenzylbenzene crosslinked (200-400 mesh) (2.4-3.0 mmol/g) (manufactured by Tokyo Chemical Industry), Aminomethylated Polystyrene Resin .HCl [dibenzylbenzene 1%, 100-200 mesh] (manufactured by Peptide Institute, Inc.)), non-swellable polystyrene (e.g., Primer Support (manufactured by GE Healthcare)), PEG chain-attached polystyrene (e.g., $NH_2$-PEG resin (manufactured by Watanabe Chemical Co.), TentaGel resin), controlled pore glass (controlled pore glass; CPG) (manufactured by, e.g., CPG), oxalyl-controlled pore glass (cf., e.g., Alul et al., Nucleic Acids Research, Vol. 19, 1527 (1991)), TentaGel support-aminopolyethylene glycol-derivatized support (cf., e.g., Wright et al., Tetrahedron Letters, Vol. 34, 3373 (1993)), and a copolymer of Poros-polystyrene/divinylbenzene.

A "linker" which can be used is a known linker generally used to connect nucleic acids or morpholino nucleic acid derivatives. Examples include 3-aminopropyl, succinyl, 2,2'-diethanolsulfonyl and a long chain alkyl amino (LCAA).

This step can be performed by reacting Compound (II) with an acid.

The "acid" which can be used in this step includes, for example, trifluoroacetic acid, dichloroacetic acid and trichloroacetic acid. The acid used is appropriately in a range of, for example, 0.1 mol equivalent to 1000 mol equivalents based on 1 mol of Compound (II), preferably in a range of 1 mol equivalent to 100 mol equivalents based on 1 mol of Compound (II).

An organic amine can be used in combination with the acid described above. The organic amine is not particularly limited and includes, for example, triethylamine. The amount of the organic amine used is appropriately in a range of, e.g., 0.01 mol equivalent to 10 mol equivalents, and preferably in a range of 0.1 mol equivalent to 2 mol equivalents, based on 1 mol of the acid.

When a salt or mixture of the acid and the organic amine is used in this step, the salt or mixture includes, for example, a salt or mixture of trifluoroacetic acid and triethylamine, and more specifically, a mixture of 1 equivalent of triethylamine and 2 equivalents of trifluoroacetic acid.

The acid which can be used in this step may also be used in the form of a dilution with an appropriate solvent in a concentration of 0.1% to 30%. The solvent is not particularly limited as far as it is inert to the reaction, and includes, for example, dichloromethane, acetonitrile, an alcohol (ethanol, isopropanol, trifluoroethanol, etc.), water, or a mixture thereof.

The reaction temperature in the reaction described above is preferably in a range of, e.g., 10° C. to 50° C., more preferably in a range of 20° C. to 40° C., and most preferably, in a range of 25° C. to 35° C.

The reaction time may vary depending upon kind of the acid used and reaction temperature, and is appropriately in a range of 0.1 minute to 24 hours in general, and preferably in a range of 1 minute to 5 hours.

After completion of this step, a base may be added, if necessary, to neutralize the acid remained in the system. The "base" is not particularly limited and includes, for example, diisopropylamine. The base may also be used in the form of a dilution with an appropriate solvent in a concentration of 0.1% (v/v) to 30% (v/v).

The solvent used in this step is not particularly limited so long as it is inert to the reaction, and includes dichloromethane, acetonitrile, an alcohol (ethanol, isopropanol, trifluoroethanol, etc.), water, and a mixture thereof. The reaction temperature is preferably in a range of, e.g., 10° C. to 50° C., more preferably, in a range of 20° C. to 40° C., and most preferably, in a range of 25° C. to 35° C.

The reaction time may vary depending upon kind of the base used and reaction temperature, and is appropriately in a range of 0.1 minute to 24 hours in general, and preferably in a range of 1 minute to 5 hours.

In Compound (II), the compound of general formula (IIa) below (hereinafter Compound (IIa)), wherein n is 1 and L is a group (IV), can be produced by the following procedure.

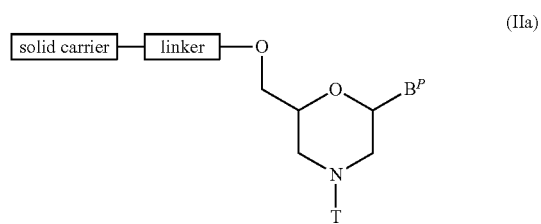

wherein $B^P$, T, linker and solid carrier have the same significance as defined above.

Step 1:

The compound represented by general formula (V) below is reacted with an acylating agent to prepare the compound represented by general formula (VI) below (hereinafter referred to as Compound (VI)).

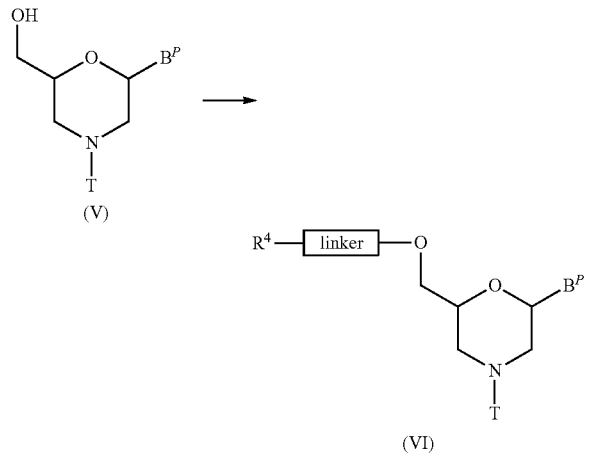

wherein $B^P$, T and linker have the same significance as defined above; and, $R^4$ represents hydroxy, a halogen or amino.

This step can be carried out by known procedures for introducing linkers, using Compound (V) as the starting material.

In particular, the compound represented by general formula (VIa) below can be produced by performing the method known as esterification, using Compound (V) and succinic anhydride.

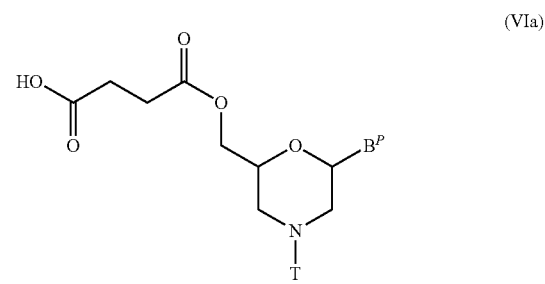

wherein $B^P$ and T have the same significance as defined above.

Step 2:

Compound (VI) is reacted with a solid career by a condensing agent to prepare Compound (IIa).

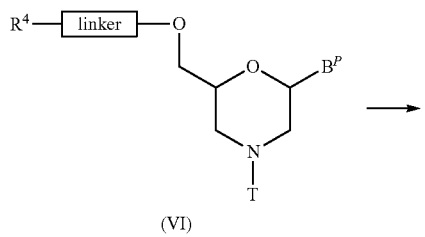

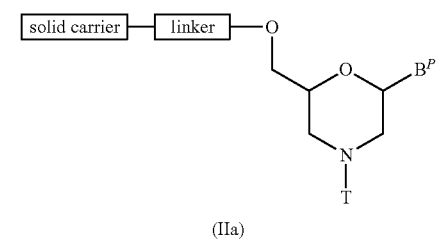

wherein $B^P$, $R^4$, T, linker and solid carrier have the same significance as defined above.

This step can be performed using Compound (VI) and a solid carrier in accordance with a process known as condensation reaction.

In Compound (II), the compound represented by general formula (IIa2) below wherein n is 2 to 99 and L is a group represented by general formula (IV) can be produced by using Compound (IIa) as the starting material and repeating step A and step B of the PMO production method described in the specification for a desired number of times.

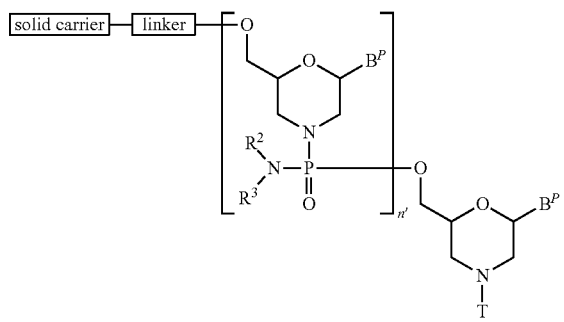

(IIa2)

wherein $B^P$, $R^2$, $R^3$, T, linker and solid carrier have the same significance as defined above; and, n' represents 1 to 98.

In Compound (II), the compound of general formula (IIb) below wherein n is 1 and L is hydrogen can be produced by the procedure described in, e.g., WO 1991/009033.

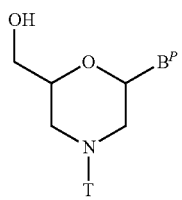

(IIb)

wherein $B^P$ and T have the same significance as defined above.

In Compound (II), the compound represented by general formula (IIb2) below wherein n is 2 to 99 and L is hydrogen can be produced by using Compound (IIb) as the starting material and repeating step A and step B of the PMO production method described in the specification for a desired number of times.

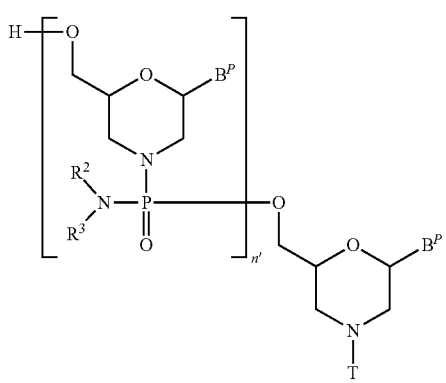

(IIb2)

wherein $B^P$, n', $R^2$, $R^3$ and T have the same significance as defined above.

In Compound (II), the compound represented by general formula (IIc) below wherein n is 1 and L is an acyl can be produced by performing the procedure known as acylation reaction, using Compound (IIb).

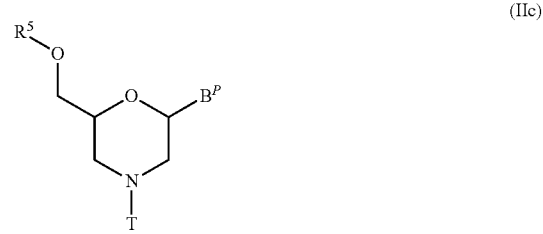

(IIc)

wherein $B^P$ and T have the same significance as defined above; and, $R^5$ represents an acyl.

In Compound (II), the compound represented by general formula (IIc2) below wherein n is 2 to 99 and L is an acyl can be produced by using Compound (IIc) as the starting material and repeating step A and step B of the PMO production method described in the specification for a desired number of times.

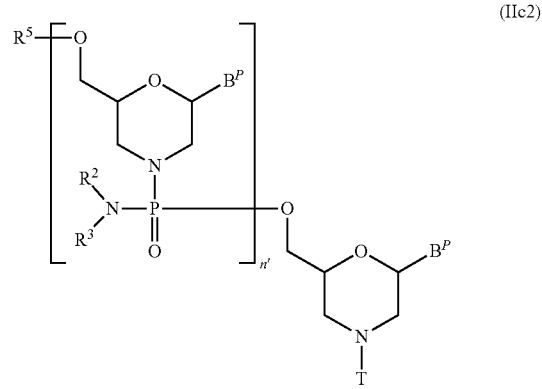

(IIc2)

wherein $B^P$, n', $R^2$, $R^3$, $R^5$ and T have the same significance as defined above.

(2) Step B

Compound (III) is reacted with a morpholino monomer compound in the presence of a base to prepare the compound represented by general formula (VII) below (hereinafter referred to as Compound (VII)):

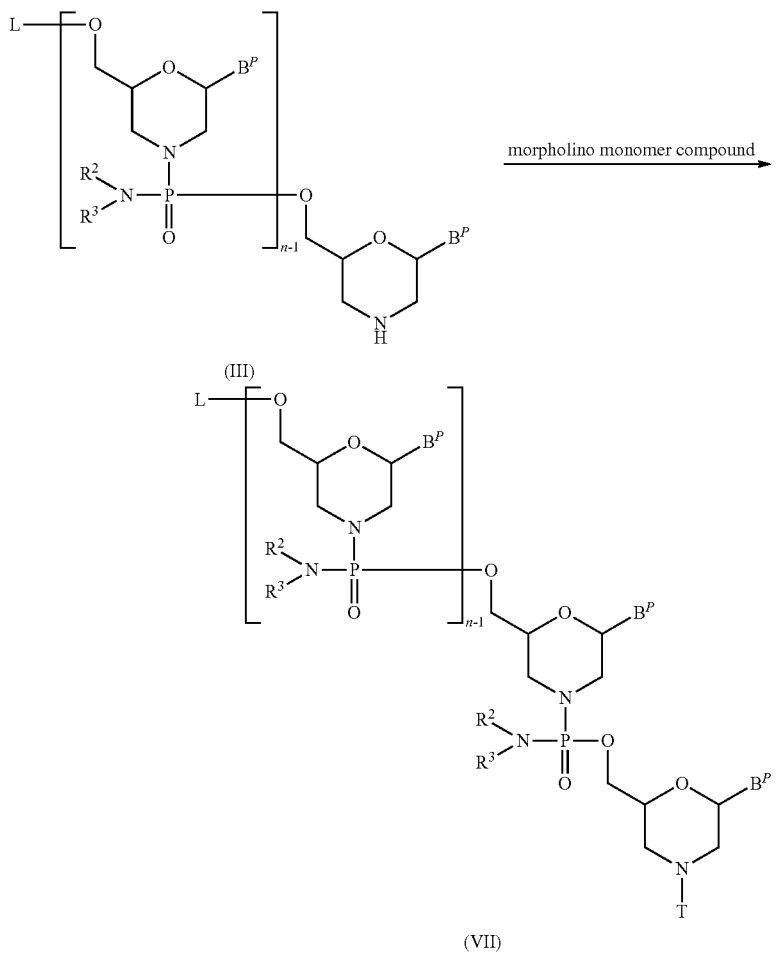

(VII)

wherein $B^P$, L, n, $R^2$, $R^3$ and T have the same significance as defined above.

This step can be performed by reacting Compound (III) with the morpholino monomer compound in the presence of a base.

The morpholino monomer compound includes, for example, compounds represented by general formula (VIII) below:

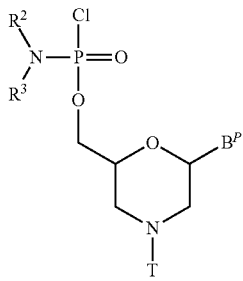

(VIII)

wherein $B^P$, $R^2$, $R^3$ and T have the same significance as defined above.

The "base" which can be used in this step includes, for example, diisopropylamine, triethylamine and N-ethylmorpholine. The amount of the base used is appropriately in a range of 1 mol equivalent to 1000 mol equivalents based on 1 mol of Compound (III), preferably, 10 mol equivalents to 100 mol equivalents based on 1 mol of Compound (III).

The morpholino monomer compound and base which can be used in this step may also be used as a dilution with an appropriate solvent in a concentration of 0.1% to 30%. The solvent is not particularly limited as far as it is inert to the reaction, and includes, for example, N,N-dimethylimidazolidone, N-methylpiperidone, DMF, dichloromethane, acetonitrile, tetrahydrofuran, or a mixture thereof.

The reaction temperature is preferably in a range of, e.g., 0° C. to 100° C., and more preferably, in a range of 10° C. to 50° C.

The reaction time may vary depending upon kind of the base used and reaction temperature, and is appropriately in a range of 1 minute to 48 hours in general, and preferably in a range of 30 minutes to 24 hours.

Furthermore, after completion of this step, an acylating agent can be added, if necessary. The "acylating agent" includes, for example, acetic anhydride, acetyl chloride and phenoxyacetic anhydride. The acylating agent may also be used as a dilution with an appropriate solvent in a concentration of 0.1% to 30%. The solvent is not particularly limited as far as it is inert to the reaction, and includes, for example, dichloromethane, acetonitrile, an alcohol(s) (ethanol, isopropanol, trifluoroethanol, etc.), water, or a mixture thereof.

If necessary, a base such as pyridine, lutidine, collidine, triethylamine, diisopropylethylamine, N-ethylmorpholine, etc. may also be used in combination with the acylating agent. The amount of the acylating agent is appropriately in a range of 0.1 mol equivalent to 10000 mol equivalents, and preferably in a range of 1 mol equivalent to 1000 mol equivalents. The amount of the base is appropriately in a range of, e.g., 0.1 mol equivalent to 100 mol equivalents, and preferably in a range of 1 mol equivalent to 10 mol equivalents, based on 1 mol of the acylating agent.

The reaction temperature in this reaction is preferably in a range of 10° C. to 50° C., more preferably, in a range of 10° C. to 50° C., much more preferably, in a range of 20° C. to 40° C., and most preferably, in a range of 25° C. to 35° C. The reaction time may vary depending upon kind of the acylating agent used and reaction temperature, and is appropriately in a range of 0.1 minute to 24 hours in general, and preferably in a range of 1 minute to 5 hours.

(3) Step C:

In Compound (VII) produced in Step B, the protective group is removed using a deprotecting agent to prepare the compound represented by general formula (IX).

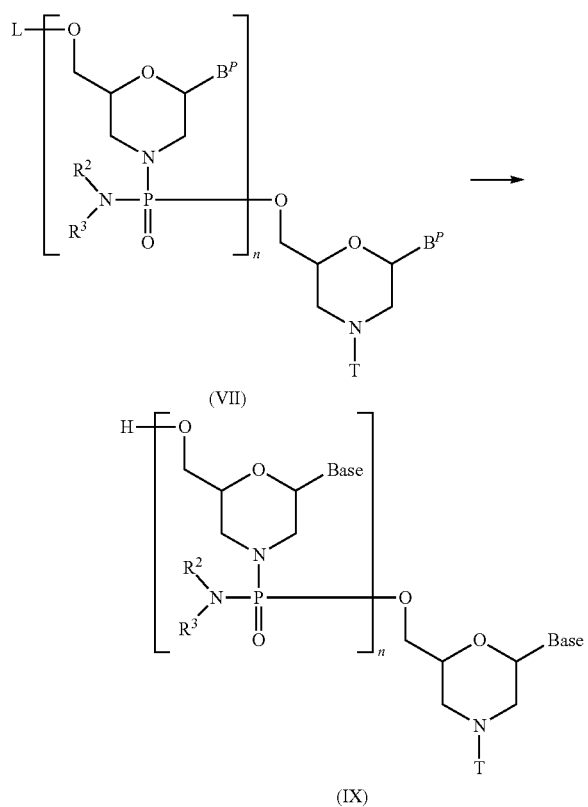

wherein Base, $B^P$, L, n, $R^2$, $R^3$ and T have the same significance as defined above.

This step can be performed by reacting Compound (VII) with a deprotecting agent.

The "deprotecting agent" includes, e.g., conc. ammonia water and methylamine. The "deprotecting agent" used in this step may also be used as a dilution with, e.g., water, methanol, ethanol, isopropyl alcohol, acetonitrile, tetrahydrofuran, DMF, N,N-dimethylimidazolidone, N-methylpiperidone, or a mixture of these solvents. Among others, ethanol is preferred. The amount of the deprotecting agent used is appropriately in a range of, e.g., 1 mol equivalent to 100000 mol equivalents, and preferably in a range of 10 mol equivalents to 1000 mol equivalents, based on 1 mol of Compound (VII).

The reaction temperature is appropriately in a range of 15° C. to 75° C., preferably, in a range of 40° C. to 70° C., and more preferably, in a range of 50° C. to 60° C. The reaction time for deprotection may vary depending upon kind of Compound (VII), reaction temperature, etc., and is appropriately in a range of 10 minutes to 30 hours, preferably 30 minutes to 24 hours, and more preferably in a range of 5 hours to 20 hours.

(4) Step D:

PMO (I) is produced by reacting Compound (IX) produced in step C with an acid:

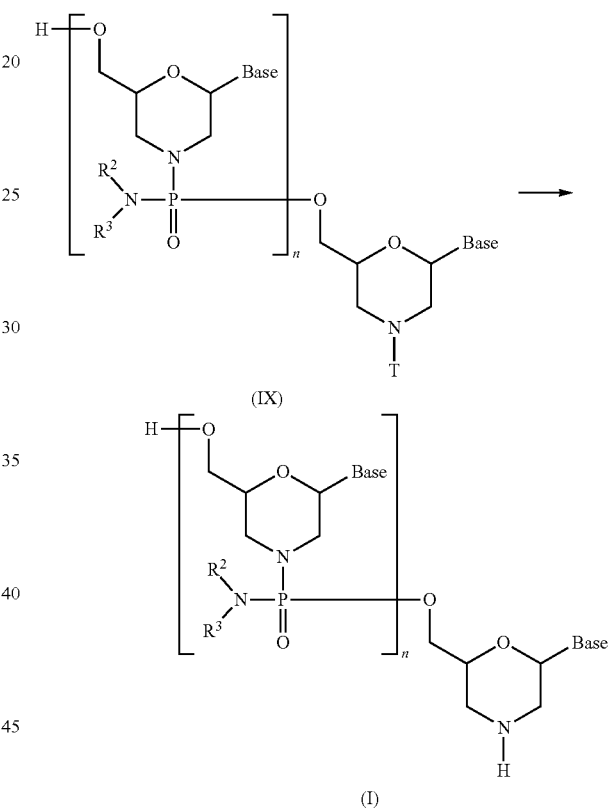

wherein Base, n, $R^2$, $R^3$ and T have the same significance as defined above.

This step can be performed by adding an acid to Compound (IX).

The "acid" which can be used in this step includes, for example, trichloroacetic acid, dichloroacetic acid, acetic acid, phosphoric acid, hydrochloric acid, etc. The acid used is appropriately used to allow the solution to have a pH range of 0.1 to 4.0, and more preferably, in a range of pH 1.0 to 3.0. The solvent is not particularly limited so long as it is inert to the reaction, and includes, for example, acetonitrile, water, or a mixture of these solvents thereof.

The reaction temperature is appropriately in a range of 10° C. to 50° C., preferably, in a range of 20° C. to 40° C., and more preferably, in a range of 25° C. to 35° C. The reaction time for deprotection may vary depending upon kind of Compound (IX), reaction temperature, etc., and is appropriately in a range of 0.1 minute to 5 hours, preferably 1 minute to 1 hour, and more preferably in a range of 1 minute to 30 minutes.

PMO (I) can be obtained by subjecting the reaction mixture obtained in this step to conventional means of separation and purification such as extraction, concentration, neutralization, filtration, centrifugal separation, recrystallization, reversed phase column chromatography $C_8$ to $C_{18}$, cation exchange column chromatography, anion exchange column chromatography, gel filtration column chromatography, high performance liquid chromatography, dialysis, ultrafiltration, etc., alone or in combination thereof. Thus, the desired PMO (I) can be isolated and purified (cf., e.g., WO 1991/09033).

In purification of PMO (I) using reversed phase chromatography, e.g., a solution mixture of 20 mM triethylamine/acetate buffer and acetonitrile can be used as an elution solvent.

In purification of PMO (I) using ion exchange chromatography, e.g., a solution mixture of 1 M saline solution and 10 mM sodium hydroxide aqueous solution can be used as an elution solvent.

A peptide nucleic acid is the oligomer of the present invention having a group represented by the following general formula as the constituent unit:

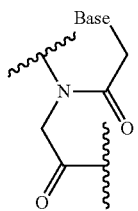

wherein Base has the same significance as defined above.

Peptide nucleic acids can be prepared by referring to, e.g., the following literatures.
1) P. E. Nielsen, M. Egholm, R. H. Berg, O. Buchardt, Science, 254, 1497 (1991)
2) M. Egholm, O. Buchardt, P. E. Nielsen, R. H. Berg, Jacs., 114, 1895 (1992)
3) K. L. Dueholm, M. Egholm, C. Behrens, L. Christensen, H. F. Hansen, T. Vulpius, K. H. Petersen, R. H. Berg, P. E. Nielsen, O. Buchardt, J. Org. Chem., 59, 5767 (1994)
4) L. Christensen, R. Fitzpatrick, B. Gildea, K. H. Petersen, H. F. Hansen, T. Koch, M. Egholm, O. Buchardt, P. E. Nielsen, J. Coull, R. H. Berg, J. Pept. Sci., 1, 175 (1995)
5) T. Koch, H. F. Hansen, P. Andersen, T. Larsen, H. G. Batz, K. Otteson, H. Orum, J. Pept. Res., 49, 80 (1997)

In the oligomer of the present invention, the 5' end may be any of chemical structures (1) to (3) below, and preferably is (3)-OH.

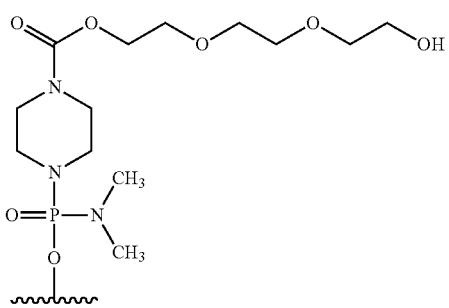

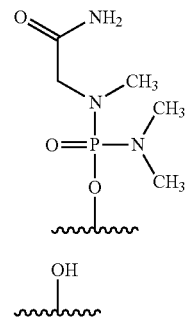

Hereinafter, the groups shown by (1), (2) and (3) above are referred to as "Group (1)," "Group (2)" and "Group (3)," respectively.

2. Pharmaceutical Composition

The oligomer of the present invention causes exon 55, 45, 50 and 44 skipping with a higher efficiency as compared to the prior art antisense oligomers. It is thus expected that conditions of muscular dystrophy can be relieved with high efficiency by administering the pharmaceutical composition comprising the oligomer of the present invention to DMD patients. For example, when the pharmaceutical composition comprising the oligomer of the present invention is used, the same therapeutic effects can be achieved even in a smaller dose than that of the oligomers of the prior art. Accordingly, side effects can be alleviated and such is economical.

In another embodiment, the present invention provides the pharmaceutical composition for the treatment of muscular dystrophy, comprising as an active ingredient the oligomer of the present invention, a pharmaceutically acceptable salt or hydrate thereof (hereinafter referred to as "the composition of the present invention").

Examples of the pharmaceutically acceptable salt of the oligomer of the present invention contained in the composition of the present invention are alkali metal salts such as salts of sodium, potassium and lithium; alkaline earth metal salts such as salts of calcium and magnesium; metal salts such as salts of aluminum, iron, zinc, copper, nickel, cobalt, etc.; ammonium salts; organic amine salts such as salts of t-octylamine, dibenzylamine, morpholine, glucosamine, phenylglycine alkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium, tris(hydroxymethyl)aminomethane; hydrohalide salts such as salts of hydrofluorates, hydrochlorides, hydrobromides and hydroiodides; inorganic acid salts such as nitrates, perchlorates, sulfates, phosphates, etc.; lower alkane sulfonates such as methanesulfonates, trifluoromethanesulfonates and ethanesulfonates; arylsulfonates such as benzenesulfonates and p-toluenesulfonates; organic acid salts such as acetates, malates, fumarates, succinates, citrates, tartarates, oxalates, maleates, etc.; and, amino acid salts such as salts of glycine, lysine, arginine, ornithine, glutamic acid and aspartic acid. These salts may be produced by known methods. Alternatively, the oligomer of the present invention contained in the composition of the present invention may be in the form of a hydrate thereof.

Administration route for the composition of the present invention is not particularly limited so long as it is pharmaceutically acceptable route for administration, and can be chosen depending upon method of treatment. In view of easiness in delivery to muscle tissues, preferred are intravenous administration, intraarterial administration, intramuscular administration, subcutaneous administration, oral administration, tissue administration, transdermal administration, etc. Also, dosage forms which are available for the composition of the present invention are not particularly limited, and include, for example, various injections, oral agents, drips, inhalations, ointments, lotions, etc.

In administration of the oligomer of the present invention to patients with muscular dystrophy, the composition of the present invention preferably contains a carrier to promote delivery of the oligomer to muscle tissues. Such a carrier is not particularly limited as far as it is pharmaceutically acceptable, and examples include cationic carriers such as cationic liposomes, cationic polymers, etc., or carriers using viral envelope. The cationic liposomes are, for example, liposomes composed of 2-O-(2-diethylaminoethyl)carabamoyl-1,3-O-dioleoylglycerol and phospholipids as the essential constituents (hereinafter referred to as "liposome A"), Oligofectamine (registered trademark) (manufactured by Invitrogen Corp.), Lipofectin (registered trademark) (manufactured by Invitrogen Corp.), Lipofectamine (registered trademark) (manufactured by Invitrogen Corp.), Lipofectamine 2000 (registered trademark) (manufactured by Invitrogen Corp.), DMRIE-C (registered trademark) (manufactured by Invitrogen Corp.), GeneSilencer (registered trademark) (manufactured by Gene Therapy Systems), TransMessenger (registered trademark) (manufactured by QIAGEN, Inc.), TransIT TKO (registered trademark) (manufactured by Mirus) and Nucleofector II (Lonza). Among others, liposome A is preferred. Examples of cationic polymers are JetSI (registered trademark) (manufactured by Qbiogene, Inc.) and Jet-PEI (registered trademark) (polyethylenimine, manufactured by Qbiogene, Inc.). An example of carriers using viral envelop is GenomeOne (registered trademark) (HVJ-E liposome, manufactured by Ishihara Sangyo). Alternatively, the medical devices described in Japanese Patent No. 2924179 and the cationic carriers described in Japanese Domestic Re-Publication PCT Nos. 2006/129594 and 2008/096690 may be used as well.

A concentration of the oligomer of the present invention contained in the composition of the present invention may vary depending on kind of the carrier, etc., and is appropriately in a range of 0.1 nM to 100 µM, preferably in a range of 1 nM to 10 µM, and more preferably in a range of 10 nM to 1 µM. A weight ratio of the oligomer of the present invention contained in the composition of the present invention and the carrier (carrier/oligomer of the present invention) may vary depending on property of the oligomer, type of the carrier, etc., and is appropriately in a range of 0.1 to 100, preferably in a range of 1 to 50, and more preferably in a range of 10 to 20.

In addition to the oligomer of the present invention and the carrier described above, pharmaceutically acceptable additives may also be optionally formulated in the composition of the present invention. Examples of such additives are emulsification aids (e.g., fatty acids having 6 to 22 carbon atoms and their pharmaceutically acceptable salts, albumin and dextran), stabilizers (e.g., cholesterol and phosphatidic acid), isotonizing agents (e.g., sodium chloride, glucose, maltose, lactose, sucrose, trehalose), and pH controlling agents (e.g., hydrochloric acid, sulfuric acid, phosphoric acid, acetic acid, sodium hydroxide, potassium hydroxide and triethanolamine). One or more of these additives can be used. The content of the additive in the composition of the present invention is appropriately 90 wt % or less, preferably 70 wt % or less and more preferably, 50 wt % or less.

The composition of the present invention can be prepared by adding the oligomer of the present invention to a carrier dispersion and adequately stirring the mixture. Additives may be added at an appropriate step either before or after addition of the oligomer of the present invention. An aqueous solvent that can be used in adding the oligomer of the present invention is not particularly limited as far as it is pharmaceutically acceptable, and examples are injectable water or injectable distilled water, electrolyte fluid such as physiological saline, etc., and sugar fluid such as glucose fluid, maltose fluid, etc. A person skilled in the art can appropriately choose conditions for pH and temperature for such matter.

The composition of the present invention may be prepared into, e.g., a liquid form and its lyophilized preparation. The lyophilized preparation can be prepared by lyophilizing the composition of the present invention in a liquid form in a conventional manner. The lyophilization can be performed, for example, by appropriately sterilizing the composition of the present invention in a liquid form, dispensing an aliquot into a vial container, performing preliminary freezing for 2 hours at conditions of about −40 to −20° C., performing a primary drying at 0 to 10° C. under reduced pressure, and then performing a secondary drying at about 15 to 25° C. under reduced pressure. In general, the lyophilized preparation of the composition of the present invention can be obtained by replacing the content of the vial with nitrogen gas and capping.

The lyophilized preparation of the composition of the present invention can be used in general upon reconstitution by adding an optional suitable solution (reconstitution liquid) and redissolving the preparation. Such a reconstitution liquid includes injectable water, physiological saline and other infusion fluids. A volume of the reconstitution liquid may vary depending on the intended use, etc., is not particularly limited, and is suitably 0.5 to 2-fold greater than the volume prior to lyophilization or no more than 500 mL.

It is desired to control a dose of the composition of the present invention to be administered, by taking the following factors into account: the type and dosage form of the oligomer of the present invention contained; patients' conditions including age, body weight, etc.; administration route; and the characteristics and extent of the disease. A daily dose calculated as the amount of the oligomer of the present invention is generally in a range of 0.1 mg to 10 g/human, and preferably 1 mg to 1 g/human. This numerical range may vary occasionally depending on type of the target disease, administration route and target molecule. Therefore, a dose lower than the range may be sufficient in some occasion and conversely, a dose higher than the range may be required occasionally. The composition can be administered from once to several times daily or at intervals from one day to several days.

In still another embodiment of the composition of the present invention, there is provided a pharmaceutical composition comprising a vector capable of expressing the oligonucleotide of the present invention and the carrier described above. Such an expression vector may be a vector capable of expressing a plurality of the oligonucleotides of the present invention. The composition may be formulated with pharmaceutically acceptable additives as in the case with the composition of the present invention containing the oligomer of the present invention. A concentration of the expression vector contained in the composition may vary depending upon type of the career, etc., and is appropriately in a range of 0.1 nM to 100 μM, preferably in a range of 1 nM to 10 μM, and more preferably in a range of 10 nM to 1 μM. A weight ratio of the expression vector contained in the composition and the carrier (carrier/expression vector) may vary depending on property of the expression vector, type of the carrier, etc., and is appropriately in a range of 0.1 to 100, preferably in a range of 1 to 50, and more preferably in a range of 10 to 20. The content of the carrier contained in the composition is the same as in the case with the composition of the present invention containing the oligomer of the present invention, and a method for producing the same is also the same as in the case with the composition of the present invention.

EXAMPLES

Hereinafter, the present invention will be described in more detail with reference to EXAMPLES and TEST EXAMPLES below, but is not deemed to be limited thereto.

Reference Example 1

4-{[(2S,6R)-6-(4-Benzamido-2-oxopyrimidin-1-yl)-4-tritylmorpholin-2-yl]methoxy}-4-oxobutanoic acid loaded onto amino polystyrene resin Step 1: Production of 4-{[(2S,6R)-6-(4-benzamido-2-oxopyrimidin-1(2H)-yl)-4-tritylmorpholin-2-yl] methoxy}-4-oxobutanoic acid Under argon atmosphere, 3.44 g of N-{1-[(2R,6S)-6-(hydroxymethyl)-4-tritylmorpholin-2-yl]-2-oxo-1,2-dihydropyrimidin-4-yl}benzamide and 1.1 g of 4-dimethylaminopyridine (4-DMAP) were suspended in 50 mL of dichloromethane, and 0.90 g of succinic anhydride was added to the suspension, followed by stirring at room temperature for 3 hours. To the reaction mixture was added 10 mL of methanol, and the mixture was concentrated under reduced pressure. The residue was extracted using ethyl acetate and 0.5 M aqueous potassium dihydrogenphosphate solution. The resulting organic layer was washed sequentially with 0.5 M aqueous potassium dihydrogenphosphate solution, water and brine in the order mentioned. The resulting organic layer was dried over sodium sulfate and concentrated under reduced pressure to give 4.0 g of the product.

Step 2; Production of 4-{[(2S,6R)-6-(4-benzamido-2-oxopyrimidin-1-yl)-4-tritylmorpholin-2-yl] methoxy}-4-oxobutanoic acid loaded onto amino polystyrene resin After 4.0 g of 4-{[(2S,6R)-6-(4-benzamido-2-oxopyrimidin-1(2H)-yl)-4-tritylmorpholin-2-yl]methoxy}-4-oxobutanoic acid was dissolved in 200 mL of pyridine (dehydrated), 0.73 g of 4-DMAP and 11.5 g of 1-ethyl-3-(3-dimethylaminopropyl)carbodiimide hydrochloride were added to the solution. Then, 25.0 g of amino polystyrene resin Primer support 200 amino (manufactured GE Healthcare Japan Co., Ltd., 17-5214-97) and 8.5 mL of triethylamine were added to the mixture, followed by shaking at room temperature for 4 days. After completion of the reaction, the resin was taken out by filtration. The resulting resin was washed sequentially with pyridine, methanol and dichloromethane in the order mentioned, and dried under reduced pressure. To the resulting resin were added 200 mL of tetrahydrofuran (dehydrate), 15 mL of acetic anhydride and 15 mL of 2,6-lutidine, and the mixture was shaken at room temperature for 2 hours. The resin was taken out by filtration, washed sequentially with pyridine, methanol and dichloromethane in the order mentioned and dried under reduced pressure to give 26.7 g of the product.

The loading amount of the product was determined from the molar amount of the trityl per g resin by measuring UV absorbance at 409 nm using a known method. The loading amount of the resin was 192.2 μmol/g.

Conditions of UV Measurement
  Apparatus: U-2910 (Hitachi, Ltd.)
  Solvent: methanesulfonic acid
  Wavelength: 265 nm
  Wavelength: 26

Reference Example 2

4-[[(2S,6R)-6-[6-(2-Cyanoethoxy)-2-[(2-phenoxyacetyl)amino]purine-9-yl]-4-tritylmorpholin-2-yl] methoxy]-4-oxo-butanoic acid loaded onto aminopolystyrene resin Step 1: Production of $N^2$-(phenoxyacetyl) guanosine Guanosine, 100 g, was dried at 80° C. under reduced pressure for 24 hours. After 500 mL of pyridine (anhydrous) and 500 mL of dichloromethane (anhydrous) were added thereto, 401 mL of chlorotrimethylsilane was dropwise added to the mixture under an argon atmosphere at 0° C., followed by stirring at room temperature for 3 hours. The mixture was again ice-cooled and 66.3 g of phenoxyacetyl chloride was dropwise added thereto. Under ice cooling, the mixture was stirred for further 3 hours. To the reaction solution was added 500 mL of methanol, and the mixture was stirred at room temperature overnight. The solvent was then removed by distillation under reduced pressure. The residue was added with 500 mL of methanol and concentrated under reduced pressure, the process was performed 3 times. To the residue was added 4 L of water, and the mixture was stirred for an hour under ice cooling. The precipitates formed were taken out by filtration, washed sequentially with water and cold methanol and then dried to give 150.2 g of the objective compound (yield 102%)(cf.: Org. Lett. (2004), Vol. 6, No. 15, 2555-2557).

Step 2: $N^9$-{[(2R,6S)-6-(hydroxymethyl)-4-morpholin-2-yl]-6-oxo-6,9-dihydro-1H-purin-2-yl}-2-phenoxyacetamide p-toluenesulfonate In 480 mL of methanol was suspended 30 g of the compound obtained in Step 1, and 130 mL of 2N hydrochloric acid was added to the suspension under ice cooling. Subsequently, 56.8 g of ammonium tetraborate tetrahydrate and 16.2 g of sodium periodate were added to the mixture in the order mentioned and the mixture was stirred at room temperature for 3 hours. The reaction mixture was ice cooled and the insoluble matters were removed off by filtration, followed by washing with 100 mL of methanol. The filtrate and washing liquid were combined and the mixture was ice cooled. To the mixture was added 11.52 g of 2-picoline borane. After stirring for 20 minutes, 54.6 g of p-toluenesulfonic acid monohydrate was slowly added to the mixture, followed by stirring at 4° C. overnight. The precipitates formed were taken out by filtration and washed with 500 mL of cold methanol and dried to give 17.7 g of the objective compound (yield: 43.3%).

$^1$H NMR (ht. The precipitates were taken o35 (1H, s), 7.55 (2H, m), 7.35 (2H, m), 7.10 (2H, d, J=7.82 Hz), 7.00 (3H, m), 5.95 (1H, dd, J=10.64, 2.42 Hz), 4.85 (2H, s), 4.00 (1H, m), 3.90-3.60 (2H, m), 3.50-3.20 (5H, m), 2.90 (1H, m), 2.25 (3H, s)

Step 3: Production of $N^9$-{(2R,6S)-6-hydroxymethyl-4-tritylmolpholin-2-yl}-$N^2$-(phenoxyacetyl) guanine In dichloromethane (30 mL) was suspended 2.0 g of the compound (2.0 g) obtained by Step 2, and triethylamine (13.9 g) and trityl chloride (18.3 g) were added to the suspension under ice cooling. The mixture was stirred at room temperature for an hour. The reaction mixture was washed with saturated sodium bicarbonate aqueous solution and then with water. The organic layer was collected, dried over magnesium sulfate and concentrated under reduced pressure. To the residue was added 0.2 M sodium citrate buffer (pH 3)/methanol (1:4 (v/v), 40 mL), and the mixture was stirred. Subsequently, water (40 mL) was added and the suspension mixture was stirred for an hour under ice cooling. The precipitates were taken out by filtration, washed with cold methanol and dried to give 1.84 g of the objective compound (yield: 82.0%).

Step 4: Production of $N^9$-[(2R,6S)-6-{(tert-butyldimethylsilyloxy)methyl}-4-tritylmorpholin-2-yl]-$N^2$-(phenoxyacetyl) guanine In dichloromethane (300 mL) was dissolved the compound (38.3 g) obtained by Step 3, and imidazole (4.64 g) and t-butyldimethylsilyl chloride (9.47 g) were added to the solution in this order mentioned under ice cooling. The reaction solution was stirred at room temperature for an hour. The reaction solution was washed with 0.2 M sodium citrate buffer (pH 3) and then with brine. The organic layer was collected, dried over magnesium sulfate and concentrated under reduced pressure to give 44.1 g of the objective compound as a crude product.

Step 5: Production of $N^9$-[(2R,6S)-6-{(tert-butyldimethylsilyloxy)methyl}-4-tritylmorpholin-2-yl]-$N^2$-(phenoxyacetyl)-$O^6$-triisopropylbenzenesulfonyl guanine In dichloromethane (300 mL) was dissolved the compound (44.1 g) obtained by Step 4, and 4-dimethylaminopyridine (0.64 g), triethylamine (29.2 mL) and triisopropylbenzensulfonyl chloride (19.0 g) were added to the solution under ice cooling. The reaction solution was stirred at room temperature for an hour. The reaction solution was washed with 1 M aqueous sodium dihydrogenphosphate solution. The organic layer was collected, dried over magnesium sulfate and concentrated under reduced pressure to give 60.5 g of the objective compound as a crude product.

Step 6: Production of $N^9$-[(2R,6S)-6-{(tert-butyldimethylsilyloxy)methyl}-4-tritylmorpholin-2-yl]-$N^2$-(phenoxyacetyl)-$O^6$ (2-cyanoethyl) guanine In dichloromethane (300 mL) was dissolved the compound (60.5 g) obtained by Step 5, and N-methylpyrrolidine (54.5 mL) was added to the solution under ice cooling. The reaction solution was stirred under ice cooling for an hour. Then, ethylene cyanohydrin (37.2 g), and 1,8-diazabicyclo[5.4.0]undec-7-ene (11.96 g) were added to the solution, and the solution was stirred under ice cooling for 2 hours. The reaction solution was washed with 1 M sodium dihydrogenphosphate solution and then with water. The organic layer was collected, dried over magnesium sulfate and concentrated under reduced pressure to give 72.4 g of the objective compound as a crude product.

Step 7: Production of $N^9$-[(2R,6S)-6-hydroxymethyl-4-tritylmorpholin-2-yl]-$N^2$-(phenoxyacetyl)-$O^6$-(2-cyanoethyl) guanine In dichloromethane (300 mL) was dissolved the compound (72.4 g) obtained in Step 6, and triethylaminetrihydrofluoride (21.1 g) was added to the solution. The reaction solution was stirred at room temperature for 17 hours. The reaction solution was poured into cold saturated sodiumbicarbonate aqueous solution to neutralize the reaction solution. Then, the dichloromethane layer was collected, dried over magnesium sulfate and concentrated under reduced pressure. The residue was purified by a silica gel column chromatography (PSQ100B (manufactured by FUJI SILYSIA CHEMICAL LTD. The same shall apply hereinafter.)) to give 14.3 g of the objective compound (yield from Step 4: 39.2%).

Step 8: Production of 4-[[[(2S,6S)-6-[6-(2-cyanoethoxy)-2-(2-phenoxyacetyl)amino]purin-9-yl]-4-tritylmorpholin-2-yl]methoxy]-4-oxo-butanoic acid loaded onto amino polystyrene resin The title compound was produced in a manner similar to REFERENCE EXAMPLE 1, except that $N^9$-[(2R,6S)-6-hydroxymethyl-4-tritylmorpholin-2-yl]-$N^2$-(phenoxyacetyl)-$O^6$-(2-cyanoethyl) guanine was used in this step, instead of N-{1-[(2R,6S)-6-(hydroxymethyl)-4-tritylmorpholin-2-yl]-2-oxo-1,2-dihydropyrimidin-4-yl}benzamide used in Step 1 of REFERENCE EXAMPLE 1.

Reference Example 3

4-{[(2S,6R)-6-(5-Methyl-2,4-dioxo-3,4-dihydropyrimidin-1-yl)-4-tritylmorpholin-2-yl]methoxy}-4-oxobutanoic acid loaded onto aminopolystyrene resin The title compound was produced in a manner similar to REFERENCE EXAMPLE 1, except that 1-[(2R,6S)-6-(hydroxymethyl)-4-tritylmorpholin-2-yl]-5-methylpyrimidine-2,4(1H, 3H)-dione was used in this step, instead of N-{1-[(2R,6S)-6-(hydroxymethyl)-4-tritylmorpholin-2-yl]-2-oxo-1,2-dihydropyrimidin-4-yl}benzamide used in Step 1 of REFERENCE EXAMPLE 1.

Reference Example 4

4-{[(2S,6R)-6-(6-benzamidepurine-9-yl)-4-tritylmorpholin-2-yl]methoxy}-4-oxobutanoic acid loaded onto aminopolystyrene resin The title compound was produced in a manner similar to REFERENCE EXAMPLE 1, except that N-{9-[(2R,6S)-6-(hydroxymethyl)-4-tritylmorpholin-2-yl]purine-6-yl}benzamide was used in this step, instead of N-{1-[(2R, 6S)-6-(hydroxymethyl)-4-tritylmorpholin-2-yl]-2-oxo-1,2-dihydropyrimidin-4-yl}benzamide used in Step 1 of REFERENCE EXAMPLE 1.

Reference Example 5

1,12-Dioxo-1-(4-tritylpiperazin-1-yl)-2,5,8,11-tetraoxa-15-pentadecanoic acid loaded onto aminopolystyrene resin The title compound was produced in a manner similar to REFERENCE EXAMPLE 1, except that 2-[2-(2-hydroxyethoxy)ethoxy]ethyl 4-tritylpiperazine-1-carboxylic acid (the compound described in WO2009/064471) was used in this step, instead of N-{1-[(2R,6S)-6-(hydroxymethyl)-4-tritylmorpholin-2-yl]-2-oxo-1,2-dihydropyrimidin-4-yl}benzamide used in Step 1 of REFERENCE EXAMPLE 1.

EXON 45

According to the descriptions in EXAMPLES 1 to 8 and REFERENCE EXAMPLE 1 below, various types of PMO shown by PMO Nos. 1-6 and 8-10 in TABLE 5 were synthesized. The PMO synthesized was dissolved in water for injection (manufactured by Otsuka Pharmaceutical Factory, Inc.). PMO No. 7 was purchased from Gene Tools, LLC.

TABLE 5

| PMO No. | Sequence name | Note | SEQ ID NO: |
|---|---|---|---|
| 1 | H45_-2-9(OH) | 5' end: group (3) | 9 |
| 2 | H45_-1-20(OH) | 5' end: group (3) | 10 |
| 3 | H45_1-21(OH) | 5' end: group (3) | 11 |
| 4 | H45_2-22(OH) | 5' end: group (3) | 12 |
| 5 | H45_3-23(OH) | 5' end: group (3) | 13 |
| 6 | H45_-4-21(OH) | Sequence corresponding to SEQ ID NO; 30 in Patent Document 4, 5' end: group (3) | 14 |
| 7 | H45_5-34(GT) | Sequence corresponding to SEQ ID NO; 4 in Patent Document 3, 5' end: group (2) | 15 |
| 8 | H45_1-20(OH) | 5' end: group (3) | 16 |
| 9 | H45_2-21(OH) | 5' end: group (3) | 17 |
| 10 | H45_1-21(TEG) | 5' end: group (1) | 18 |

Example 1

PMO No. 1

0.2 g 4-{[(2S,6R)-6-(4-benzamide-2-oxopyrimidin-1(2H)-yl)-4-tritylmorpholin-2-yl]methoxy}4-oxobutanoic acid supported on an aminopolystyrene resin (Reference Example 1) (26 μmol) was filled in a column with a filter tip. Then, the synthetic cycle shown below was started using an nucleic acid synthesizing machine (AKTA Oligopilot 10 plus). The desired morpholino monomer compound was added in each coupling cycle to give the nucleotide sequence of the title compound.

TABLE 6

| Step | Reagent | Volume (mL) | Time (min) |
|---|---|---|---|
| 1 | deblocking solution | 18-32 | 1.8-3.2 |
| 2 | neutralizing and washing solution | 30 | 1.5 |
| 3 | coupling solution B | 5 | 0.5 |
| 4 | coupling solution A | 1.3 | 0.25 |
| 5 | mixture of step 3 and step 4 reagents mixture | 6.3 | 120-300 |
| 6 | acetonitrile | 20 | 1.0 |
| 7 | capping solution | 9 | 2.0 |
| 8 | acetonitrile | 30 | 2.0 |

The deblocking solution used was dichloromethane containing 3% (w/v) trifluoroacetic acid. The neutralizing and washing solution used was a solution obtained by dissolving N,N-diisopropylethylamine to be 10% (v/v) and tetrahydrofuran to be 5% (v/v) in dichloromethane containing 35% (v/v) acetonitrile. The coupling solution A used was a solution obtained by dissolving the morpholino monomer compound in tetrahydrofuran to be 0.10 M. The coupling solution B used was a solution obtained by dissolving N,N-diisopropylethylamine to be 20% (v/v) and tetrahydrofuran to be 10% (v/v) in acetonitrile. The capping solution used was a solution obtained by dissolving 20% (v/v) acetic anhydride and 30% (v/v) 2,6-lutidine in acetonitrile.

The aminopolystyrene resin loaded with the PMO synthesized above was recovered from the reaction vessel and dried at room temperature for at least 2 hours under reduced pressure. The dried PMO loaded onto aminopolystyrene resin was charged in a reaction vessel, and 5 mL of 28% ammonia water-ethanol (1/4) was added thereto. The mixture was stirred at 55° C. for 15 hours. The aminopolystyrene resin was separated by filtration and washed with 1 mL of water-ethanol (1/4). The resulting filtrate was concentrated under reduced pressure. The resulting residue was dissolved in 10 mL of a solvent mixture of 20 mM of acetic acid—triethylamine buffer (TEAA buffer) and 10 mL of acetonitrile (4/1) and filtered through a membrane filter. The filtrate obtained was purified by reversed phase HPLC. The conditions used are as follows.

TABLE 7

| Column | XBridge 5 μm C18 |
|---|---|
| | (Waters, φ 19 × 50 mm, 1 CV = 14 mL) |
| Flow rate | 10 mL/min |
| Column temperature | room temperature |
| Solution A | 20 mM TEAA buffer |
| Solution B | $CH_3CN$ |
| Gradient | (B) conc. 10 → 70%/15 CV |

Each fraction was analyzed, and the objective product was recovered and concentrated under reduced pressure. To the concentrated residue was added 0.5 mL of 2 M phosphoric acid aqueous solution, and the mixture was stirred for 15 minutes. Furthermore, 2 mL of 2 M sodium hydroxide aqueous solution was added to make the mixture alkaline, followed by filtration through a membrane filter (0.45 μm).

The resulting aqueous solution containing the objective product was purified by an anionic exchange resin column. The conditions used are as follows.

TABLE 8

| Column | Source 15Q (GE Healthcare, φ 10 × 108 mm, 1 CV = 8.5 mL) |
|---|---|
| Flow rate | 8.5 mL/min |
| Column temperature | room temperature |
| Solution A | 10 mM sodium hydroxide aqueous solution |
| Solution B | 10 mM sodium hydroxide aqueous solution, 1 M sodium chloride aqueous solution |
| Gradient | (B) conc. 1 → 50%/40 CV |

Each fraction was analyzed (on HPLC) and the objective product was obtained as an aqueous solution. To the resulting aqueous solution was added 0.1 M phosphate buffer (pH 6.0) for neutralization. Next, the mixture obtained was demineralized by reversed phase HPLC under the conditions described below.

TABLE 9

| Column | XBridge 5 μm C8 (Waters, φ 10 × 50 mm, 1 CV = 4 mL) |
|---|---|
| Flow rate | 4 mL/min |
| Column temperature | 60° C. |
| Solution A | water |
| Solution B | CH₃CN |
| Gradient | (B) conc. 0 → 50%/20 CV |

The objective product was recovered and the mixture was concentrated under reduced pressure. The resulting residue was dissolved in water. The aqueous solution obtained was freeze-dried to give 1.5 mg of the objective compound as a white cotton-like solid.

| ESI-TOF-MS | Clcd.: 6877.8 |
|---|---|
| | Found: 6877.4 |

Example 2

PMO. No. 3

The title compound was produced in accordance with the procedure of EXAMPLE 1.

| ESI-TOF-MS | Clcd.: 6862.8 |
|---|---|
| | Found: 6862.5 |

Example 3

PMO. No. 2

The title compound was produced in accordance with the procedure of EXAMPLE 1.

| ESI-TOF-MS | Clcd.: 6862.8 |
|---|---|
| | Found: 6862.3 |

Example 4

PMO. No. 4

The title compound was produced in accordance with the procedure of EXAMPLE 1, except that 4-[[(2S,6R)-6-[6-(2-cyanoethoxy)-2-[(2-phenoxyacetyl)amino]purin-9-yl]-4-tritylmorpholin-2-yl]methoxy]-4-oxo-butanoic acid loaded onto aminopolystyrene resin (REFERENCE EXAMPLE 2) was used as the starting material.

| ESI-TOF-MS | Clcd.: 6902.8 |
|---|---|
| | Found: 6902.3 |

Example 5

PMO. No. 5

The title compound was produced in accordance with the procedure of EXAMPLE 1, except that 4-(((2S,6R)-6-(5-methyl-2,4-dioxo-3,4-dihydropyrimidine-1(2H)-yl)-4-tritylmorpholin-2-yl)methoxy)-4-oxobutanoic acid loaded onto aminopolystyrene resin (REFERENCE EXAMPLE 3) was used as the starting material.

| ESI-TOF-MS | Clcd.: 6902.8 |
|---|---|
| | Found: 6902.4 |

Example 6

PMO. No. 8

The title compound was produced in accordance with the procedure of EXAMPLE 1.

| ESI-TOF-MS | Clcd.: 6547.5 |
|---|---|
| | Found: 6547.2 |

Example 7

PMO. No. 9

The title compound was produced in accordance with the procedure of EXAMPLE 1.

| ESI-TOF-MS | Clcd.: 6547.5 |
|---|---|
| | Found: 6547.2 |

Example 8

PMO. No. 10

The title compound was produced in accordance with the procedure of EXAMPLE 1, except that 1,12-Dioxo-1-(4-tritylpiperazin-1-yl)-2,5,8,11-tetraoxa-15-pentadecanoic acid loaded onto aminopolystyrene resin (REFERENCE EXAMPLE 5) was used as the starting material.

| ESI-TOF-MS | Clcd.: 7214.1 |
|---|---|
| | Found: 7213.7 |

Comparative Example 1

PMO. No. 6

The title compound was produced in accordance with the procedure of EXAMPLE 1.

| ESI-TOF-MS | Clcd.: 8193.9 |
|---|---|
| | Found: 8195.3 |

Test Example 1

In Vitro Assay

Experiments were performed using the antisense oligomers of 2'-O-methoxy-phosphorothioates (2'-OMe-S-RNA) shown by SEQ ID NO: 19 to SEQ ID NO: 35. Various antisense oligomers used for the assay were purchased from Japan Bio Services. The sequences of various antisense oligomers are given below.

TABLE 10

| Antisense oligomer | Nucleotide sequence | SEQ ID NO: |
|---|---|---|
| H45_1-25 | GCUGCCCAAUGCCAUCCUGGAGUUC | 19 |
| H45_6-30 | UUGCCGCUGCCCAAUGCCAUCCUGG | 20 |
| H45_11-35 | ACAGUUUGCCGCUGCCCAAUGCCAU | 21 |
| H45_16-40 | UGACAACAGUUUGCCGCUGCCCAAU | 22 |
| H45_21-45 | UGUUCUGACAACAGUUUGCCGCUGC | 23 |
| H45_26-50 | UUCAAUGUUCUGACAACAGUUUGCC | 24 |
| H45_31-55 | UUGCAUUCAAUGUUCUGACAACAGU | 25 |
| H45_36-60 | CCCAGUUGCAUUCAAUGUUCUGACA | 26 |
| H45_41-65 | UCUUCCCCAGUUGCAUUCAAUGUUC | 27 |
| H45_46-70 | UUAUUUCUUCCCCAGUUGCAUUCAA | 28 |
| H45_51-75 | CUGAAUUAUUUCUUCCCCAGUUGCA | 29 |
| H45_56-80 | GAUUGCUGAAUUAUUUCUUCCCCAG | 30 |
| H45_61-85 | UUGAGGAUUGCUGAAUUAUUUCUUC | 31 |
| H45_66-90 | UGUUUUUGAGGAUUGCUGAAUUAUU | 32 |
| H45_71-95 | GCAUCUGUUUUUGAGGAUUGCUGAA | 33 |
| H45_76-100 | UACUGGCAUCUGUUUUUGAGGAUUG | 34 |
| H45_7-31 | UUUGCCGCUGCCCAAUGCCAUCCUG | 35 |

RD cells (human rhabdomyosarcoma cell line) were plated at $1\times10^5$ in a 12-well plate and cultured in 1 mL of Eagle's minimal essential medium (EMEM) (manufactured by Sigma, Inc., hereinafter the same) containing 10% fetal calf serum (FCS) (manufactured by Invitrogen Corp.) under conditions of 37° C. and 5% $CO_2$ overnight. Complexes of various antisense oligomers (Japan Bio Services) (0.3 or 1 µM) for exon 45 skipping and Lipofectamine 2000 (manufactured by Invitrogen Corp.) were prepared and 100 µL of the complex was added to RD cells where 0.9 mL of the medium was exchanged, to reach the final concentration of 30 or 100 nM.

After completion of the addition, the cells were cultured overnight. The cells were washed twice with PBS (manufactured by Nissui, hereafter the same) and then 250 µL of ISOGEN (manufactured by Nippon Gene) was added to the cells. After the cells were allowed to stand at room temperature for a few minutes for cell lysis, the lysate was collected in an Eppendorf tube. The total RNA was extracted according th the protocol attached to ISOGEN. The concentration of the total RNA extracted was determined using a NanoDrop ND-1000 (manufactured by LMS).

RT-PCR was performed with 400 ng of the extracted total RNA using a QIAGEN OneStep RT-PCR Kit. A reaction solution was prepared in accordance with the protocol attached to the kit. A PTC-100 (manufactured by MJ Research) was used as a thermal cycler. The RT-PCR program used is as follows.

50° C., 30 mins: reverse transcription
94° C., 15 mins: thermal denaturation
[94° C., 30 seconds; 60° C., 30 seconds; 72° C., 1 min]×35 cycles: PCR amplification
72° C., 10 mins:

The nucleotide sequences of the forward primer and reverse primer used for RT-PCR are given below.

```
Forward primer:
                                   (SEQ ID NO: 36)
  5'- GCTCAGGTCGGATTGACATT-3'

Reverse primer:
                                   (SEQ ID NO: 37)
  5'- GGGCAACTCTTCCACCAGTA-3'
```

The reaction product, 1 µL of the PCR above was analyzed using a Bioanalyzer (manufactured by Agilent Technologies, Inc.). The polynucleotide level "A" of the band with exon 45 skipping and the polynucleotide level "B" of the band without exon 45 skipping were measured. Based on these measurement values of "A" and "B", the skipping efficiency was determined by the following equation:

$$\text{Skipping efficiency}(\%) = A/(A+B) \times 100$$

Experimental Results

Figure 2:
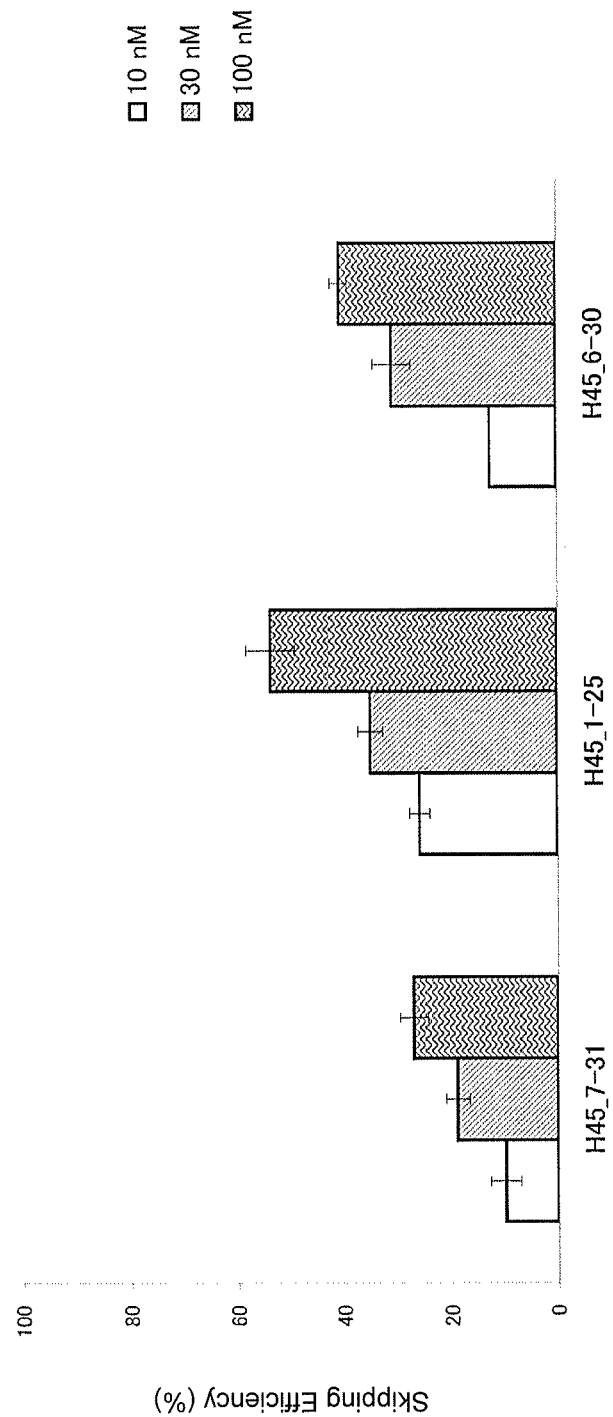
FIG. 2 shows the efficiency of exon 45 skipping by 2'-OMe-S-RNA oligomer in the human dystrophin gene in human rhabdomyosarcoma cell line (RD cells).

The results are shown in FIGS. 1 and 2. These experiments revealed that, when the antisense oligomers were designed at the 1st to the 25th, or the 6th to the 30th nucleotides from the 5' end of exon 45 in the human dystrophin gene, exon 45 skipping could be caused with a higher efficiency than that of the antisense oligomer which is designed at the 7th to the 31st nucleotides from the 5' end of exon 45.

Test Example 2

In Vitro Assay

Using an Amaxa Cell Line Nucleofector Kit L on Nucleofector II (Lonza), 1, 3, or 10 µM of the oligomers PMO Nos. 1 to 5 and 8 to 10 of the present invention and the antisense oligomers PMO Nos. 6 and 7 were transfected with $3.5\times10^5$ of RD cells (human rhabdomyosarcoma cell line). The Program T-030 was used.

After transfection, the cells were cultured for 3 days in 2 mL of Eagle's minimal essential medium (EMEM) (manufactured by Sigma, hereinafter the same) containing 10% fetal calf serum (FCS) (manufactured by Invitrogen) under conditions of 37° C. and 5% $CO_2$. The cells were washed twice with PBS (manufactured by Nissui, hereinafter the same) and 500 µL of ISOGEN (manufactured by Nippon Gene) was added to the cells. After the cells were allowed to stand at room temperature for a few minutes to lyse the cells, the lysate was collected in an Eppendorf tube. The total RNA was extracted according to the protocol attached to ISOGEN. The concentration of the total RNA extracted was determined using a NanoDrop ND-1000 (manufactured by LMS).

RT-PCR was performed with 400 ng of the extracted total RNA using a QIAGEN OneStep RT-PCR Kit (manufactured by QIAGEN). A reaction solution was prepared in accordance with the protocol attached to the kit. A PTC-100 (manufactured by MJ Research) was used as a thermal cycler. The RT-PCR program used is as follows.

50° C., 30 mins: reverse transcription
95° C., 15 mins: thermal denaturation
[94° C., 30 seconds; 60° C., 30 seconds; 72° C., 1 min]×35 cycles: PCR amplification
72° C., 10 mins:

The nucleotide sequences of the forward primer and reverse primer used for RT-PCR are given below.

```
Forward primer:
                            (SEQ ID NO: 36)
5'- GCTCAGGTCGGATTGACATT-3'

Reverse primer:
                            (SEQ ID NO: 37)
5'- GGGCAACTCTTCCACCAGTA-3'
```

The reaction product, 1 μL, of the PCR above was analyzed using a Bioanalyzer (manufactured by Agilent Technologies, Inc.).

The polynucleotide level "A" of the band with exon 45 skipping and the polynucleotide level "B" of the band without exon 45 skipping were measured. Based on these measurement values of "A" and "B", the skipping efficiency was determined by the following equation:

Skipping efficiency(%)=$A/(A+B)\times 100$

Experimental Results

Figure 3:
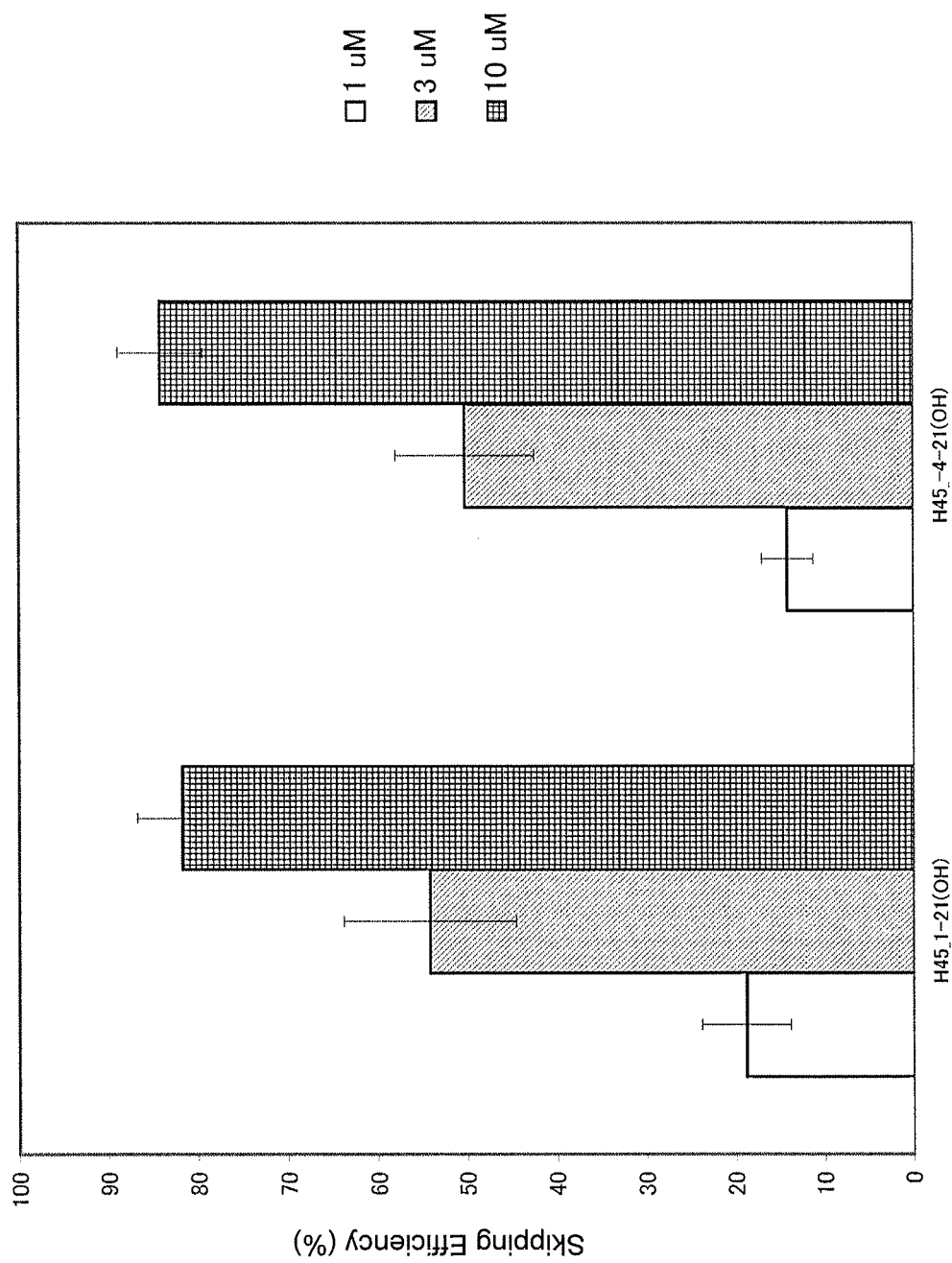
FIG. 3 shows the efficiency of exon 45 skipping by PMO in the human dystrophin gene in human rhabdomyosarcoma cell line (RD cells).
Figure 4:
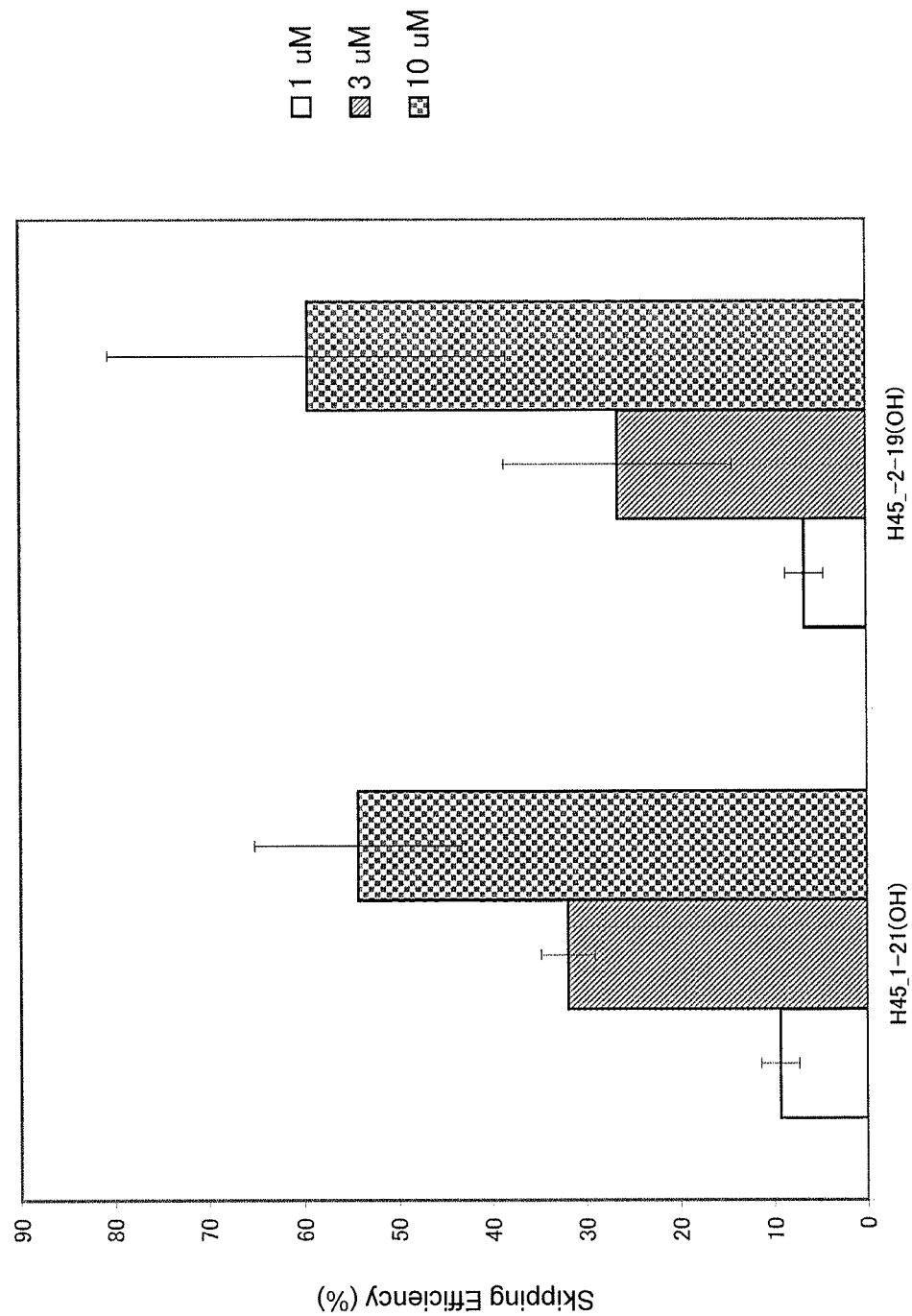
FIG. 4 shows the efficiency of exon 45 skipping by PMO in the human dystrophin gene in human rhabdomyosarcoma cell line (RD cells).
Figure 14:
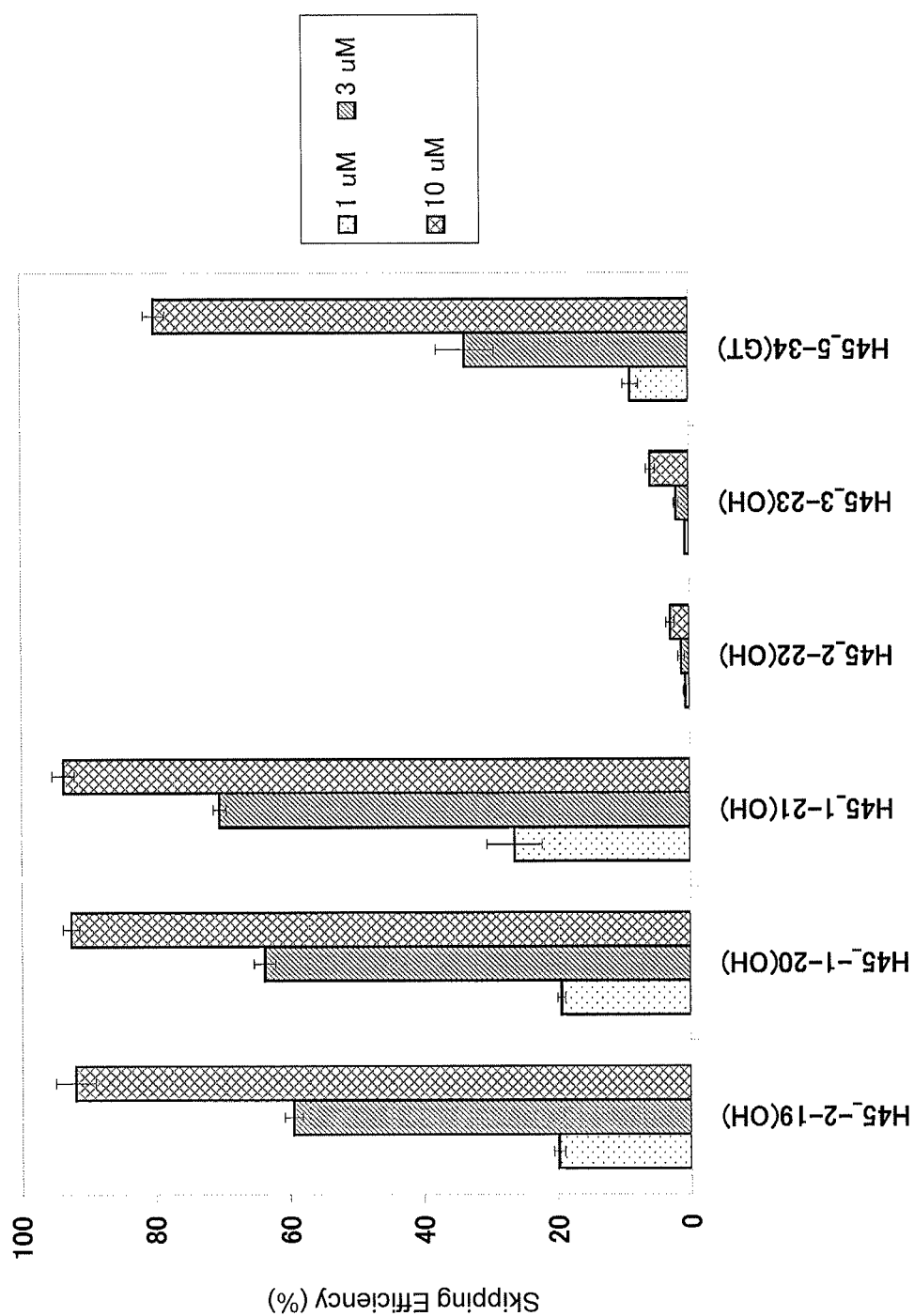
FIG. 14 shows the efficiency of exon 45 skipping by PMO in the human dystrophin gene in human rhabdomyosarcoma cell line (RD cells).
Figure 15:
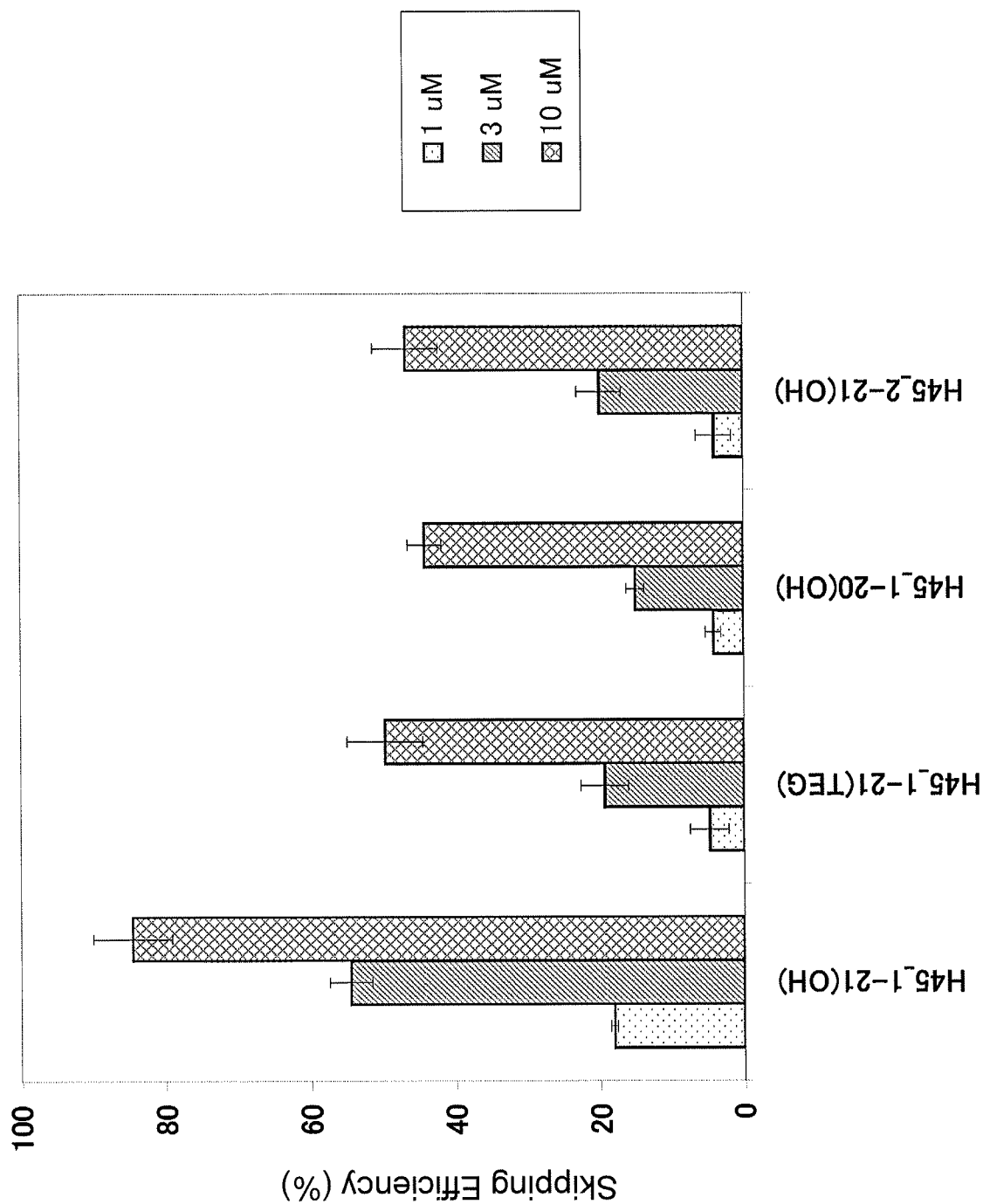
FIG. 15 shows the efficiency of exon 45 skipping by PMO in the human dystrophin gene in human rhabdomyosarcoma cell line (RD cells).

The results are shown in FIGS. 3, 4, 14 and 15. These experiments revealed that the oligomers PMO Nos. 1 and 3 of the present invention caused exon 45 skipping with a equivalent efficiency to the antisense oligomer PMO No. 6 in RD cells (FIG. 3, 4). In addition, the experiments revealed that the oligomers PMO Nos. 1, 2 and 3 of the present invention caused exon 45 skipping with a higher efficiency than the antisense oligomer PMO No. 7 (FIG. 14). Furthermore, the experiments revealed that the oligomer PMO No. 3 caused exon 45 skipping with a higher efficiency than the antisense oligomer PMO No. 10 whose end structure is different from that of PMO No. 3 (FIG. 15).

Test Example 3

In Vitro Assay Using Human Fibroblasts

Human myoD gene (SEQ ID NO: 38) was introduced into the GM05017 cells (human DMD-patient derived fibroblasts, Coriell Institute for Medical Research) using a ZsGreen1 coexpression retroviral vector.

After incubation for 4 to 5 days, ZsGreen-positive MyoD-transformed fibroblasts were collected by FACS and plated at $5\times10^4/cm^2$ into a 12-well plate. As a growth medium, there was used 1 mL of Dulbecco's Modified Eagle Medium:Nutrient Mixture F-12 (DMEM•F-12) (Invitrogen Corp.) containing 10% FCS and 1% Penicillin/Streptomycin (P/S) (Sigma-Aldrich, Inc).

The medium was replaced 24 hours later by a differentiation medium (DMEM/F-12 containing 2% equine serum (Invitrogen Corp.), 1% P/S and ITS Liquid Media Supplement (Sigma, Inc.)). The medium was exchanged every 2 to 3 days and incubation was continued for 12 to 14 days to differentiate into myotubes.

Subsequently, the differentiation medium was replaced by a differentiation medium containing 6 μM Endo-Porter (Gene Tools), and a morpholino oligomer was added thereto at a final concentration of 10 μM. After incubation for 48 hours, total RNA was extracted from the cells using a TRIzol (manufactured by Invitrogen Corp.). RT-PCR was performed with 50 ng of the extracted total RNA using a QIAGEN OneStep RT-PCR Kit. A reaction solution was prepared in accordance with the protocol attached to the kit. An iCycler (manufactured by Bio-Rad) was used as a thermal cycler. The RT-PCR program used is as follows.

50° C., 30 mins: reverse transcription
95° C., 15 mins: thermal denaturation
[94° C., 1 mins; 60° C., 1 mins; 72° C., 1 mins]xx 35 cycles: PCR amplification
72° C., 7 mins: thermal inactivation of polymerase The primers used were hDMD44F and hDMD46R.

```
                                    (SEQ ID NO: 39)
hDMD44F:    5'-CCTGAGAATTGGGAACATGC-3'

(SEQ ID NO: 40)
hDMD46R:    5'- TTGCTGCTCTTTTCCAGGTT-3'
```

The reaction product of RT-PCR above was separated by 2% agarose gel electrophoresis and gel images were captured with a GeneFlash (Syngene). The polynucleotide level "A" of the band with exon 45 skipping and the polynucleotide level "B" of the band without exon 45 skipping were measured using an Image J (manufactured by National Institutes of Health). Based on these measurement values of "A" and "B," the skipping efficiency was determined by the following equation.

Skipping efficiency(%)=$A/(A+B)\times 100$

Experimental Results

Figure 5:
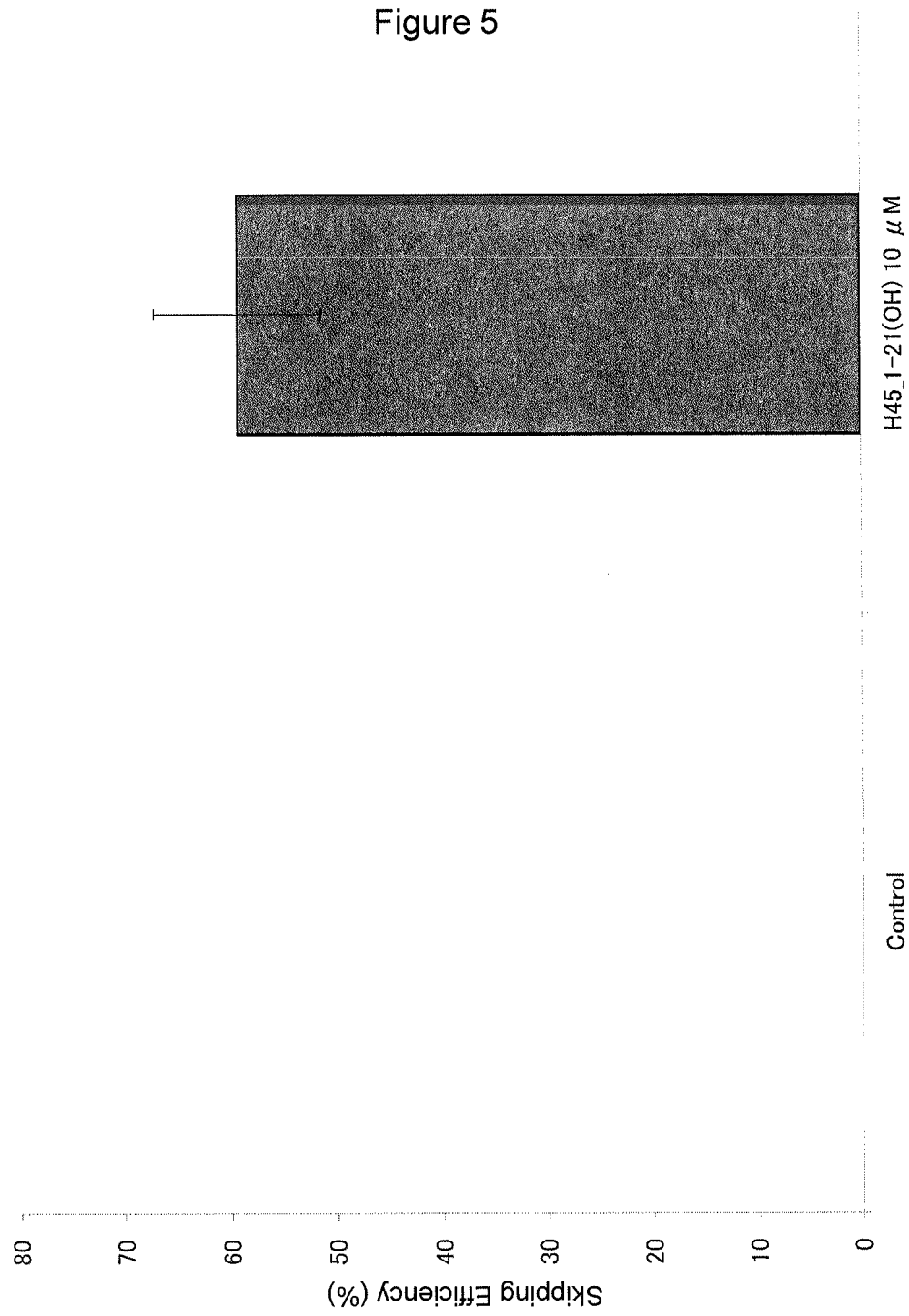
FIG. 5 shows the efficiency of exon 45 skipping by PMO in the human dystrophin gene in the cells where human MyoD gene is induced into fibroblasts from human DMD patient (GM05017 cells) to induce differentiation into muscle cells.

The results are shown in FIG. 5. This experiment revealed that the oligomer PMO Nos. 3 of the present invention caused exon 45 skipping with a high efficiency in GM05017 cells.

EXON 55

According to the descriptions in EXAMPLES 9 to 19 below, various types of PMO shown by PMO Nos. 11-14 and 16-22 in TABLE 11 were synthesized. The PMO synthesized was dissolved in water for injection (manufactured by Otsuka Pharmaceutical Factory, Inc.). PMO No. 15 was purchased from Gene Tools, LLC.

TABLE 11

| PMO No. | Sequence name | Note | SEQ ID NO: |
|---|---|---|---|
| 11 | H55_2-22 (OH) | 5' end: group (3) | 41 |
| 12 | H55_8-28 (OH) | 5' end: group (3) | 42 |
| 13 | H55_11-31 (OH) | 5' end: group (3) | 43 |
| 14 | H55_14-34 (OH) | 5' end: group (3) | 44 |
| 15 | H55_139-156 (GT) | Sequence corresponding to h55AON6 in Patent Document 5, 5' end: group (2) | 115 |
| 16 | H55_12-32 (OH) | 5' end: group (3) | 45 |
| 17 | H55_13-33 (OH) | 5' end: group (3) | 46 |
| 18 | H55_15-35 (OH) | 5' end: group (3) | 47 |
| 19 | H55_16-36 (OH) | 5' end: group (3) | 48 |
| 20 | H55_14-33 (OH) | 5' end: group (3) | 116 |
| 21 | H55_15-34 (OH) | 5' end: group (3) | 117 |
| 22 | H55_14-34 (TEG) | 5' end: group (3) | 118 |

Example 9

PMO. No. 11

The title compound was produced in accordance with the procedure of EXAMPLE 1, except that 4-{[(2S,6R)-6-(6-benzamide prine-9-yl)-4-tritylmorpholin-2-yl]methoxy}-4-oxobutanoic acid loaded onto aminopolystyrene resin (REFERENCE EXAMPLE 4) was used as the starting material.

| ESI-TOF-MS | Clcd.: 6807.8 |
|---|---|
| | Found: 6807.0 |

Example 10

PMO. No. 12

The title compound was produced in accordance with the procedure of EXAMPLE 1, except that 4-(((2S,6R)-6-(5-methyl-2,4-dioxo-3,4-dihydropirimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6822.8 |
|---|---|
|  | Found: 6822.5 |

Example 11

PMO. No. 13

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6837.8 |
|---|---|
|  | Found: 6837.8 |

Example 12

PMO. No. 14

The title compound was produced in accordance with the procedure of EXAMPLE 1, except that 4-[[(2S,6R)-6-(6-benzamide prine-9-yl)-4-tritylmorpholin-2-yl]methoxy]-4-oxobutanoic acid loaded onto aminopolystyrene resin (REFERENCE EXAMPLE 4) was used as the starting material.

| ESI-TOF-MS | Clcd.: 6861.8 |
|---|---|
|  | Found: 6861.4 |

Example 13

PMO. No. 16

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6812.8 |
|---|---|
|  | Found: 6812.7 |

Example 14

PMO. No. 17

The title compound was produced in accordance with the procedure of EXAMPLE 1, except that 4-[[(2S,6R)-6-[6-(2-cyanoethoxy)-2-[(2-phenoxyacetyl)amino]purine-9-yl]-4-tritylmorpholin-2-yl]methoxy]-4-oxo-butanoic acid loaded onto aminopolystyrene resin (REFERENCE EXAMPLE 2) was used as the starting material.

| ESI-TOF-MS | Clcd.: 6852.8 |
|---|---|
|  | Found: 6852.7 |

Example 15

PMO. No. 18

The title compound was produced in accordance with the procedure of EXAMPLE 1, except that 4-[[(2S,6R)-6-[6-(2-cyanoethodxy)-2-[(2-phenoxyacetyl)amino]purine-9-yl]-4-tritylmorpholin-2-yl]methoxy]-4-oxo-butanoic acid loaded onto aminopolystyrene resin (REFERENCE EXAMPLE 2) was used as the starting material.

| ESI-TOF-MS | Clcd.: 6901.8 |
|---|---|
|  | Found: 6901.5 |

Example 16

PMO. No. 19

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6901.8 |
|---|---|
|  | Found: 6901.7 |

Example 17

PMO. No. 20

The title compound was produced in accordance with the procedure of EXAMPLE 1, except that 4-[[(2S,6R)-6-[6-(2-Cyanoethoxy)-2-[(2-phenoxyacetyl)amino]purine-9-yl]-4-tritylmorpholin-2-yl]methoxy]-4-oxo-butanoic acid loaded onto aminopolystyrene resin (REFERENCE EXAMPLE 2) was used as the starting material.

| ESI-TOF-MS | Clcd.: 6522.5 |
|---|---|
|  | Found: 6522.0 |

Example 18

PMO. No. 21

The title compound was produced in accordance with the procedure of EXAMPLE 1, except that 4-{[(2S,6R)-6-(6-benzamide prine-9-yl)-4-tritylmorpholin-2-yl]methoxy}-4-oxobutanoic acid loaded onto aminopolystyrene resin (REFERENCE EXAMPLE 4) was used as the starting material.

| ESI-TOF-MS | Clcd.: 6546.5 |
|---|---|
|  | Found: 6546.0 |

Example 19

PMO. No. 22

The title compound was produced in accordance with the procedure of EXAMPLE 1, except that 1,12-dioxo-1-(4-tritylpiperazin-1-yl)-2,5,8,11-tetraoxa-15-pentadecanoic acid (REFERENCE EXAMPLE 5) loaded onto aminopolystyrene resin was used as the starting material.

| ESI-TOF-MS | Clcd.: 7213.1 |
|---|---|
|  | Found: 7212.5 |

Test Example 4

In Vitro Assay

Experiments were performed using the antisense oligomers of 2'-O-methoxy-phosphorothioates (2'-OMe-S-RNA) shown by SEQ ID NO: 49 to SEQ ID NO: 68. Various antisense oligomers used for the assay were purchased from Japan Bio Services. The sequences of various antisense oligomers are given below.

TABLE 12

| Antisense oligomer | Nucleotide sequence | SEQ ID NO: |
|---|---|---|
| H55_1-21 | GCAGCCUCUCGCUCACUCACC | 49 |
| H55_6-26 | CCAAAGCAGCCUCUCGCUCAC | 50 |
| H55_11-31 | UUCUUCCAAAGCAGCCUCUCG | 51 |
| H55_21-41 | AUCUAUGAGUUUCUUCCAAAG | 52 |
| H55_31-51 | UGUUGCAGUAAUCUAUGAGUU | 53 |
| H55_41-61 | CAGGGGGAACUGUUGCAGUAA | 54 |
| H55_51-71 | UUUCCAGGUCCAGGGGGAACU | 55 |
| H55_61-81 | GCAAGAAACUUUUCCAGGUCC | 56 |
| H55_71-91 | UGUAAGCCAGGCAAGAAACUU | 57 |
| H55_81-101 | UUUCAGCUUCUGUAAGCCAGG | 58 |
| H55_91-111 | UUGGCAGUUGUUUCAGCUUCU | 59 |
| H55_101-121 | CUGUAGGACAUUGGCAGUUGU | 60 |
| H55_111-131 | GGGUAGCAUCCUGUAGGACAU | 61 |
| H55_121-141 | CUUUCCUUACGGGUAGCAUCC | 62 |
| H55_131-151 | UUCUAGGAGCCUUUCCUUACG | 63 |
| H55_141-161 | CCUUGGAGUCUUCUAGGAGCC | 64 |
| H55_151-171 | UCUUUUACUCCCUUGGAGUCU | 65 |
| H55_161-181 | UUUCAUCAGCUCUUUUACUCC | 66 |
| H55_171-190 | UUGCCAUUGUUUCAUCAGCU | 67 |
| H55_104-123 | UCCUGUAGGACAUUGGCAGU | 68 |

Experiments were performed in accordance with the condition and the procedure of Exon 45 (TEST EXAMPLE 1), except that the RT-PCR was performed using the primers below.

Forward primer:
(SEQ ID NO: 69)
5'- CATGGAAGGAGGGTCCCTAT-3'

Reverse primer:
(SEQ ID NO: 70)
5'- CTGCCGGCTTAATTCATCAT-3'

Experimental Results

Figure 6:
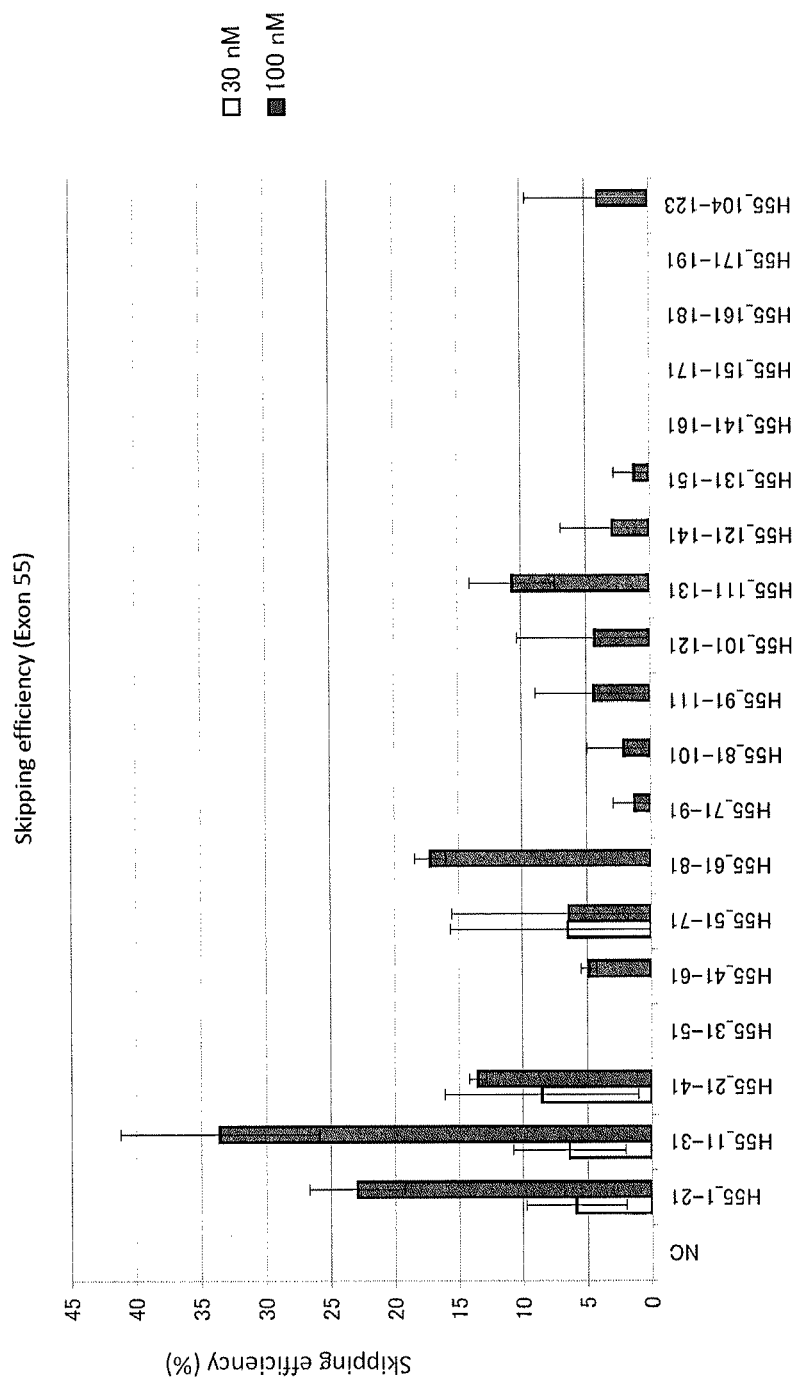
FIG. 6 shows the efficiency of exon 55 skipping by 2'-OMe-S-RNA oligomer in the human dystrophin gene in human rhabdomyosarcoma cell line (RD cells).
Figure 7:
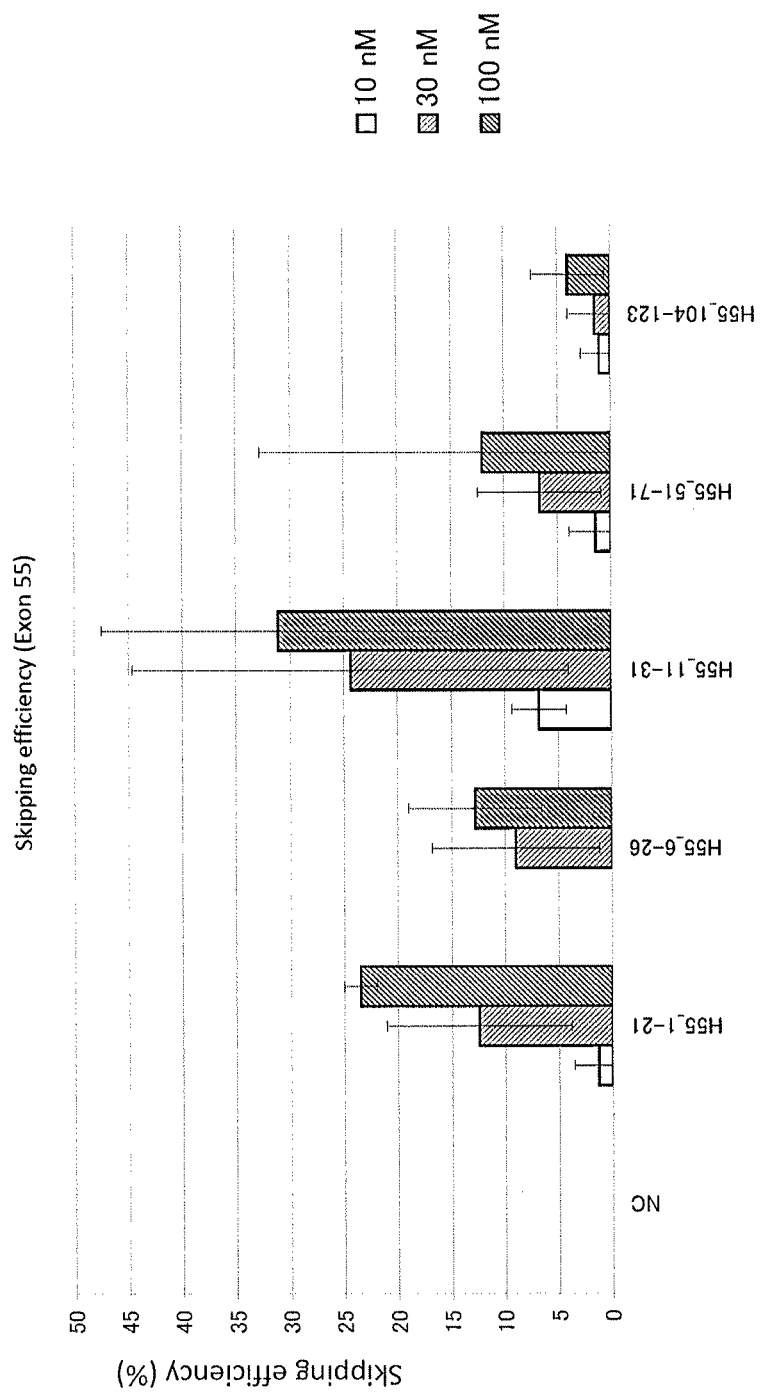
FIG. 7 shows the efficiency of exon 55 skipping by 2'-OMe-S-RNA oligomer in the human dystrophin gene in human rhabdomyosarcoma cell line (RD cells).

The results are shown in FIGS. 6 and 7. These experiments revealed that, when the antisense oligomers were designed at the 1st to the 21st, or the 11th to the 31st nucleotides from the 5' end of exon 55 in the human dystrophin gene, exon 55 skipping of these antisense oligomers could be caused with a higher efficiency than that of the antisense oligomer which is designed at the 104th to the 123rd nucleotides from the 5' end of exon 55.

Test Example 5

In Vitro Assay

Experiments were performed in accordance with the condition and the procedure of exon 45 (TEST EXAMPLE 2), except that the RT-PCR was performed using the primers below.

Forward primer:
(SEQ ID NO: 69)
5'- CATGGAAGGAGGGTCCCTAT-3'

Reverse primer:
(SEQ ID NO: 70)
5'- CTGCCGGCTTAATTCATCAT-3'

Experimental Results

Figure 8:
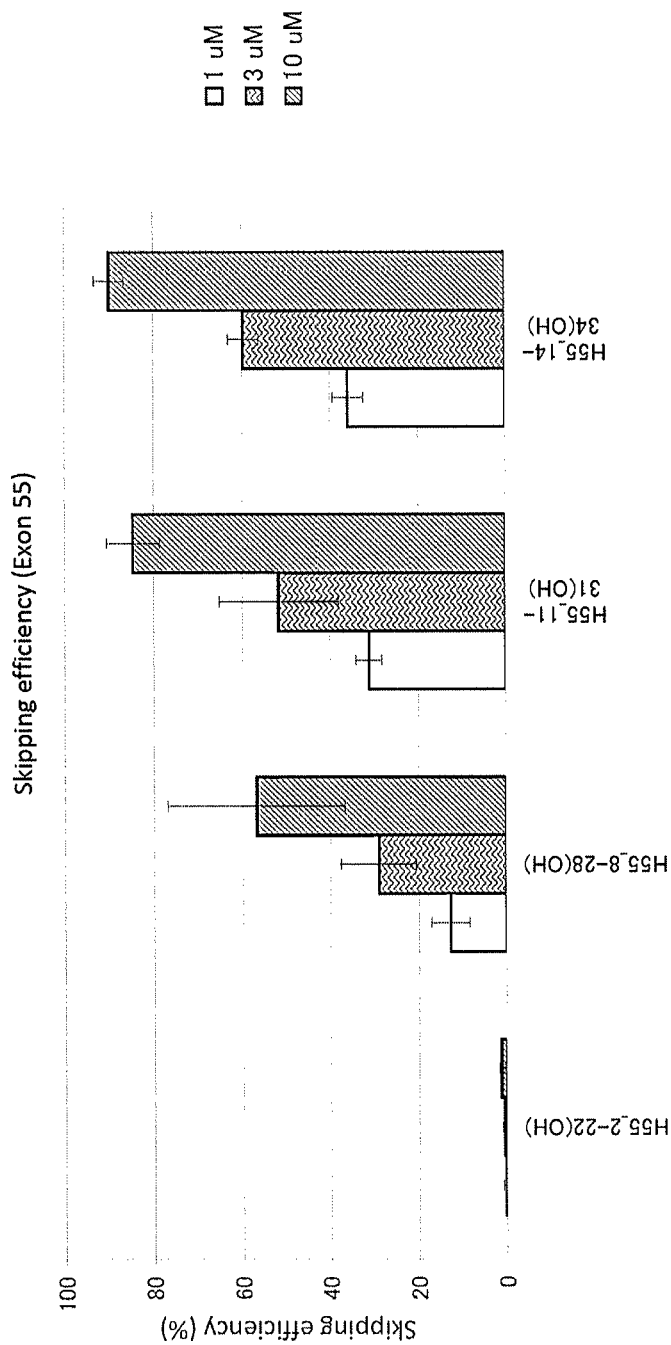
FIG. 8 shows the efficiency of exon 55 skipping by PMO in the human dystrophin gene in human rhabdomyosarcoma cell line (RD cells).
Figure 16:
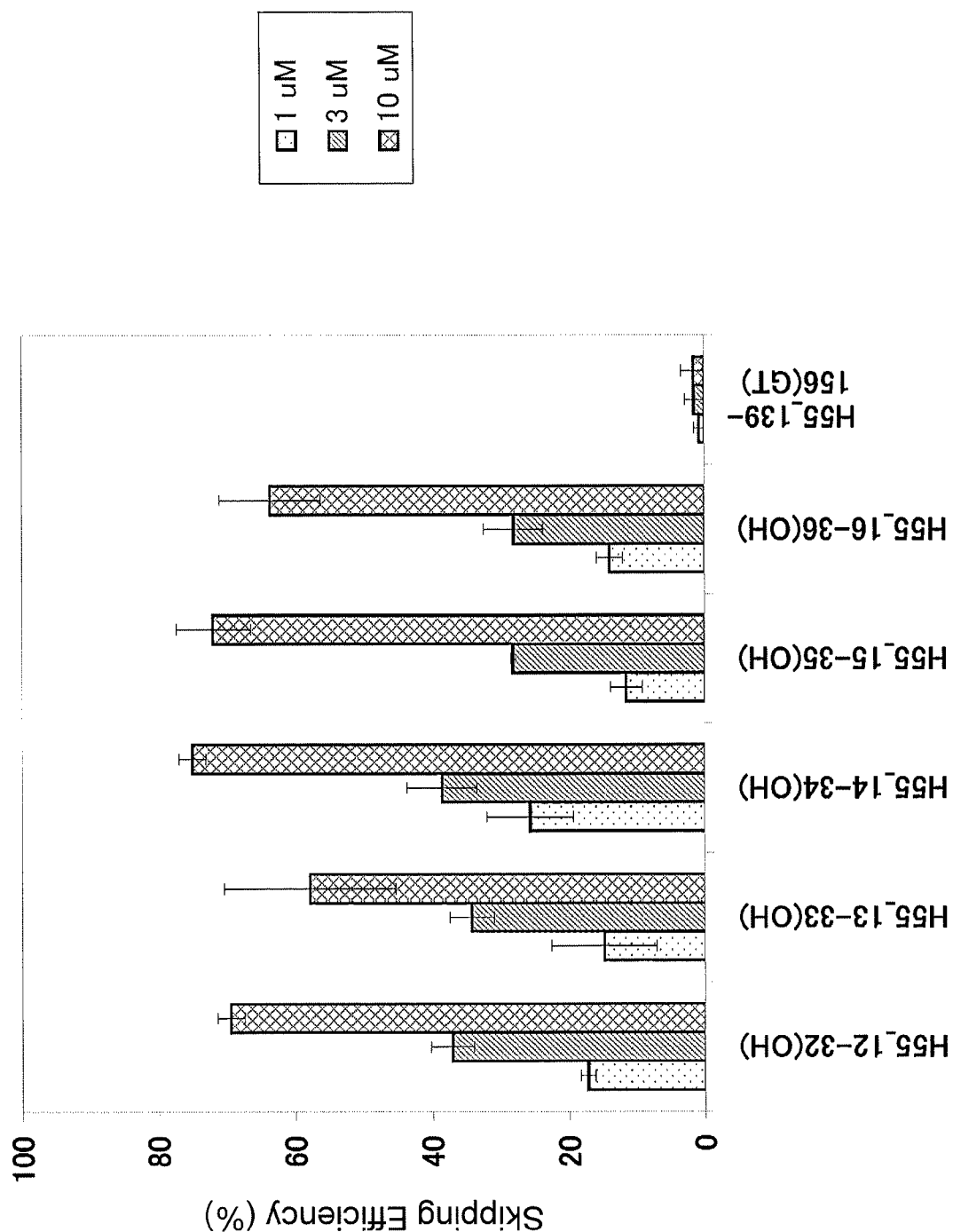
FIG. 16 shows the efficiency of exon 55 skipping by PMO in the human dystrophin gene in human rhabdomyosarcoma cell line (RD cells).
Figure 17:
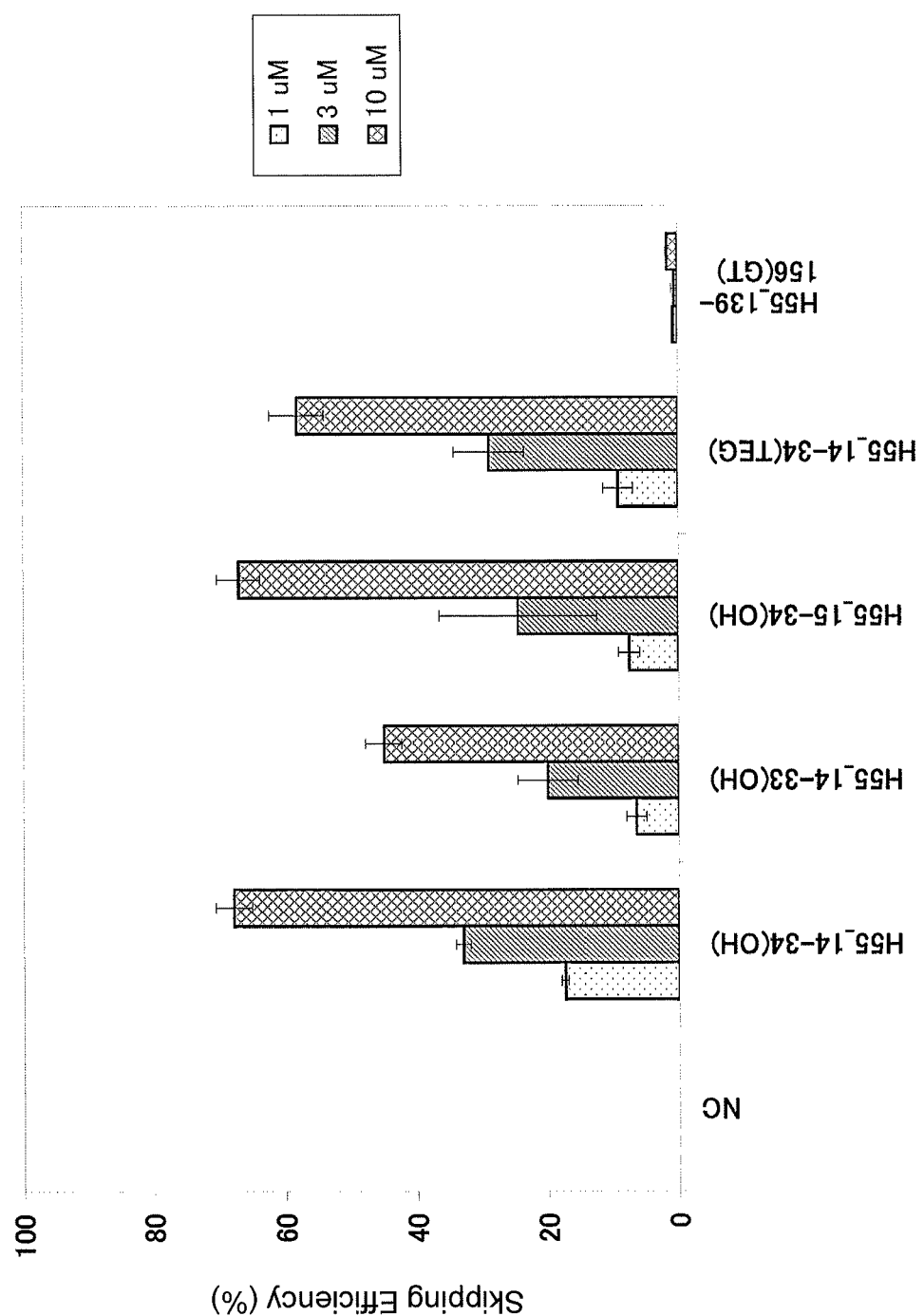
FIG. 17 shows the efficiency of exon 55 skipping by PMO in the human dystrophin gene in human rhabdomyosarcoma cell line (RD cells).

The results are shown in FIGS. 8, 16 and 17. These experiments revealed that in RD cells, the oligomers PMO Nos. 12, 13 and 14 (H55_8-28 (OH), H55_11-31 (OH) and H55_14-34 (OH)) of the present invention all caused exon 55 skipping with a high efficiency (FIG. 8). Also, the oligomers PMO Nos. 14, 16, 17, 18 and 19 (H55_14-34 (OH), H55_12-32 (OH), H55_13-33 (OH), H55_15-35 (OH) and H55_16-36 (OH)) of the present invention were found to cause exon 55 skipping with a notably higher efficiency than that of the antisense oligomer PMO No. 15 (H55_139-156 (GT)) in RD cells (FIG. 16). The oligomer PMO No. 14 of the present invention and the oligomer PMO No. 21 (H55_15-34(OH)), which is one base shorter than the oligomer PMO No. 14, were found to cause exon 55 skipping with the same efficiency (FIG. 17). Furthermore, the experiments revealed that the oligomer PMO No. 14 of the present invention caused exon 55 skipping with the same efficiency as the oligomer PMO No. 22 (H55_14-34 (TEG)), which has a different end structure from that of the oligomer PMO No. 14 (FIG. 17).

EXON 44

According to the descriptions in EXAMPLES 20 to 29 below, various types of PMO shown by PMO Nos. 23-29 and 31-33 in TABLE below were synthesized. The PMO synthesized was dissolved in water for injection (manufactured by Otsuka Pharmaceutical Factory, Inc.). PMO No. 30 was purchased from Gene Tools, LLC.

TABLE 13

| PMO No. | Sequence name | Note | SEQ ID NO: |
|---|---|---|---|
| 23 | H44_23-43 (OH) | 5' end: group (3) | 71 |
| 24 | H44_25-45 (OH) | 5' end: group (3) | 72 |
| 25 | H44_26-46 (OH) | 5' end: group (3) | 73 |
| 26 | H44_27-47 (OH) | 5' end: group (3) | 74 |
| 27 | H44_28-48 (OH) | 5' end: group (3) | 75 |
| 28 | H44_29-49 (OH) | 5' end: group (3) | 76 |
| 29 | H44_30-50 (OH) | 5' end: group (3) | 77 |
| 30 | H44_10-39 (GT) | Sequence corresponding to SEQ ID NO: 1 in Patent Document 3, 5' end: group (2) | 78 |
| 31 | H44_27-46 (OH) | 5' end: group (3) | 79 |
| 32 | H44_28-47 (OH) | 5' end: group (3) | 80 |
| 33 | H44_27-47 (TEG) | 5' end: group (1) | 81 |

Example 20

PMO. No. 23

The title compound was produced in accordance with the procedure of EXAMPLE 1, except that 4-(((2S,6R)-6-(5-methyl-2,4-dioxo-3,4-dihydropyrimidin-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6918.9 |
|---|---|
| | Found: 6918.3 |

Example 21

PMO. No. 24

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6903.9 |
|---|---|
| | Found: 6904.2 |

Example 22

PMO. No. 25

The title compound was produced in accordance with the procedure of EXAMPLE 1, except that 4-{[(2S,6R)-6-(6-benzamide prine-9-yl)-4-tritylmorpholin-2-yl}methoxy]-4-oxobutanoic acid loaded onto aminopolystyrene resin (REFERENCE EXAMPLE 4) was used as the starting material.

| ESI-TOF-MS | Clcd.: 6912.9 |
|---|---|
| | Found: 6912.4 |

Example 23

PMO. No. 26

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6903.9 |
|---|---|
| | Found: 6904.2 |

Example 24

PMO. No. 27

The title compound was produced in accordance with the procedure of EXAMPLE 1, except that 4-{[(2S,6R)-6-(6-benzamide prine-9-yl)-4-tritylmorpholin-2-yl]methoxy}-4-oxobutanoic acid loaded onto aminopolystyrene resin (REFERENCE EXAMPLE 4) was used as the starting material.

| ESI-TOF-MS | Clcd.: 6927.9 |
|---|---|
| | Found: 6927.4 |

Example 25

PMO. No. 28

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6942.9 |
|---|---|
| | Found: 6942.3 |

Example 26

PMO. No. 29

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6917.9 |
|---|---|
| | Found: 6918.3 |

Example 27

PMO. No. 31

The title compound was produced in accordance with the procedure of EXAMPLE 1, except that 4-{[(2S,6R)-6-(6-benzamide prine-9-yl)-4-tritylmorpholin-2-yl]methoxy}-4-oxobutanoic acid loaded onto aminopolystyrene resin (REFERENCE EXAMPLE 4) was used as the starting material.

| ESI-TOF-MS | Clcd.: 6573.6 |
| --- | --- |
| | Found: 6572.4 |

Example 28

PMO. No. 32

The title compound was produced in accordance with the procedure of EXAMPLE 1, except that 4-(((2S,6R)-6-(5-methyl-2,4-dioxo-3,4-dihydropyrimidine-1(2H)-yl)-4-trityl-morpholin-2-yl)methoxy)-4-oxobutanoic acid loaded onto aminopolystyrene resin (REFERENCE EXAMPLE 3) was used as the starting material.

| ESI-TOF-MS | Clcd.: 6588.6 |
| --- | --- |
| | Found: 6588.3 |

Example 29

PMO. No. 33

The title compound was produced in accordance with the procedure of EXAMPLE 1, except that 1,12-dioxo-1-(4-tritylpiperazin-1-yl)-2,5,8,11-tetraoxa-15-pentadecanoic acid loaded onto aminopolystyrene resin (REFERENCE EXAMPLE 5) was used as the starting material.

| ESI-TOF-MS | Clcd.: 7255.2 |
| --- | --- |
| | Found: 7254.7 |

Test Example 6

In Vitro Assay

Experiments were performed using the antisense oligomers of 2'-O-methoxy-phosphorothioates (2'-OMe-S-RNA) shown by SEQ ID NO: 82 to SEQ ID NO: 95 and SEQ ID NO: 109 to SEQ ID NO: 118. Various antisense oligomers used for the assay were purchased from Japan Bio Services. The sequences of various antisense oligomers are given below.

TABLE 14

| Antisense oligomer | Nucleotide sequence | SEQ ID NO: |
| --- | --- | --- |
| H44_1-22 | CUCAACAGAUCUGUCAAAUCGC | 82 |
| H44_6-27 | CAUUUCUCAACAGAUCUGUCAA | 105 |
| H44_11-32 | GCCGCCAUUUCUCAACAGAUCU | 83 |
| H44_16-37 | AAAACGCCGCCAUUUCUCAACA | 106 |
| H44_21-42 | UAAUGAAAACGCCGCCAUUUCU | 84 |
| H44_26-47 | UAUCAUAAUGAAAACGCCGCCA | 85 |
| H44_31-52 | CUUUAUAUCAUAAUGAAAACGC | 86 |
| H44_36-57 | AAUAUCUUUAUAUCAUAAUGAA | 107 |
| H44_41-62 | GAUUAAAUAUCUUUAUAUCAUA | 87 |
| H44_51-72 | GUUAGCCACUGAUUAAAUAUCU | 88 |

TABLE 14-continued

| Antisense oligomer | Nucleotide sequence | SEQ ID NO: |
| --- | --- | --- |
| H44_56-77 | CUUCUGUUAGCCACUGAUUAAA | 108 |
| H44_61-82 | UUCAGCUUCUGUUAGCCACUGA | 89 |
| H44_66-87 | AACUGUUCAGCUUCUGUUAGCC | 109 |
| H44_71-92 | UGAGAAACUGUUCAGCUUCUGU | 90 |
| H44_76-97 | CUUUCUGAGAAACUGUUCAGCU | 110 |
| H44_81-102 | UGUGUCUUUCUGAGAAACUGUU | 91 |
| H44_86-107 | GAAUUUGUGUCUUUCUGAGAAA | 111 |
| H44_91-112 | CUCAGGAAUUUGUGUCUUUCUG | 112 |
| H44_96-117 | CAAUUCUCAGGAAUUUGUGUCU | 113 |
| H44_101-122 | GUUCCCAAUUCUCAGGAAUUUG | 92 |
| H44_106-127 | AGCAUGUUCCCAAUUCUCAGGA | 114 |
| H44_111-132 | UAUUUAGCAUGUUCCCAAUUCU | 93 |
| H44_121-142 | AUACCAUUUGUAUUUAGCAUGU | 94 |
| H44_62-81 | UCAGCUUCUGUUAGCCACUG | 95 |

Experiments were performed in accordance with the condition and the procedure of exon 45 (TEST EXAMPLE 1).

Experimental Results

Figure 9:
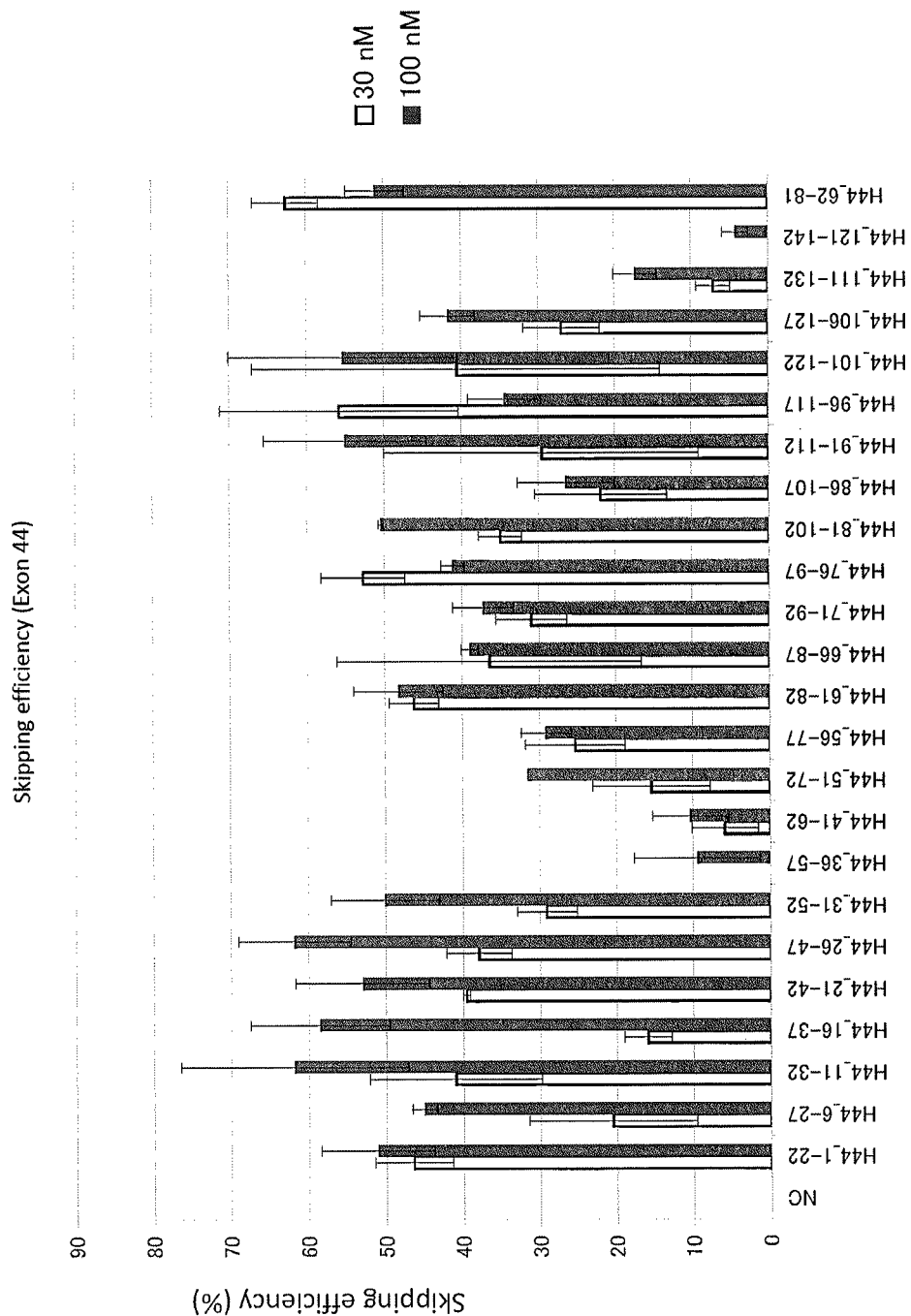
FIG. 9 shows the efficiency of exon 44 skipping by 2'-OMe-S-RNA oligomer in the human dystrophin gene in human rhabdomyosarcoma cell line (RD cells).
Figure 10:
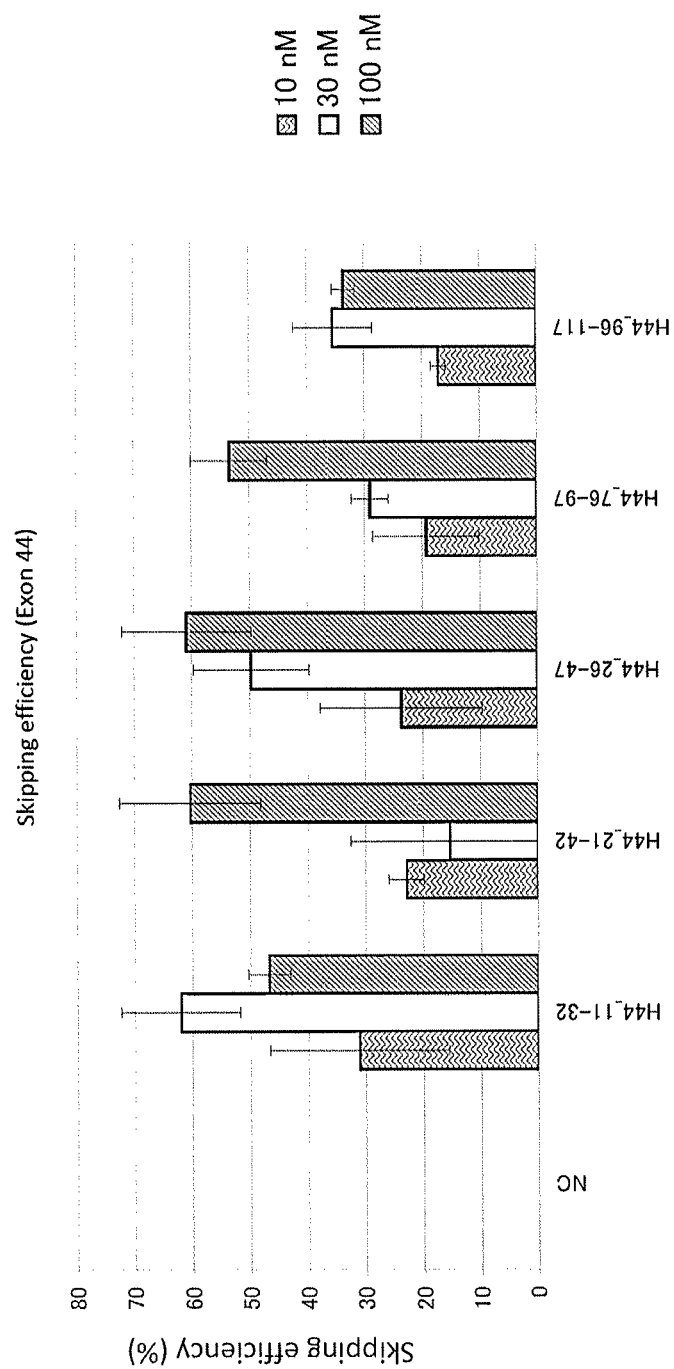
FIG. 10 shows the efficiency of exon 44 skipping by 2'-OMe-S-RNA oligomer in the human dystrophin gene in human rhabdomyosarcoma cell line (RD cells).

The results are shown in FIGS. 9 and 10. These experiments revealed that, when the antisense oligomers were designed at the 11th to the 32nd, or the 26th to the 47th nucleotides from the 5' end of exon 44 in the human dystrophin gene, exon 44 skipping of these antisense oligomer could be caused with the same efficiency with that of the antisense oligomer which is designed at the 62nd to the 81st nucleotides from the 5' end of exon 44.

Test Example 7

In Vitro Assay

Experiments were performed in accordance with the condition and the procedure of exon 45 (TEST EXAMPLE 2).

Experimental Results

Figure 11:
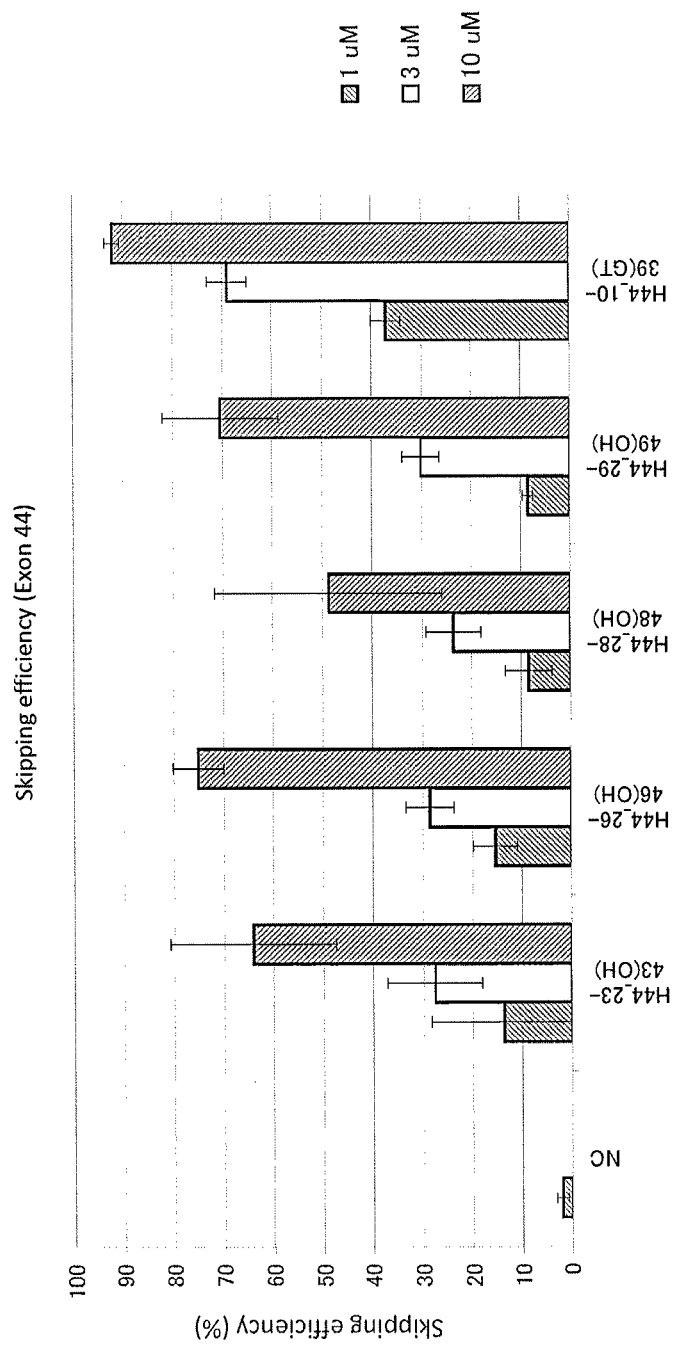
FIG. 11 shows the efficiency of exon 44 skipping by PMO in the human dystrophin gene in human rhabdomyosarcoma cell line (RD cells).
Figure 12:
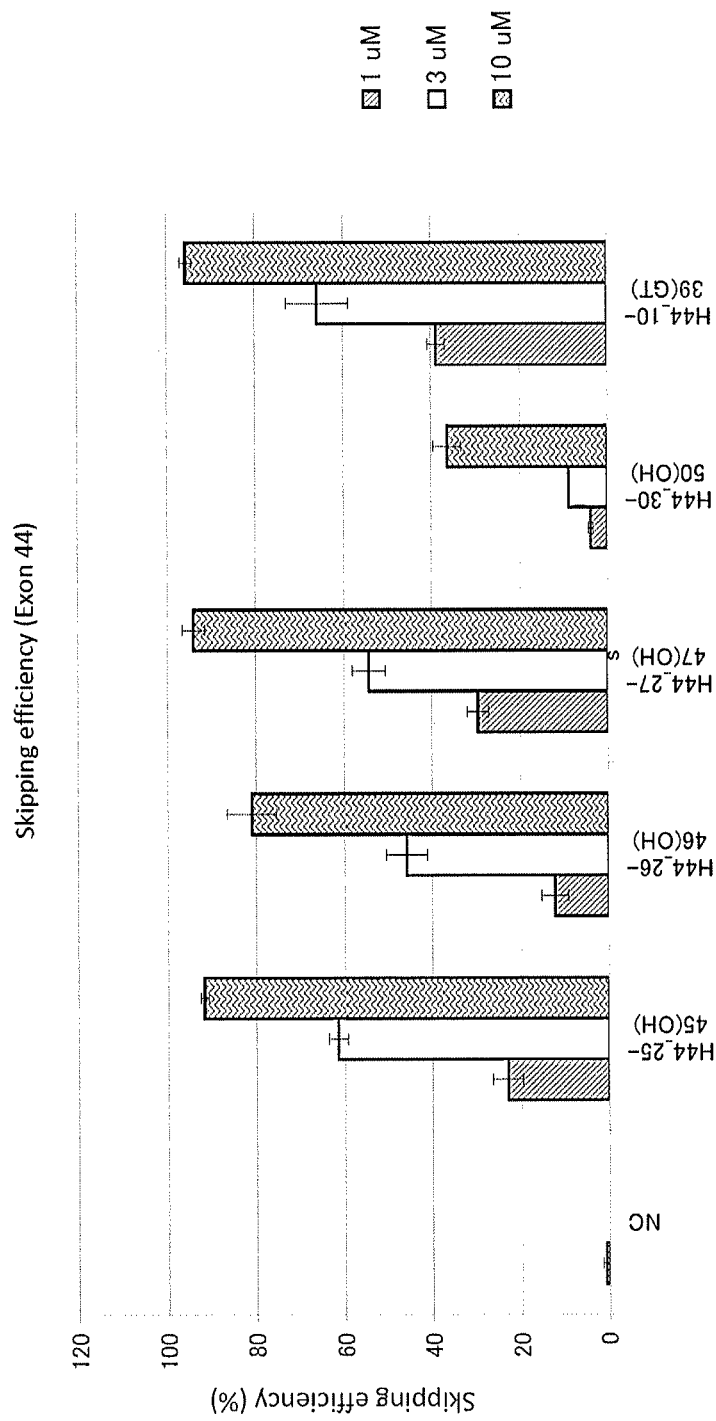
FIG. 12 shows the efficiency of exon 44 skipping by PMO in the human dystrophin gene in human rhabdomyosarcoma cell line (RD cells).
Figure 18:
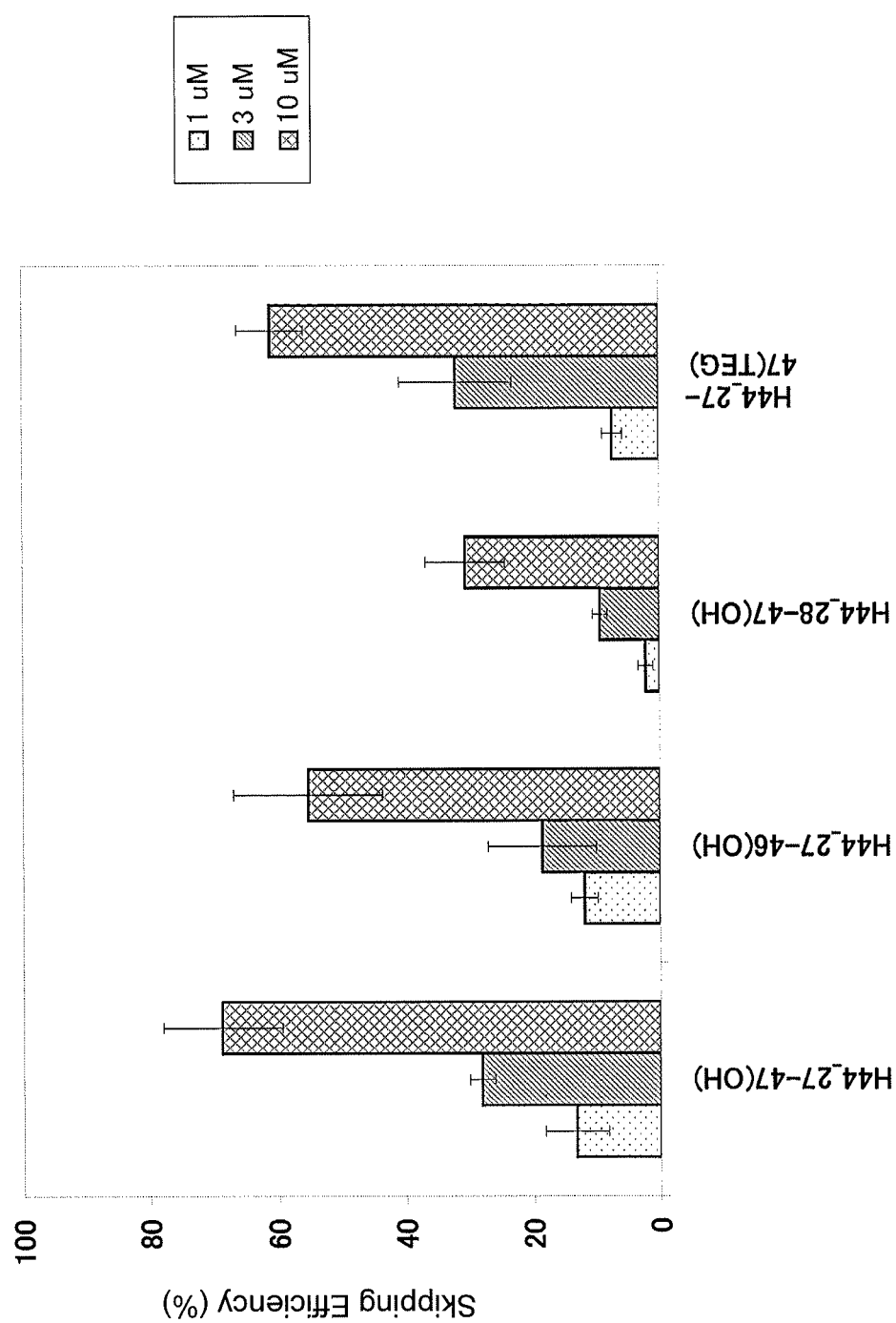
FIG. 18 shows the efficiency of exon 44 skipping by PMO in the human dystrophin gene in human rhabdomyosarcoma cell line (RD cells).

The results are shown in FIGS. 11, 12 and 18. This experiment revealed that in RD cells, the oligomers PMO No. 24 and 26 (H44_25-45 (OH) and H44_27-47 (OH)) of the present invention caused exon 44 skipping with the same efficiency as the antisense oligomer PMO No. 30 (H44_10-39(OH)) (FIG. 11, 12). The oligomer PMO No. 26 of the present invention and the oligomer PMO No. 31 (H44_27-46(OH)), which is one base shorter than the oligomer PMO No. 26, were found to cause exon 44 skipping with the same efficiency (FIG. 18). Furthermore, the oligomer PMO No. 26 of the present invention was found to cause exon 44 skipping with the same efficiency as the oligomer PMO No. 33 (H44_27-47 (TEG)), which has a different end structure from the oligomer PMO No. 26 (FIG. 18).

EXON 50

According to the descriptions in EXAMPLES 30 to 39 below, various types of PMO shown by PMO Nos. 34-38 and 41-45 in TABLE 15 were synthesized. The PMO synthesized was dissolved in water for injection (manufactured by Otsuka Pharmaceutical Factory, Inc.). PMO Nos. 39 and 40 were purchased from Gene Tools, LLC.

TABLE 15

| PMO No. | Sequence name | Note | SEQ ID NO: |
|---|---|---|---|
| 34 | H50_103-123(OH) | 5' end: group (3) | 96 |
| 35 | H50_104-124(OH) | 5' end: group (3) | 97 |
| 36 | H50_105-125(OH) | 5' end: group (3) | 98 |
| 37 | H50_106-126(OH) | 5' end: group (3) | 99 |
| 38 | H50_107-127(OH) | 5' end: group (3) | 100 |
| 39 | H50_90-114(GT) | Sequence corresponding to SEQ ID NO: 287 in Patent Document 4, 5' end: group (2) | 101 |
| 40 | H50_103-127(GT) | Sequence corresponding to SEQ ID NO: 175 in Patent Document 1, 5' end: group (2) | 102 |
| 41 | H50_107-126(OH) | 5' end: group (3) | 119 |
| 42 | H50_108-127(OH) | 5' end: group (3) | 120 |
| 43 | H50_108-128(OH) | 5' end: group (3) | 121 |
| 44 | H50_109-129(OH) | 5' end: group (3) | 122 |
| 45 | H50_107-127(TEG) | 5' end: group (1) | 100 |

Example 30

PMO. No. 34

The title compound was produced in accordance with the procedure of EXAMPLE 1, except that 4-{[(2S,6R)-6-(5-Methyl-2,4-dioxo-3,4-dihydropyrimidin-1-yl)-4-tritylmorpholin-2-yl]methoxy}-4-oxobutanoic acid loaded onto aminopolystyrene resin (REFERENCE EXAMPLE 3) was used as the starting material.

| ESI-TOF-MS | Clcd.: 6861.8 Found: 6861.8 |
|---|---|

Example 31

PMO. No. 35

The title compound was produced in accordance with the procedure of EXAMPLE 1, except that 4-{[(2S,6R)-6-(6-benzamideprine-9-yl)-4-tritylmorpholin-2-yl]methoxy}-4-oxobutanoic acid loaded onto aminopolystyrene resin (REFERENCE EXAMPLE 4) was used as the starting material.

| ESI-TOF-MS | Clcd.: 6885.8 Found: 6885.9 |
|---|---|

Example 32

PMO. No. 36

The title compound was produced in accordance with the procedure of EXAMPLE 1, except that 4-[[(2S,6R)-6-[6-(2-cyanoethoxy)-2-[(2-phenoxyacetyl)amino]purine-9-yl]-4-tritylmolphorin-2-yl]methoxy]-4-oxo-butanoic acid loaded onto aminopolystyrene resin (REFERENCE EXAMPLE 2) was used as the starting material.

| ESI-TOF-MS | Clcd.: 6925.9 Found: 6925.9 |
|---|---|

Example 33

PMO. No. 37

The title compound was produced in accordance with the procedure of EXAMPLE 1, except that 4-[[(2S,6R)-6-[6-(2-cyanoethoxy)-2-[(2-phenoxyacetyl)amino]purine-9-yl]-4-tritylmolphorin-2-yl]methoxy]-4-oxo-butanoic acid loaded onto aminopolystyrene resin (REFERENCE EXAMPLE 2) was used as the starting material.

| ESI-TOF-MS | Clcd.: 6950.9 Found: 6950.9 |
|---|---|

Example 34

PMO. No. 38

The title compound was produced in accordance with the procedure of EXAMPLE 1, except that 4-[[(2S,6R)-6-[6-(2-cyanoethoxy)-2-[(2-phenoxyacetyl)amino]purine-9-yl]-4-tritylmolphorin-2-yl]methoxy]-4-oxo-butanoic acid loaded onto aminopolystyrene resin (REFERENCE EXAMPLE 2) was used as the starting material.

| ESI-TOF-MS | Clcd.: 6990.9 Found: 6991.0 |
|---|---|

Example 35

PMO. No. 41

The title compound was produced in accordance with the procedure of EXAMPLE 1, except that 4-[[(2S,6R)-6-[6-(2-cyanoethoxy)-2-[(2-phenoxyacetyl)amino]purine-9-yl]-4-tritylmolphorin-2-yl]methoxy]-4-oxo-butanoic acid loaded onto aminopolystyrene resin (REFERENCE EXAMPLE 2) was used as the starting material.

| ESI-TOF-MS | Clcd.: 6635.6 Found: 6635.0 |
|---|---|

Example 36

PMO. No. 42

The title compound was produced in accordance with the procedure of EXAMPLE 1, except that 4-[[(2S,6R)-6-[6-(2-cyanoethoxy)-2-[(2-phenoxyacetyl)amino]purine-9-yl]-4-tritylmolphorin-2-yl]methoxy]-4-oxo-butanoic acid loaded onto aminopolystyrene resin (REFERENCE EXAMPLE 2) was used as the starting material.

| ESI-TOF-MS | Clcd.: 6635.6 Found: 6634.9 |
|---|---|

Example 37

PMO. No. 43

The title compound was produced in accordance with the procedure of EXAMPLE 1, except that 4-(((2S,6R)-6-(5-methyl-2,4-dioxo-3,4-dihydropyrimidine-1(2H)-yl)-4-tritylmorpholin-2-yl)methoxy)-4-oxobutanoic acid loaded onto aminopolystyrene resin (REFERENCE EXAMPLE 3) was used as the starting material.

| ESI-TOF-MS | Clcd.: 6965.9 |
| --- | --- |
| | Found: 6965.2 |

Example 38

PMO. No. 44

The title compound was produced in accordance with the procedure of EXAMPLE 1, except that 4-{[(2S,6R)-6-(6-benzamidepurine-9-yl)-4-tritylmorpholin-2-yl]methoxy}-4-oxobutanoic acid loaded onto aminopolystyrene resin (REFERENCE EXAMPLE 4) was used as the starting material.

| ESI-TOF-MS | Clcd.: 6949.9 |
| --- | --- |
| | Found: 6949.2 |

Example 39

PMO. No. 45

The title compound was produced in accordance with the procedure of EXAMPLE 1, except that 1,12-dioxo-1-(4-tritylpiperazin-1-yl)-2,5,8,11-tetraoxa-15-pentadecanoic acid loaded onto aminopolystyrene resin (REFERENCE EXAMPLE 5) was used as the starting material.

| ESI-TOF-MS | Clcd.: 7342.2 |
| --- | --- |
| | Found: 7341.6 |

Test Example 8

In Vitro Assay

Experiments were performed in accordance with the condition and the procedure of exon 45 (TEST EXAMPLE 2), except that the RT-PCR was performed using the primers below in the concentrations of 0.1, 0.3 or 1 µM.

```
Forward primer:
                              (SEQ ID NO: 103)
5'- AACAACCGGATGTGGAAGAG-3'

Reverse primer:
                              (SEQ ID NO: 104)
5'- TTGGAGATGGCAGTTTCCTT-3'
```

Experimental Results

Figure 13:
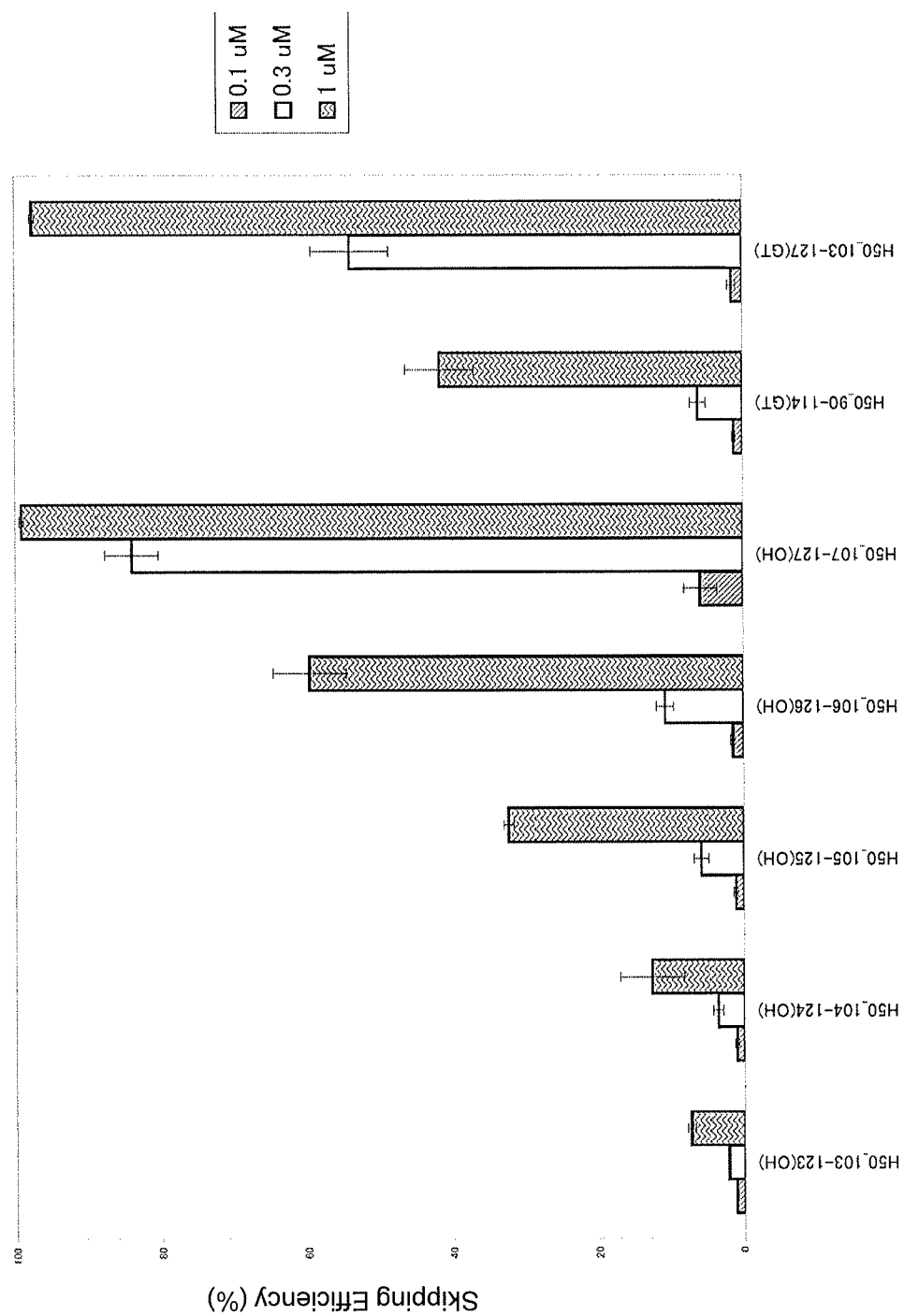
FIG. 13 shows the efficiency of exon 50 skipping by PMO in the human dystrophin gene in human rhabdomyosarcoma cell line (RD cells).
Figure 19:
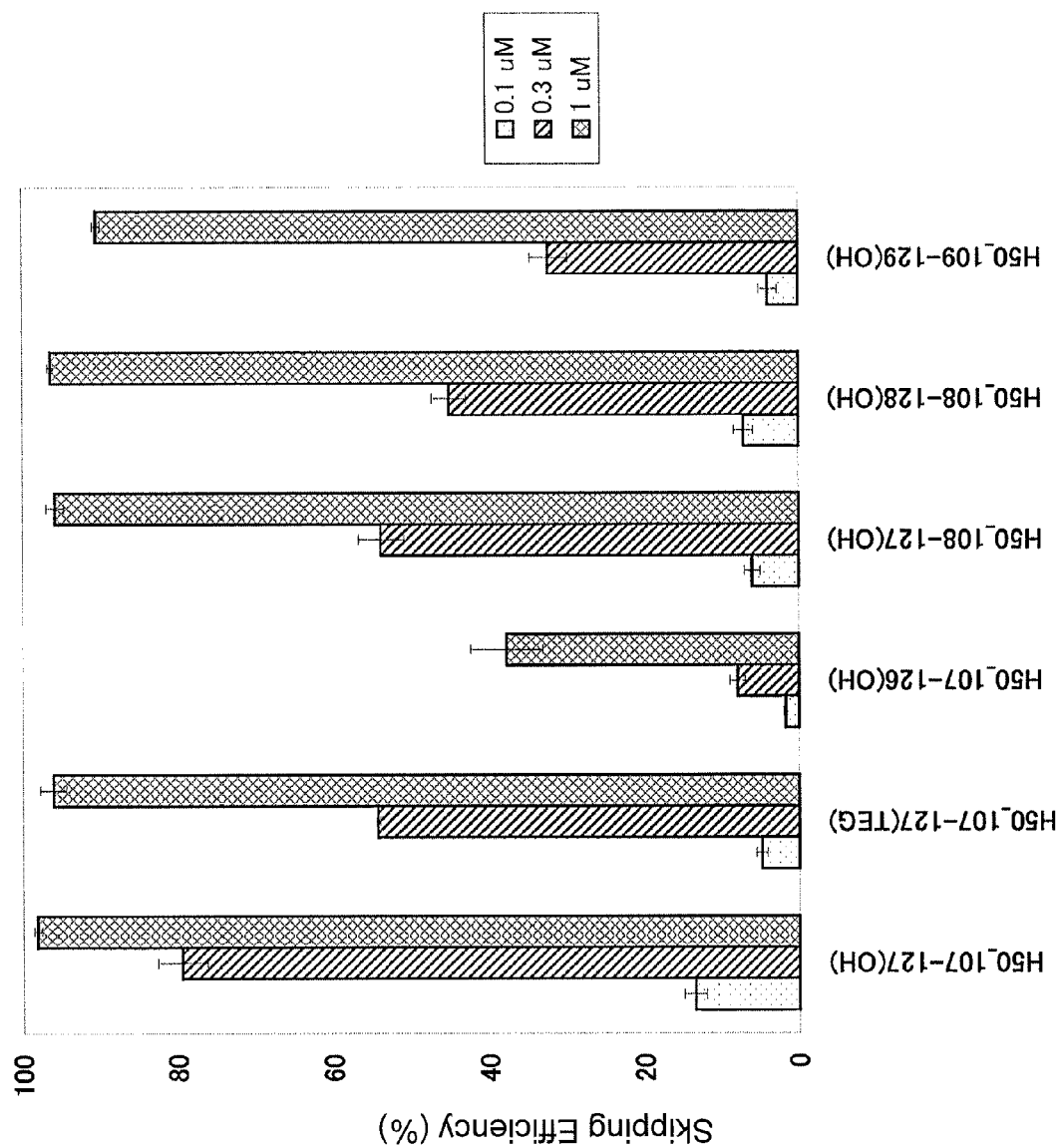
FIG. 19 shows the efficiency of exon 50 skipping by PMO in the human dystrophin gene in human rhabdomyosarcoma cell line (RD cells).

The results are shown in FIGS. 13 and 19. These experiments revealed that in RD cells the oligomers PMO No. 38 (H50_107-127 (OH)) of the present invention caused exon 50 skipping with a higher efficiency than the antisense oligomer PMO No. 39 or 40 (H50_90-114 (GT), H50_103-127 (GT)). Also, the experiments revealed that the oligomer PMO No. 38 caused exon 50 skipping with a higher efficiency than the oligomer PMO No. 45 (H50_107-127 (TEG)), whose end structure is different from that of the oligomer PMO No. 38 (FIG. 19).

Examination of Exon 44 Skipping

In Vitro Assay Using Human Fibroblasts

Test Example 9

The exon 44 skipping activity was determined using GM05112 cells (human DMD patient-derived fibroblasts with deletion of exon 45, Coriell Institute for Medical Research). As a growth medium, there was used Dulbecco's Modified Eagle Medium: Nutrient Mixture F-12 (DMEM/F-12) (Invitrogen Corp.) containing 10% FCS and 1% Penicillin/Streptmycin (P/S) (Sigma-Aldrich, Inc.) and the cells were cultured under conditions of 37° C. and 5% $CO_2$.

The cells were cultured in T225 flask and the 2.5 mL of retrovirus (ZsGreen1 coexpression) expressing human derived MyoD (SEQ ID NO: 38) and a final concentration of 8 µg/mL of polybrene (Sigma-Aldrich, Inc.) were added to 35 mL of the growth medium. After incubation at 32° C. for 2 days, the medium was exchanged to a fresh growth medium and incubation was further continued at 37° C. for 3 days. ZsGreen1-positive MyoD-transformed fibroblasts were collected by BD FACSAria Cell Sorter (BD Bioscience) and plated at $9\times10^4$ cells/well into a collagen-coated 24-well plate. The next day, the medium was replaced by a differentiation medium (DMEM/F-12 containing 2% equine serum (Invitrogen Corp.), 1% P/S and ITS Liquid Media Supplement (Sigma, Inc.)). The medium was exchanged every 2 to 3 days and incubation was continued to differentiate into myotubes.

On the 7th day after the medium was changed to the differentiation medium, the medium was replaced by a differentiation medium containing 6 µM at a final concentration of Endo-Porter (Gene Tools), and 1, 3, 10 µM of the oligomers PMO No. 26 and 31 were added thereto at a final concentration. After the cells were incubated for 7 days, the cells were collected to extract total RNA using RNeasy Mini Kit (QIAGEN). RT-PCR was performed with 50 ng of the extracted total RNA using a QIAGEN OneStep RT-PCR Kit. A reaction solution was prepared in accordance with the protocol attached to the kit. An iCycler (manufactured by Bio-Rad) was used as a thermal cycler. The RT-PCR program used is as follows.

50° C., 30 mins: reverse transcription
95° C., 15 mins: thermal denaturation
[94° C., 1 mins; 60° C., 1 mins; 72° C., 1 mins]×35 cycles: PCR amplification
72° C., 7 mins: final extension reaction The nucleotide sequences of the forward primer and reverse primer used for RT-PCR are given below.

```
Forward primer:
                              (SEQ ID NO: 36)
5'- GCTCAGGTCGGATTGACATT-3'

Reverse primer:
                              (SEQ ID NO: 37)
5'- GGGCAACTCTTCCACCAGTA-3'
```

The reaction product of RT-PCR above was separated by 2% agarose gel electrophoresis and gel images were captured with an image analyzer ImageQuant LAS 4000 mini (manufactured by FUJI Film). Using the attached soft, the polynucleotide level "A" of the band with exon 44 skipping and the polynucleotide level "B" of the band without exon 44 skipping were measured. Based on these measurement values of "A" and "B", the skipping efficiency was determined by the following equation:

Skipping efficiency(%)=A/(A+B)×100

Experimental Results

Figure 20:
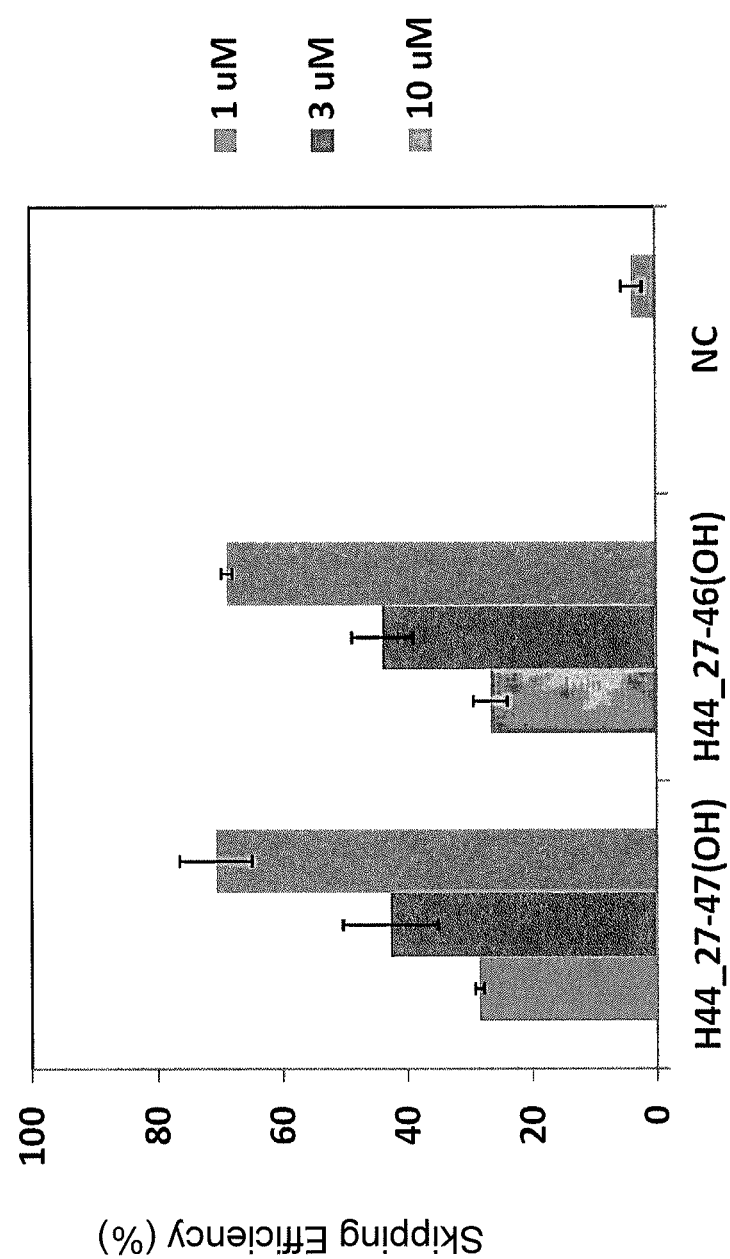
FIG. 20 shows the efficiency of exon 44 skipping by PMO in the human dystrophin gene in the fibroblasts from human DMD patient with deletion of exon 45 (GM05112 cells).

The result is shown in FIG. 20. These experiments revealed that in GM05112 cells the oligomers PMO No. 26 and 31 of the present invention caused exon 44 skipping with a high efficiency.

Test Example 10

A MyoD-transformed fibroblasts were prepared using GM05112 cells in accordance with the procedure of TEST EXAMPLE 9, and the cells were differentiated into myotubes. Subsequently, the differentiation medium was replaced by a differentiation medium containing 6 μM at a final concentration of Endo-Porter (Gene Tools), and the oligomers PMO Nos. 26 and 31 were added to the cells at a final concentration of 10 μM on the 6th day after the medium was changed to the differentiation medium. After incubation for 14 days, the cells were collected by a scraper using a cell lysis buffer RIPA buffer (manufactured by Pierce) containing a protease inhibitor cocktail Complete Mini (manufactured by Roche). The cell lysate were extracted from the cells by disrupting the cells by a ultrasonic crusher Bioruptor UCD-250 (Tosho Denki) and collecting the supernatant after centrifugation. The protein concentrations were quantified using a Pierce BCA protein assay kit (Pierce). The absorbance of 544 nm of wavelength was detected using a plate reader Thermo Appliskan Type2001 (Thermo Electron).

The 3 μg of cell lysates were electrophoresed in acrylamide gel NuPAGE Novex Tris-Acetate Gel 3-8% (manufactured by Invitrogen) and transferred onto a Immobilon-P membrane (manufactured by Millipore) using a semi-dry blotter. The transferred membrane was washed with PBS (PBST) containing 0.1% Tween20 and blocked with PBST containing 5% Amersham ECL Prime Blocking agent (GE Healthcare) in the refrigerator overnight. After the membrane was washed with PBST, the membrane was incubated in a solution of anti-dystrophin antibody (manufactured by NCL-Dysl, Novocastra) 50-fold diluted with Can Get Signal1 (manufactured by TOYOBO) at room temperature for 1 hour. After washing with PBST, the membrane was incubated in a solution of peroxidase-conjugated goat-anti-mouse IgG antibody (170-6516, Bio-Rad) 2,500-fold diluted with Can Get Signal1 (manufactured by TOYOBO) at room temperature for 10 minutes. After washing with PBST, the membrane was stained with ECL Plus Western Blotting Detection System (GE Healthcare). The chemiluminescence of the dystrophin protein deleted exon 44-45 was detected by lumino image analyzer ImageQuant LAS 4000 mini (FUJI Film).

Experimental Results

Figure 21:
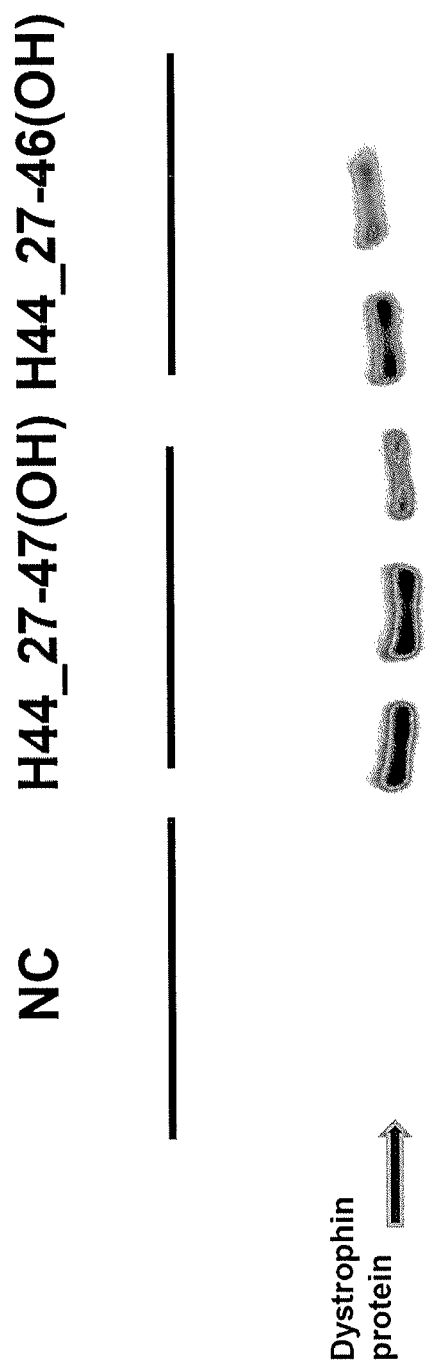
FIG. 21 shows the effect (Western Blotting) of exon 44 skipping by PMO in the human dystrophin gene in the fibroblasts from human DMD patient with deletion of exon 45 (GM05112 cells).

The results of Western blotting are shown in FIG. 21. In FIG. 21, the arrowhead represents a band of dystrophin protein of which the expression was confirmed. This experiment reveals that the oligomers PMO No. 26 and 31 of the present invention induced expression of dystrophin proteins in GM05112 cells.

Study of Exon 50 Skipping
In Vitro Assay Using Human Fibroblasts

Test Example 11

MyoD-transformed fibroblasts were prepared using GM05112 cells to differentiate into myotubes in accordance with the procedure of TEST EXAMPLE 9.

Subsequently, the differentiation medium was replaced by a differentiation medium containing 6 μM of Endo-Porter (Gene Tools), and a oligomer PMO No. 38 was added thereto at a final concentration of 0.1, 0.3, 1, 3, 10 μM on the 12th day after the medium was changed to the differentiation medium. After incubation for 2 days, the cells were collected. Total RNA was extracted from the cells, RT-PCR was performed and the skipping efficiency was determined in accordance with the procedure of TEST EXAMPLE 9, except that the nucleotide sequences of the forward primer and reverse primer given below were used for RT-PCR.

```
Forward primer:
                                    (SEQ ID NO: 103)
    5'- AACAACCGGATGTGGAAGAG-3'

Reverse primer:
                                    (SEQ ID NO: 104)
    5'- TTGGAGATGGCAGTTTCCTT-3'
```

Experimental Results

Figure 22:
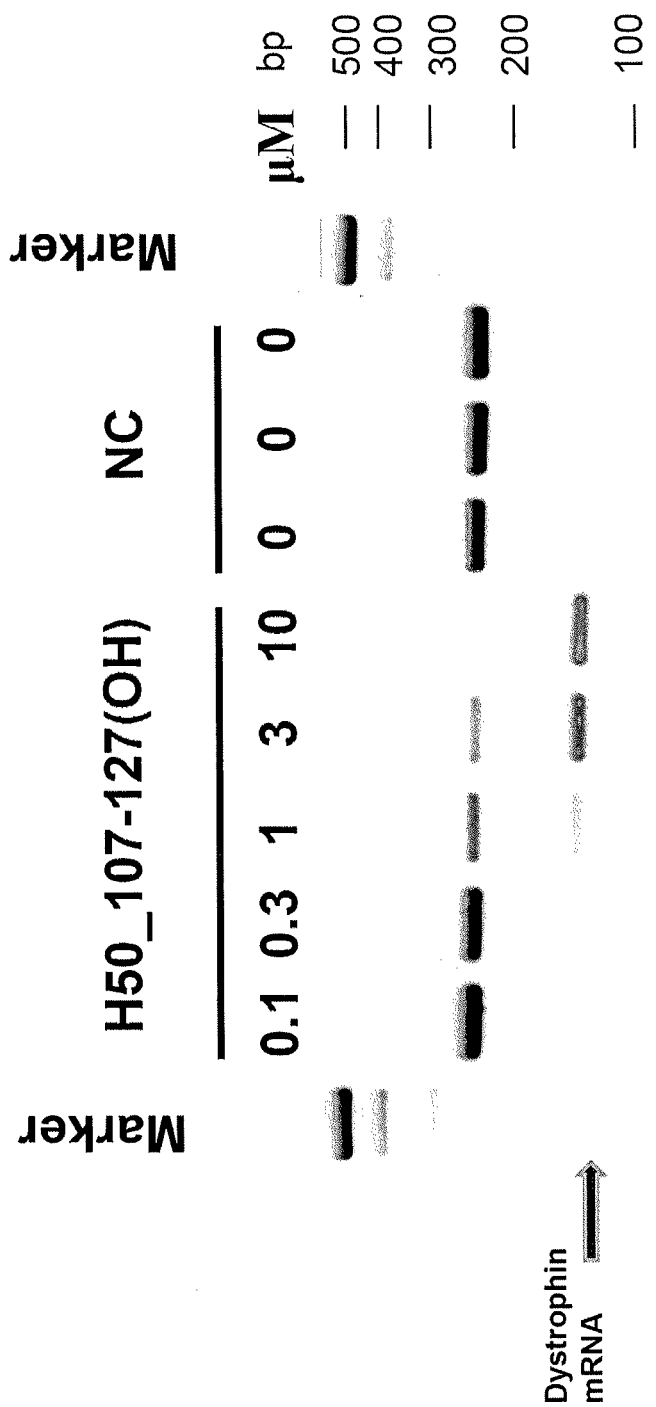
FIG. 22 shows the effect (RT-PCR) of exon 50 skipping by PMO in the human dystrophin gene in the fibroblasts from human DMD patient with deletion of exon 45 (GM05112 cells).
Figure 23:
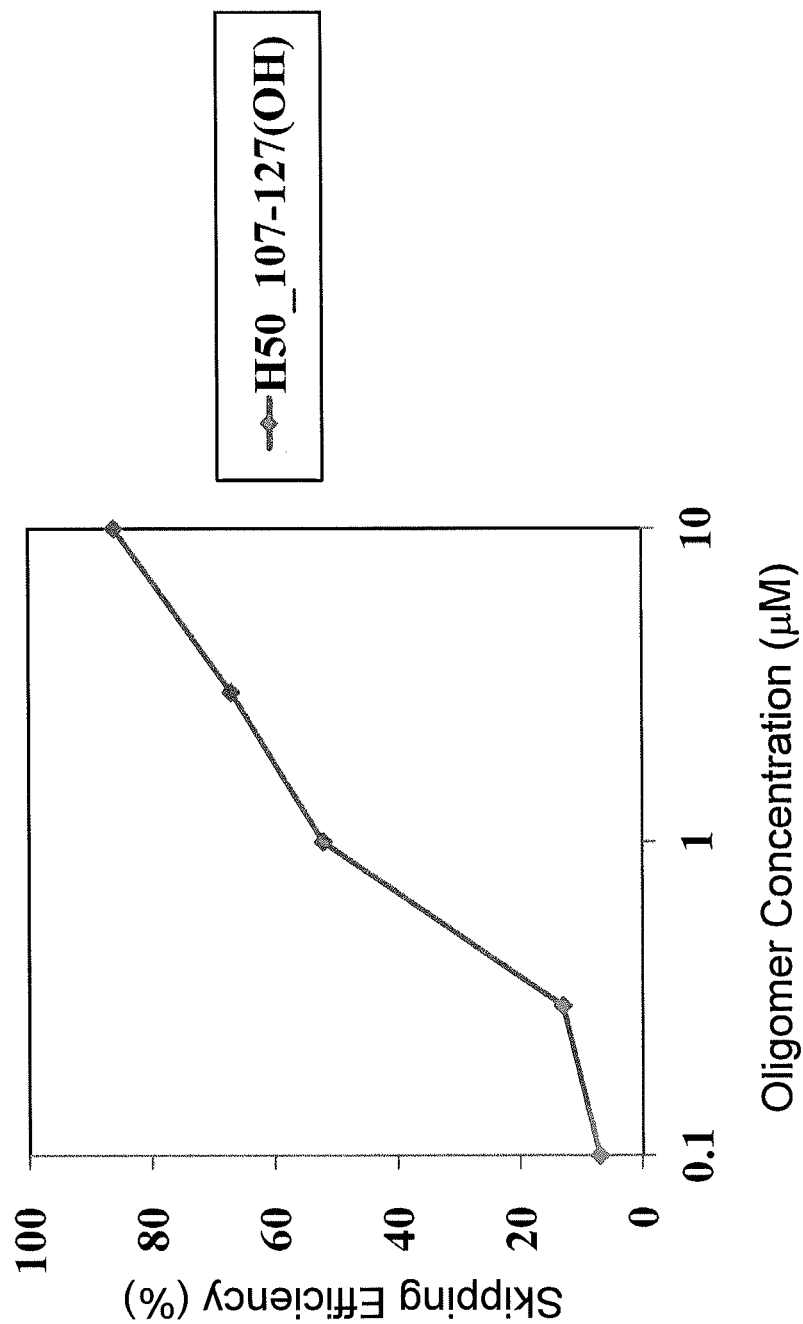
FIG. 23 shows the efficiency of exon 50 skipping by PMO in the human dystrophin gene in the fibroblasts from human DMD patient with deletion of exon 45 (GM05112 cells).

The result of RT-PCR is shown in FIG. 22 and the result of skipping efficiency is shown in FIG. 23. These experiments revealed that in GM05112 cells the oligomer PMO No. 38 of the present invention caused exon 50 skipping with a high efficiency and the value of $EC_{50}$ was 1.3 μM.

Test Example 12

Experiments for skipping were performed in accordance with the condition and the procedure of TEST EXAMPLE 11, except that 11-0627 cells (human DMD patient derived fibroblasts with duplication of exons 8-9, National Center of Neurology and Psychiatry neuromuscular disorder research resource repository) were used and the oligomer PMO No. 38 was added at a final concentration of 0.1, 1, 10 μM.

Experimental Results

Figure 26:
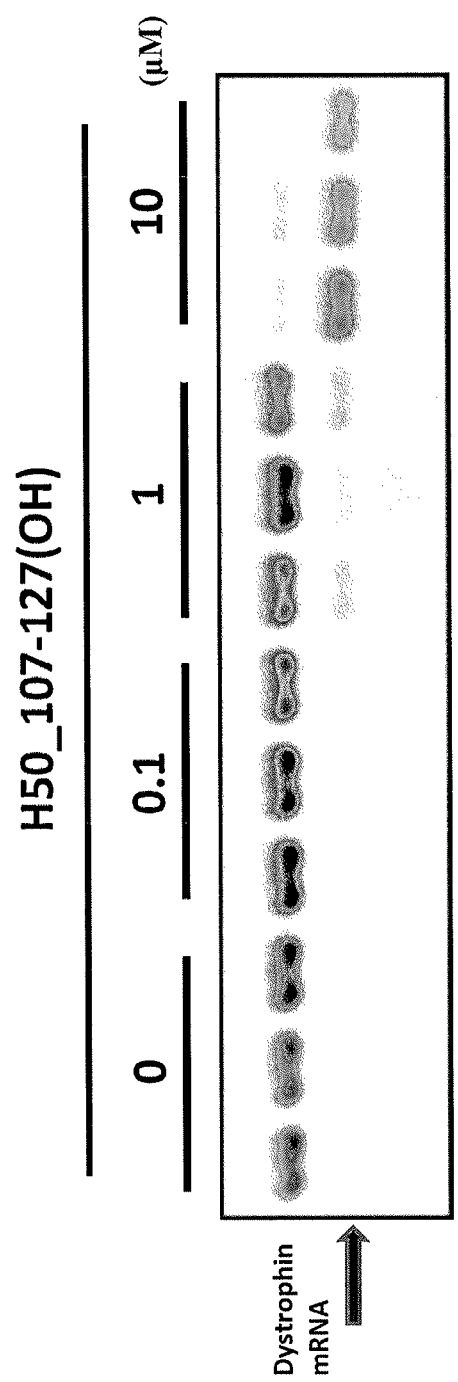
FIG. 26 shows the effect (RT-PCR) of exon 50 skipping by PMO in the human dystrophin gene in the fibroblasts from human DMD patient with duplication of exons 8-9 (11-0627 cells).
Figure 27:
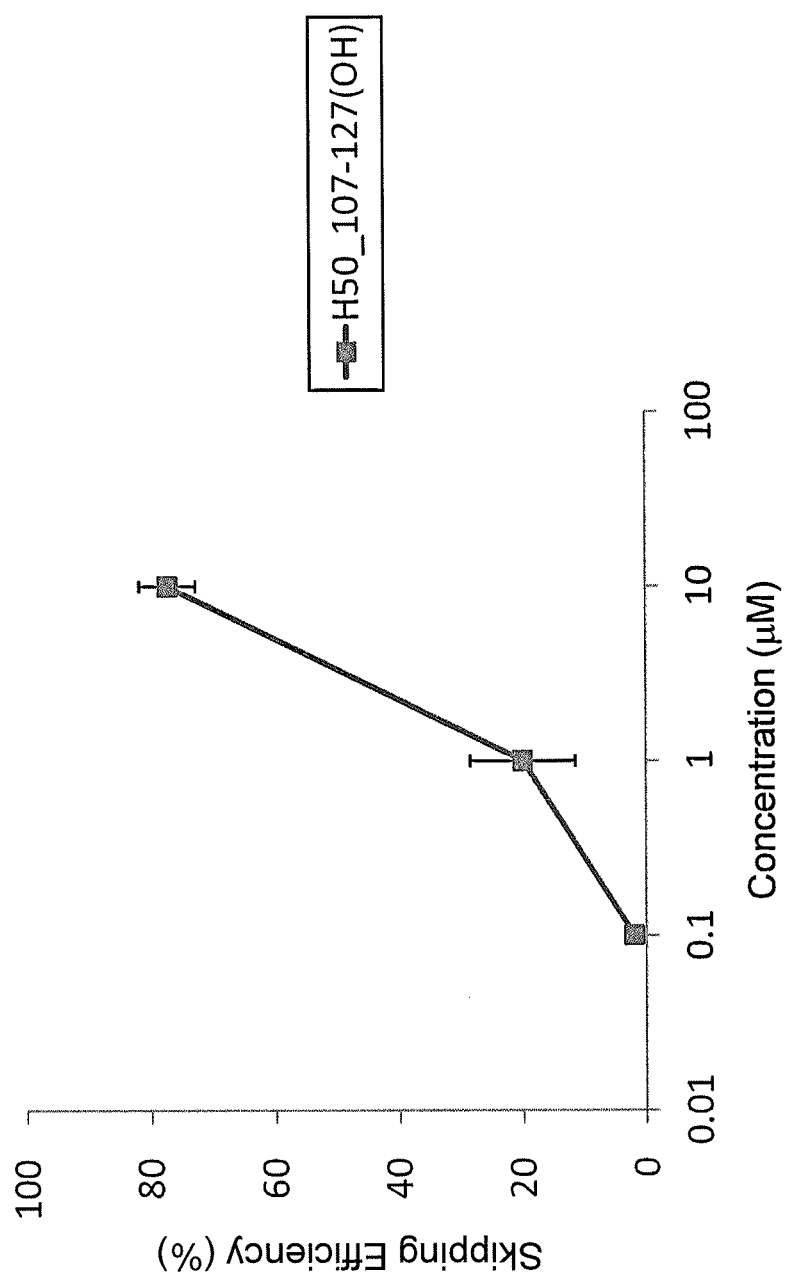
FIG. 27 shows the efficiency of exon 50 skipping by PMO in the human dystrophin gene in the fibroblasts from human DMD patient with duplication of exons 8-9 (11-0627 cells).

The result of RT-PCR is shown in FIG. 26 and the skipping efficiency is shown in FIG. 27. These experiments revealed that in 11-0627 cells the oligomer PMO No. 38 of the present invention caused exon 50 skipping with a high efficiency.

Test Example 13 pLVX-MyoD-ZsGreen1 Lentivirus Preparation pLVZ-puro (8120 bp, Clontech) was linearized by deleting 1164 bp nucleotides which is located on from XhoI site in the multicloning site (at 2816) to the site (at 3890) adjacent to the 3' end of Puromycin resistant gene coding region to prepare a linearized vector. Subsequently, the nucleotide sequences (2272 bp) which encodes human MyoD gene, IRES sequence, ZsGreen1 gene was integrated into the linearized vector in turn and then the lentivirus expression vector pLVX-MyoD-ZsGreen1 (9210 bp) was prepared. Lenti-X 293T cells were plated onto 10 cm collagen coated dish in accordance with the protocol attached to Lenti-X HTX Packaging System (Clontech). Lentivirus expression vector and packaging vector were transfected into fibroblasts three days before infection. After four hours, the medium was exchanged and the cells were incubated for three days without exchanging medium. On the day of infection, the culture supernatant was collected as a virus solution (about 9 mL for 10 cm dish). The culture supernatant was filtrated by cellstrainer (40 μm) and then centrifuged by 500×g, 10 min. This supernatant was concentrated in accordance with the protocol attached to Lenti-X Concentrator (Clontech) and then dissolved in DMEM/F12 medium to ten times the concentration of the collected culture supernatant. This solution was used as a virus solution.

Virus Infection into Fibroblasts

GM04364 cells (human DMD patient derived fibroblasts deleted exons 51-55, Coriell Institute for Medical Research) were plated on a collagen-coated 24-well plate by $3\times10^4$/well by the day of infection. On the day of infection, 400 µL of the differentiation medium, 100 µL of the virus solution, and 8 µg/mL of polybrene at a final concentration per well were added. The day after infection, the medium containing virus was exchanged into 500 µL of the differentiation medium. The differentiation medium was exchanged every 2 or 3 days and the cells were incubated for 12 days to induce differentiation into myotubes.

On the 12th day after the medium was exchanged into the differentiation medium, the medium was replaced by a differentiation medium containing 6 µM Endo-Porter (Gene Tools) at a final concentration, and 0.1, 0.3, 1, 3, 10 µM of the oligomer PMO No. 38 was added thereto at a final concentration. After incubation for 2 days, the cells were collected. The skipping efficiency was determined in accordance with the procedure of TEST EXAMPLE 11, except that the nucleotide sequences of the forward primer and reverse primer given below were used for RT-PCR.

```
Forward primer:
                                    (SEQ ID NO: 103)
5'- AACAACCGGATGTGGAAGAG-3'

Reverse primer:
                                    (SEQ ID NO: 70)
5'- CTGCCGGCTTAATTCATCAT-3'
```

Experimental Results

Figure 28:
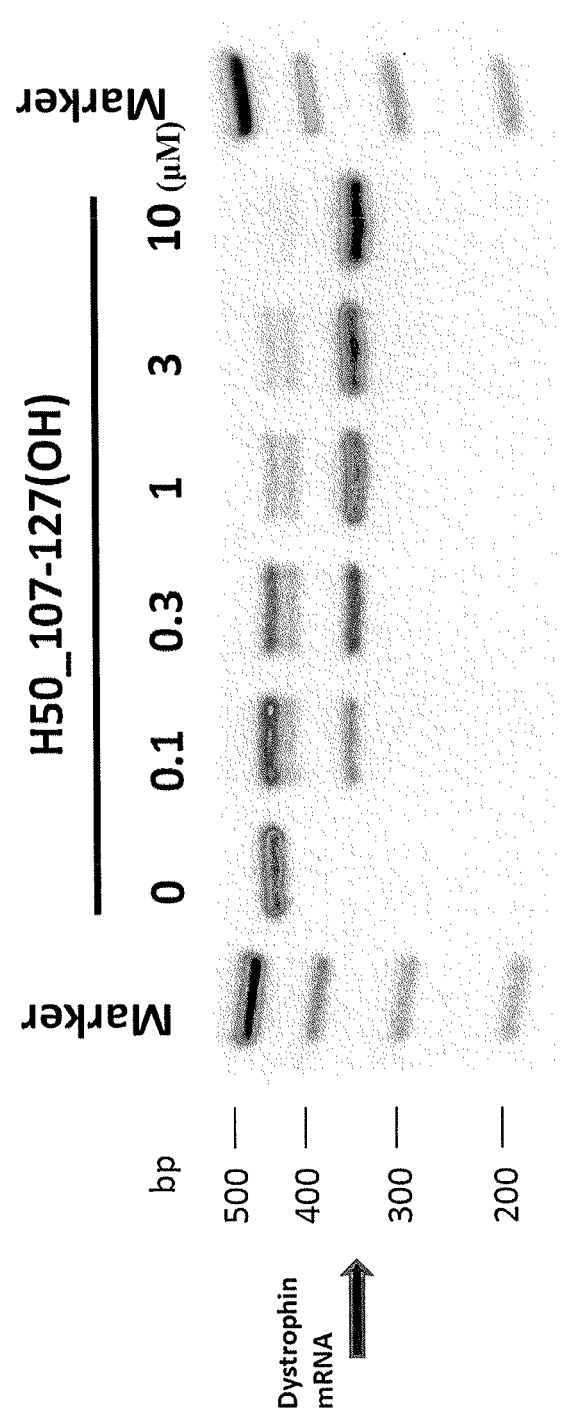
FIG. 28 shows the effect (RT-PCR) of exon 50 skipping by PMO in the human dystrophin gene in the fibroblasts from human DMD patient with deletion of exons 51-55 (GM04364 cells).
Figure 29:
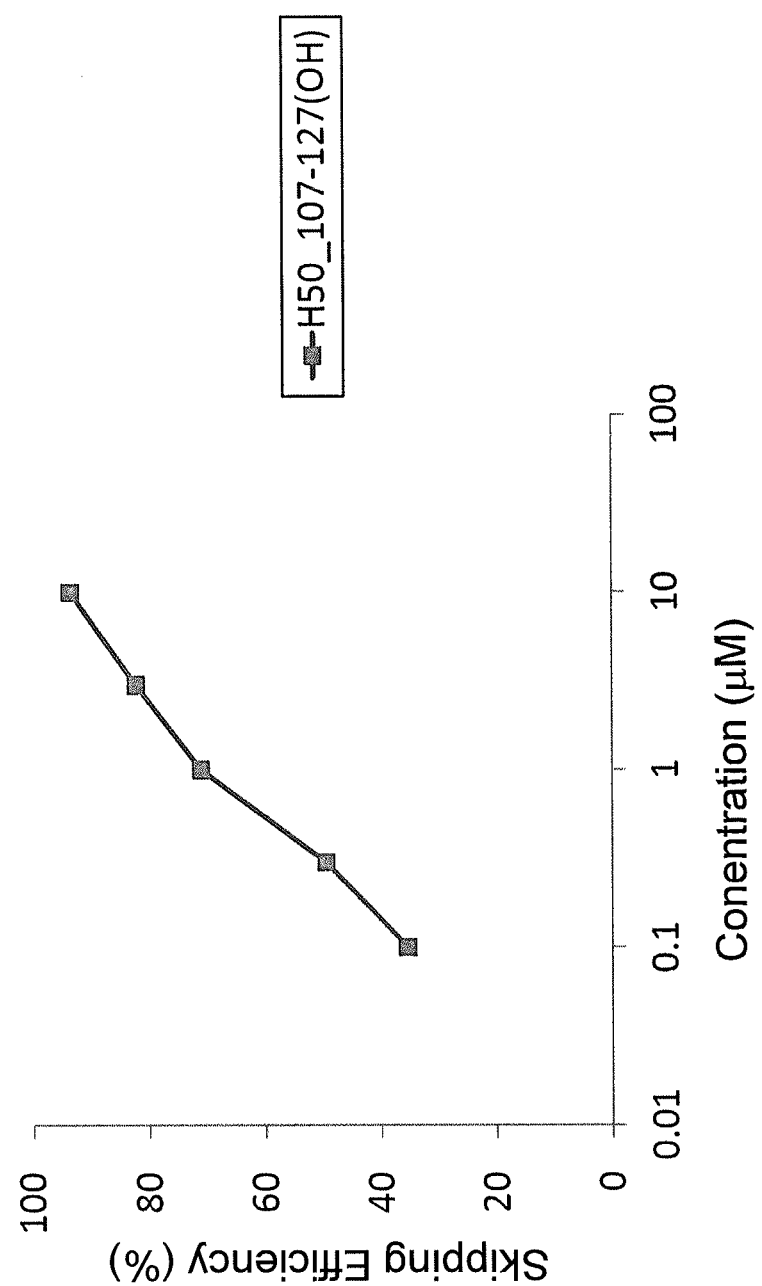
FIG. 29 shows the efficiency of exon 50 skipping by PMO in the human dystrophin gene in the fibroblasts from human DMD patient with deletion of exons 51-55 (GM04364 cells).

The result of RT-PCR is shown in FIG. 28 and the skipping efficiency is shown in FIG. 29. These experiments revealed that in GM04364 cells the oligomer PMO No. 38 of the present invention caused exon 50 skipping with a high efficiency.

Study of Exon 55 Skipping
In Vitro Assay Using Human Fibroblasts

Test Example 14

Experiments were performed in accordance with the condition and the procedure of TEST EXAMPLE 11, except that the oligomers PMO No. 14 and 21 were used and the RT-PCR was performed using the primers below.

```
Forward primer:
                                    (SEQ ID NO: 69)
5'- CATGGAAGGAGGGTCCCTAT-3'

Reverse primer:
                                    (SEQ ID NO: 70)
5'- CTGCCGGCTTAATTCATCAT-3'
```

Experimental Results

Figure 24:
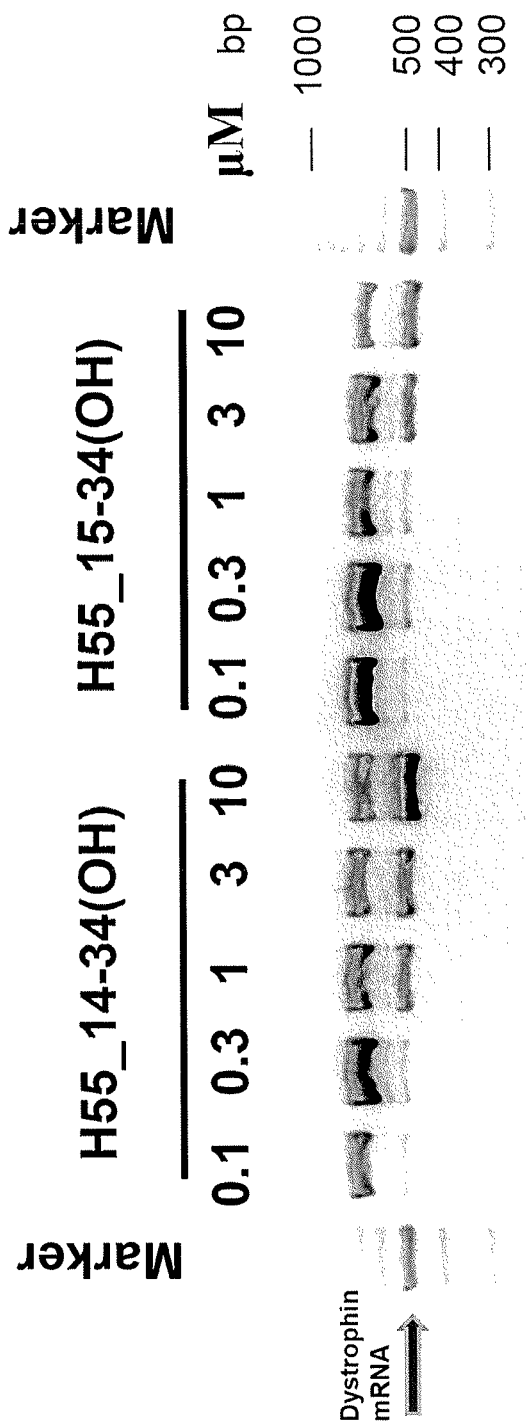
FIG. 24 shows the effect (RT-PCR) of exon 55 skipping by PMO in the human dystrophin gene in the fibroblasts from human DMD patient with deletion of exon 45 (GM05112 cells).
Figure 25:
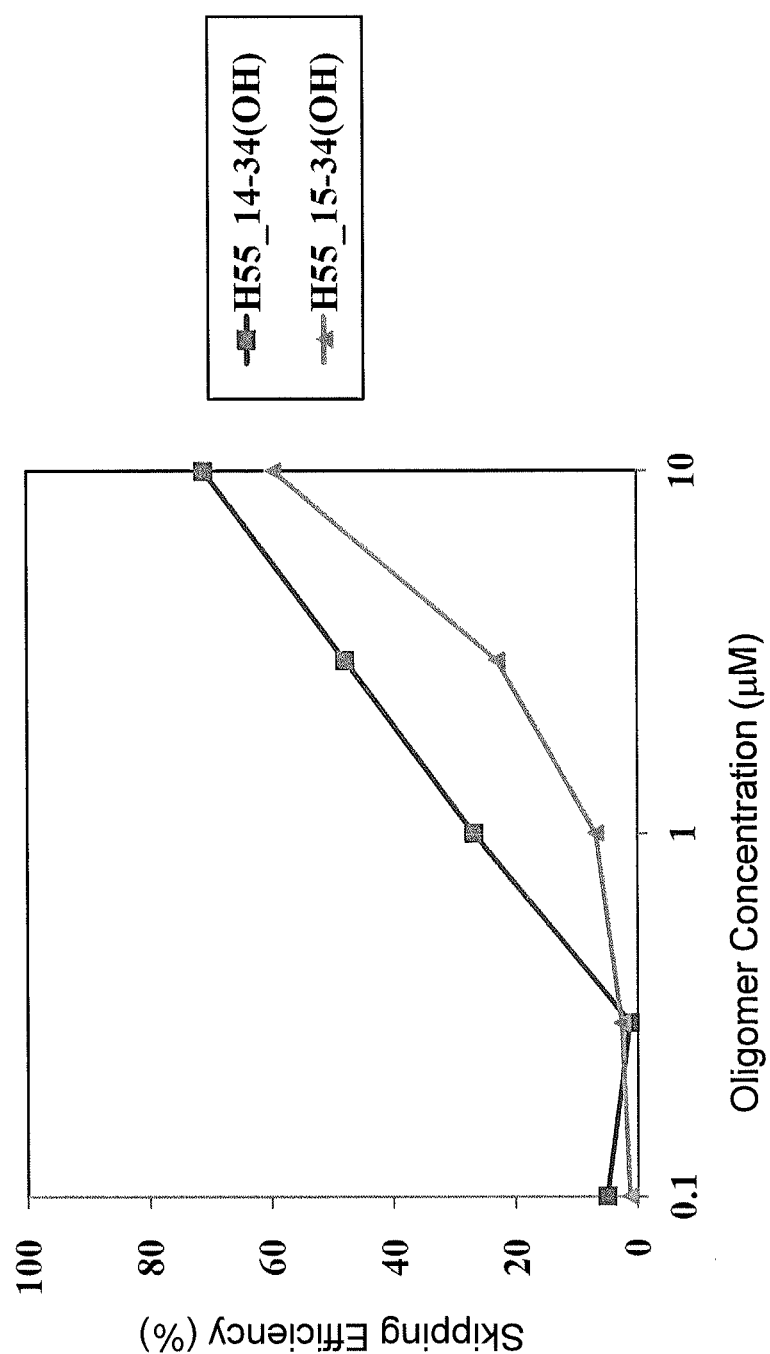
FIG. 25 shows the efficiency of exon 55 skipping by PMO in the human dystrophin gene in the fibroblasts from human DMD patient with deletion of exon 45 (GM05112 cells).

The result of RT-PCR is shown in FIG. 24 and the skipping efficiency is shown in FIG. 25. These experiments revealed that in GM05112 cells the oligomers PMO No. 14 and 21 of the present invention caused exon 55 skipping with a high efficiency and the value of $EC_{50}$ was 3.5 µM and 7.5 µM, respectively.

Test Example 15

Experiments were performed in accordance with the condition and the procedure of TEST EXAMPLE 13, except that the 04-035 cells (human DMD patient derived cells with single deletion of exon 54, National Center of Neurology and Psychiatry neuromuscular disorder research resource repository) were used and 1, 3, 10 µM of the oligomers PMO No. 14 and 21 at a final concentration were added and the RT-PCR was performed using the primers below.

```
Forward primer:
                                    (SEQ ID NO: 69)
5'- CATGGAAGGAGGGTCCCTAT-3'

Reverse primer:
                                    (SEQ ID NO: 70)
5'- CTGCCGGCTTAATTCATCAT-3'
```

Experimental Results

Figure 30:
FIG. 30 shows the effect (RT-PCR) of exon 55 skipping by PMO in the human dystrophin gene in the fibroblasts from human DMD patient with deletion of exon 54 (04-035 cells).
Figure 31:
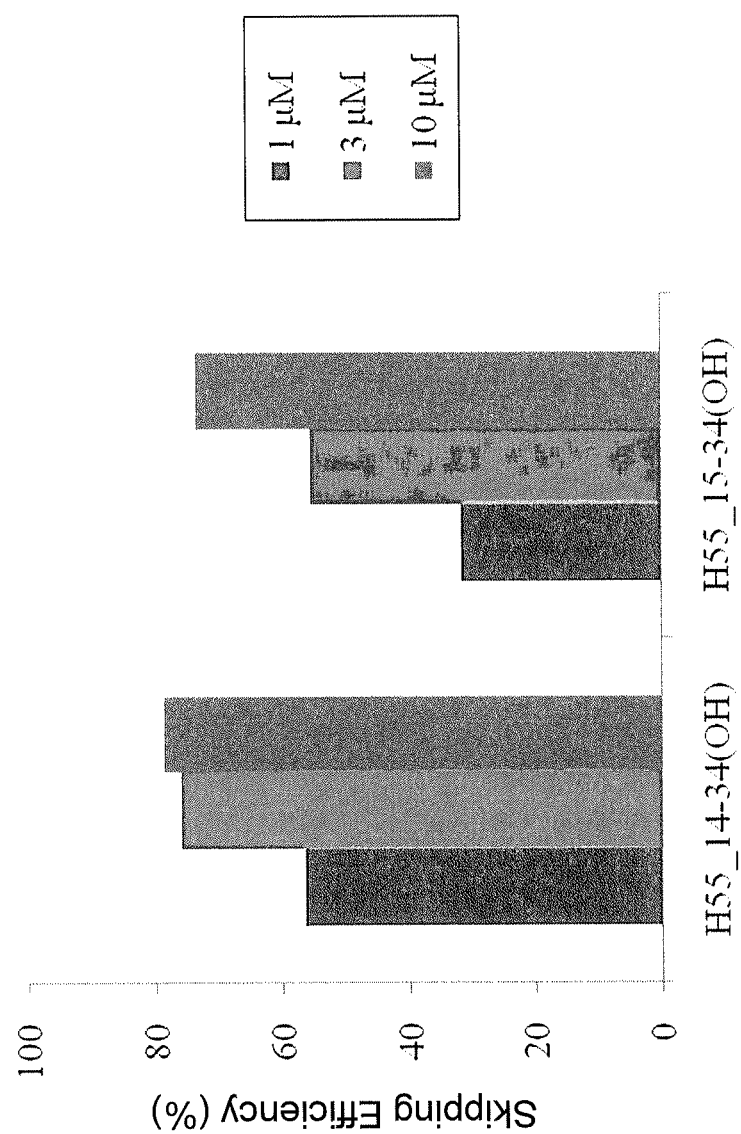
FIG. 31 shows the efficiency of exon 55 skipping by PMO in the human dystrophin gene in the fibroblasts from human DMD patient with deletion of exon 54 (04-035 cells).

The result of RT-PCR is shown in FIG. 30 and the skipping efficiency is shown in FIG. 31. These experiments revealed that in human DMD patient derived cells with single deletion of exon 54, the oligomers PMO No. 14 and 21 of the present invention caused exon 55 skipping with a high efficiency.

INDUSTRIAL APPLICABILITY

Experimental results in TEST EXAMPLES demonstrate that the oligomers of the present invention caused exon skipping with a markedly high efficiency in both RD cells and DMD patients derived cells.

Therefore, the oligomers of the present invention are extremely useful for the treatment of DMD.

The invention claimed is:

1. An antisense oligomer which causes skipping of the 50th exon in a human dystrophin gene, consisting of a nucleotide sequence complementary to any one of the nucleotide sequences consisting of the 106th to the 126th, the 107th to the 127th, the 108th to the 127th, the 108th to the 128th, or the 109th to the 129th nucleotides, from the 5' end of the human dystrophin gene's 50th exon, wherein the 50exon of the human dystrophin gene consists of position 1 to 109 of the nucleotide sequence SEQ ID NO: 3, and wherein the antisense oligomer is a morpholino opligomer or an oligonucleotide in which the sugar moiety and/or the phosphate-binding region of at least one nucleotide constituting the oligonucleotide is modified.

2. The antisense oligomer according to claim 1, which consists of a complementary sequence to the nucleotide sequences consisting of the 106th to the 126th or the 107th to the 127th nucleotides, from the 5' end of the human dystrophin gene's 50th exon.

3. The antisense oligorner according to claim 1, consisting of the nucleotide sequence shown by any one selected from the group consisting of the 4th to the 24th and the 3rd to the 23rd nucleotides Of SEQ ID NO: 7.

4. The antisense oligomer according to claim 1, wherein the sugar moiety of at least one nucleotide constituting the oligonucleotide is a ribose in which the 2'-OH group is replaced by any one selected from the group consisting of OR, R, R'OR, SH, SR, $NH_2$, NHR, $NR_2$, $N_3$, CN, F, Cl, Br and I (wherein R is an alkyl or an aryl and R' is an alkylene).

5. The antisense oligomer according to claim 1, wherein the phosphate-binding region of at least one nucleotide constituting the oligonucleotide comprises any one selected from the group consisting of a phosphorothioate bond, a phosphorodithioate bond, an alkylphosphonate bond, a phosphoramidate bond and a boranophosphate bond.

6. The antisense oligomer according to claim 1, which is a morpholino oligomer.

7. The antisense oligomer according to claim 6, which is a phosphorodiamidate morpholino oligomer.

8. The antisense oligomer according to claim 6, wherein the 5' end of the morpholino oligomer is any one of the groups of chemical formulae (1) to (3) below:

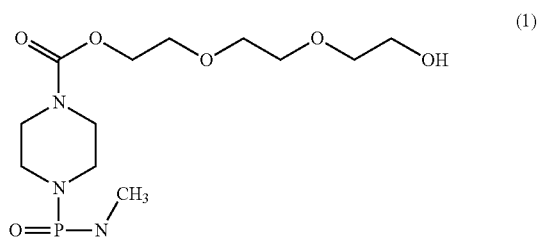

(1)

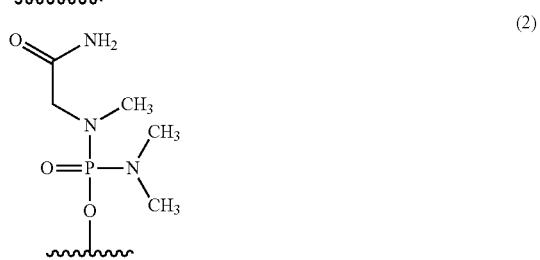

(2)

(3)

9. A pharmaceutical composition for the treatment of muscular dystrophy, comprising as an active ingredient the antisense oligomer according to claim 1, or a pharmaceutically acceptable salt or hydrate thereof.

* * * * *

UNITED STATES PATENT AND TRADEMARK OFFICE
CERTIFICATE OF CORRECTION

PATENT NO. : 9,512,424 B2
APPLICATION NO. : 14/368307
DATED : December 6, 2016
INVENTOR(S) : Naoki Watanabe et al.

It is certified that error appears in the above-identified patent and that said Letters Patent is hereby corrected as shown below:

In the Claims

Column 105, Line 9, replace "50exon" with --50th exon--

Column 105, Line 11, replace "opligomer" with --oligomer--

Column 105, Line 23, replace "Of" with --of--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*